US011155823B2

(12) United States Patent
Beisel et al.

(10) Patent No.: US 11,155,823 B2
(45) Date of Patent: Oct. 26, 2021

(54) METHODS AND COMPOSITIONS FOR EFFICIENT DELIVERY OF NUCLEIC ACIDS AND RNA-BASED ANTIMICROBIALS

(71) Applicant: NORTH CAROLINA STATE UNIVERSITY, Raleigh, NC (US)

(72) Inventors: Chase Lawrence Beisel, Raleigh, NC (US); Ahmed Abdelshafy Mahmoud Gomaa, Raleigh, NC (US); Michelle Luo, Cary, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 845 days.

(21) Appl. No.: 15/735,028

(22) PCT Filed: Jun. 15, 2016

(86) PCT No.: PCT/US2016/037493
§ 371 (c)(1),
(2) Date: Dec. 8, 2017

(87) PCT Pub. No.: WO2016/205276
PCT Pub. Date: Dec. 22, 2016

(65) Prior Publication Data
US 2018/0155729 A1 Jun. 7, 2018

Related U.S. Application Data

(60) Provisional application No. 62/175,749, filed on Jun. 15, 2015.

(51) Int. Cl.
| | |
|---|---|
| *C12N 15/70* | (2006.01) |
| *C12N 15/10* | (2006.01) |
| *C12P 19/34* | (2006.01) |
| *A01N 63/40* | (2020.01) |
| *A61P 31/04* | (2006.01) |
| *C12N 7/00* | (2006.01) |
| *C12N 9/10* | (2006.01) |
| *C12N 9/22* | (2006.01) |
| *C12N 9/96* | (2006.01) |
| *C12N 15/11* | (2006.01) |
| *A61K 38/00* | (2006.01) |

(52) U.S. Cl.
CPC .............. *C12N 15/70* (2013.01); *A01N 63/40* (2020.01); *A61P 31/04* (2018.01); *C12N 7/00* (2013.01); *C12N 9/1007* (2013.01); *C12N 9/22* (2013.01); *C12N 9/96* (2013.01); *C12N 15/102* (2013.01); *C12N 15/11* (2013.01); *C12P 19/34* (2013.01); *A61K 38/00* (2013.01); *C12N 2310/20* (2017.05); *C12N 2795/10143* (2013.01); *C12N 2795/14143* (2013.01); *Y02A 50/30* (2018.01)

(58) Field of Classification Search
CPC ........ C12N 15/70; C12N 7/00; C12N 9/1007; C12N 9/22; C12N 9/96; C12N 15/11; C12N 15/102; C12N 2310/20; C12N 2795/10143; C12N 2795/14143; C12P 19/34; A61P 31/04; A01N 63/00; Y02A 50/30; A61K 38/00
See application file for complete search history.

(56) References Cited

U.S. PATENT DOCUMENTS

| | | | |
|---|---|---|---|
| 9,023,649 B2 | 5/2015 | Mali et al. | |
| 9,260,723 B2 | 2/2016 | Mali et al. | |
| 2006/0199190 A1 | 9/2006 | Russell et al. | |
| 2009/0007301 A1 | 1/2009 | Wintz et al. | |
| 2013/0288251 A1 | 10/2013 | Horvath et al. | |
| 2014/0068797 A1 | 3/2014 | Doudna et al. | |
| 2014/0113376 A1 | 4/2014 | Sorek et al. | |
| 2014/0186958 A1 | 7/2014 | Zhang et al. | |
| 2014/0273233 A1 | 9/2014 | Chen et al. | |
| 2014/0356867 A1 | 12/2014 | Peter et al. | |
| 2014/0356956 A1 | 12/2014 | Church et al. | |
| 2015/0050699 A1 | 2/2015 | Siksnys et al. | |
| 2015/0056628 A1 | 2/2015 | Russell et al. | |
| 2015/0064138 A1 | 3/2015 | Lu et al. | |
| 2015/0093473 A1 | 4/2015 | Barrangou et al. | |
| 2015/0098954 A1 | 4/2015 | Hyde et al. | |
| 2015/0132263 A1 | 5/2015 | Liu et al. | |
| 2015/0291961 A1 | 10/2015 | Siksnys et al. | |
| 2015/0315576 A1 | 11/2015 | Caliando et al. | |
| 2015/0353901 A1 | 12/2015 | Liu et al. | |
| 2016/0017366 A1 | 1/2016 | Chen et al. | |

(Continued)

FOREIGN PATENT DOCUMENTS

| | | |
|---|---|---|
| EP | 286267 A1 | 4/2015 |
| EP | 2860267 | 4/2015 |

(Continued)

OTHER PUBLICATIONS

Hochstrassera et al. "CasA mediates Cas3-catalyzed target degradation during CRISPR RNA-guided interference." Proc Natl Acad Sci USA.May 6, 2014; 111 (18):6618-23. (Year: 2014).*
Nizet et al. "Bacterial sepsis and meningitis." In: Remington J, Klein J, Wilson C, et al., editors. Infectious diseases of the fetus and newborn infant. 7th edition. Philadelphia, PA: Saunders/Elsevier; 2011. pp. 222-275. (Year: 2011).*
Sashital et al. "Mechanism of foreign DNA selection in a bacterial adaptive immune system."Mol Cell.Jun. 8, 2012;46(5):606-15. (Year: 2012).*
Boudry et al. "Function of CRISPR-Cas System of the Human Pathogen Clostridium difficile" mBio, 6(5):1-15 2015.
Beloglazova et al. "Structure and activity of the Cas3 HD nuclese MJ0384, and effector enzyme of the CRISPR Interference" The EMBO Journal, 30(22) 4616-4627 (2011).

(Continued)

*Primary Examiner* — Titilayo Moloye
(74) *Attorney, Agent, or Firm* — Myers Bigel, P.A.

(57) ABSTRACT

The invention relates to the methods for modifying the methylation pattern of bacteriophage DNA and phagemid DNA and to methods for selective killing of bacteria using lysogenic bacteriophages comprising bacteriophage DNA or phagemid DNA comprising components of an engineered CRISPR-Cas system.

12 Claims, 18 Drawing Sheets

(56) References Cited

U.S. PATENT DOCUMENTS

| | | |
|---|---|---|
| 2016/0024510 A1 | 1/2016 | Bikard et al. |
| 2016/0186152 A1 | 6/2016 | Brouns et al. |
| 2016/0186213 A1 | 6/2016 | Zhang et al. |
| 2016/0289700 A1 | 10/2016 | Barrangou et al. |
| 2016/0298096 A1 | 10/2016 | Charpentier et al. |
| 2016/0333348 A1 | 11/2016 | Clube et al. |
| 2016/0345578 A1 | 12/2016 | Barrangou et al. |
| 2017/0002339 A1 | 1/2017 | Barrangou et al. |
| 2017/0028083 A1 | 2/2017 | Beisel et al. |
| 2017/0196225 A1 | 7/2017 | Clube et al. |
| 2017/0246221 A1 | 8/2017 | Clube et al. |
| 2017/0275648 A1 | 9/2017 | Barrangou et al. |
| 2018/0064114 A1 | 3/2018 | Clube |
| 2018/0064115 A1 | 3/2018 | Clube et al. |
| 2018/0070594 A1 | 3/2018 | Clube et al. |
| 2018/0084785 A1 | 3/2018 | Clube |
| 2018/0084786 A1 | 3/2018 | Clube |
| 2018/0146681 A1 | 5/2018 | Clube |
| 2018/0200387 A1 | 7/2018 | Porteus |
| 2018/0258411 A1 | 9/2018 | Kadiyala et al. |
| 2018/0273937 A1 | 9/2018 | Beisel et al. |

FOREIGN PATENT DOCUMENTS

| | | |
|---|---|---|
| WO | 2006/113709 | 10/2006 |
| WO | WO 2010/054154 | 5/2010 |
| WO | WO 2010/075424 | 7/2010 |
| WO | WO 2013/098244 | 7/2013 |
| WO | 2013/141680 | 9/2013 |
| WO | WO 2013/176772 | 11/2013 |
| WO | WO 2013/188522 | 12/2013 |
| WO | WO 20131188638 | 12/2013 |
| WO | WO 2014/022702 | 2/2014 |
| WO | WO 2014/065596 | 5/2014 |
| WO | WO 2014/071235 | 5/2014 |
| WO | 2014/093479 | 6/2014 |
| WO | WO 2014/110006 | 7/2014 |
| WO | WO 2014/113493 | 7/2014 |
| WO | WO 20141124226 | 8/2014 |
| WO | WO 2014/144155 | 9/2014 |
| WO | WO 2014/150624 | 9/2014 |
| WO | WO 20141144592 | 9/2014 |
| WO | WO 2014/186686 | 11/2014 |
| WO | 2014/204727 | 12/2014 |
| WO | WO 2014/191128 | 12/2014 |
| WO | WO 2014/191518 | 12/2014 |
| WO | WO 2014/201015 | 12/2014 |
| WO | WO 2014/2014727 | 12/2014 |
| WO | WO 2015/021353 | 2/2015 |
| WO | WO 2015/026886 | 2/2015 |
| WO | WO 2015/034872 | 3/2015 |
| WO | WO 2015/035139 | 3/2015 |
| WO | WO 2015/040402 | 3/2015 |
| WO | WO 2015/053995 | 4/2015 |
| WO | WO 2015/070193 | 5/2015 |
| WO | WO 2015/077290 | 5/2015 |
| WO | 2015/089486 | 6/2015 |
| WO | WO 2015/089277 | 6/2015 |
| WO | WO 2015/089406 | 6/2015 |
| WO | 2015112896 A2 | 7/2015 |
| WO | WO 2015/116686 | 8/2015 |
| WO | WO 2015/119941 | 8/2015 |
| WO | WO/2015/139139 | 9/2015 |
| WO | 2015/159068 | 10/2015 |
| WO | WO 2015/148680 | 10/2015 |
| WO | WO 2015/153791 | 10/2015 |
| WO | WO 2015/153889 | 10/2015 |
| WO | WO 2015/153940 | 10/2015 |
| WO | WO 2015/155686 | 10/2015 |
| WO | WO 2015/159086 | 10/2015 |
| WO | WO 2015/159087 | 10/2015 |
| WO | WO 2015/160683 | 10/2015 |
| WO | WO 2015/189693 | 12/2015 |
| WO | WO 2015/200555 | 12/2015 |
| WO | WO 2016/084088 | 6/2016 |
| WO | WO 2016/177682 | 11/2016 |
| WO | 2016/196361 | 12/2016 |
| WO | 2017/027423 | 2/2017 |
| WO | 2017/066497 | 4/2017 |
| WO | 2017/112620 | 6/2017 |
| WO | 2017/147507 | 8/2017 |

OTHER PUBLICATIONS

Beisel CL et al. A CRISPR design for next-generation antimicrobials. Genome Biology. 2014; 15: 516, 4 pages.
Citorik RJ et al. "Sequence-specific antimicrobials using efficiently delivered RNA-guiding nucleases Supplemental Material." Nature Biotechnology. Sep. 21, 2014; 32(11): 1141-1145. DOI:10.1038/nbt.3011, 14 pages.
Final Office Action, U.S. Appl. No. 15/133,656, dated Jul. 30, 2018, 8 pages.
Liu S et al. Complete genome sequence of *Lactobacillus buchneri* NRRL B-30929, a novel strain from a commercial ethanol plant. Journal of Bacteriology. Aug. 2011; 193(15): 4019-4020.
Liu S et al. NCBI (2011) CRISPR-associated protein, Csn1 family [Lactobacillus buchneri], pp. 1-3.
Milani C et al. Genomic encyclopedia of type strains of the genus Bifidobaoterium. Applied and Environmental Microbiology, Oct. 2014; 80(20): 6290-6302.
Database GenBank [online]. NBI, U.S. National Library of Medicine. Aug. 5, 2014. "CRISPER-associated protein, Csn1 family [Bifidobacterium bombi DSM 19703]." XP002785852, retrieved from NCBI accession No. GenBank: KFF31259. Database accession No. KFF31259. 1 page.
Edgar et al. Supplemental Material "The *Escherichia coli* CRISPR System Protects from Lysogenization, Lysogens, and Prophage induction" Journal of Bacteriology, 192(23): 6292-6294 2010.
Shinkai "Structure and Function of CRISPR-Cas System" Seibutsu Butsuri, 54(5):247-252 (2014) Abstract Only .
Extended European Search Report regarding European Application No. EP19196063, dated Jun. 26, 2020 12 pages.
Third Party Observations corresponding to European Patent Application No. 16804164.8, dated Jul. 24, 2019 60 pages.
Third Party Observations corresponding to European Patent Application No. 16812275.2, dated May 15, 2020 108 pages.
International Search Report and Written Opinion, PCT/US2018/034322, dated Sep. 13, 2018, 7 pages.
Third Party Observation filed in European Application No. 16812275.2 on Aug. 31, 2018, 89 pages.
Lovisolo et al. "Coevolution of Viruses with hosts and vectors and possible pleontology" advances in virus research, 62:325-379 (2003).
Kesik et al. "Characterizing the biology of novel lytic bacteriophages infecting multidrug resistant Klebsiella pneumoniae" Virology Journal, vol. 10, 12 pages (2013).
Ajdic et al. "hypothetical protein SMU_1405c [*Streptococcus* mutans UA159]", Proc. Natl. Acad. Sci. U.S.A. 99 (22), 14434-14439 (2002) URL: https://www.ncbi.nlm.nih.gov/protein/NP_721764.1/, retrieved Jul. 20, 2018.
Cochrane Kyla et ai., "Complete genome sequences and analysis of the Fusobacterium nucleatum subspecies animalis 7-1 bacteriophage PHIFunu1 and PHIFunu2", Anaerobe, 38;125-129 (2016).
Heinl, Stefan et al. "Insights into the completely annotated genome of *Lactobacillus buchneri* CD034, a strain isolated from stable grass silage", Journal of Biotechnology, 161:163-166 (2012).
International Search Report and Written Opinion for PCT/US2015/047136 dated Nov. 26, 2015, 10 pages.
Karvelis, Tautvydas et al., "crRNA and tracerRNK guide Cas9-mediated DNA interference in *Streptococcus thermophilus*," RNA Biology, 2013, vol. 10, Issue 5, pp. 841-851.
Karvelis, Tautvydas et al., "Programmable DNA cleavage in vitro by Cas9," Biochem. Soc. Trans. 2013, vol. 41, part 6. pp. 1401-1406.
Marcotte, H. et al. "Proteomes—*Lactobacillus gasseri* DSM 14869", NCBI Reference Sequence CP006803, (2013) URL: https://www.uniprot.org/proteomes/UP000217220, retrieved Jul. 20, 2018.
Nale Janet Y. et al., "Diverse temperate bacteriophage carriage in Clostridium difficile 027 strains", PloS One, 7(5) 1-9 (2012).

(56) References Cited

OTHER PUBLICATIONS

Rarnakrishna Suresh et al. "Gene disruption by cell-penetrating peptide-mediated delivery of Cas9 protein and guide RNA", Genome Research, 24;1020-1027 (2014).
Uchiyama Jumpei et al., "Characterization of Helicobacter pylori bacteriophage KHP30", Applied and environmental microbiology, 79(10):3176-3184 (2013).
Written Opinion of the International Search Report regarding International Application No. PCT/US2016/067657, dated Mar. 6, 2017, 9 pages.
Office Action, U.S. Appl. No. 15/032,985, dated Feb. 5, 2019, 11 pages.
Rath D et al. The CRISPR-Cas immune system: Biology, mechanisms and applications. Biochimie. 2015;117:119-128.
Spath K et al. Lactobacillus plantarum and Lactobacillus buchneri as expression systems: Evaluation of different origins of replication for the design of suitable shuttle vectors. Mol. Biotechnol. 2012; 52: 40-48.
Grissa I et al. The CRISPRdb database and tools to display CRISPRs and to generate dictionaries of spacers and repeats. BMC Bioinformatics. 2007; 8(172): pp. 1-10.
Anderson et al. "*Lactobacillus gasseri* CRISPR-Cas9 characterization In Vitro reveals a flexible mode of protospacer-adjacent motif recognition" PLOS ONE, 13(2) 14 pages 2018.
Gasiunas et al, "Molecular mechanisms of CRISPR-mediated microbial immunity" Cellular and Molecular Life Sciences, 71:449-465 (2014).
GenBank Accession No. FN692037.1, "*Lactobacillus crispatus* ST1 complete genome, strain ST1" Feb. 27, 2015.
Hidalgo-Cantabrana et al. "Genome editing using the endogenous type I CRISPR-Cas system in *Lactobacillus crispatus*" PNAS, 116)32):15774-15783 (2019).
International Preliminary Report on Patentability Notification, PCT/US2018/034322, dated Dec. 5, 2019, 7 pages.
Internetional Search Report and Written Opinion corresponding to PCT/US2019/52883. dated Dec. 23, 2019, 9 pages.
International Search Report and Written Opinion corresponding to PCT/US2019/52878, dated Dec. 27, 2019, 14 pages.
International Search Report and Written Opinion corresponding to PCT /US2019/52864, dated Dec. 17, 2019, 15 pages.
International Search Report and Written Opinion corresponding to PCT/US2019/52861, dated Feb. 12, 2020. 18 pages.
Ojala et al. "Comparative genomics of *Lactobacillus crispatus* suggests novel mechanisms for the competitive exclusion of Garnerella vaginalis", BNC Genomics, 15:1070 (2014).
Sanozky-Dawes et al. "Occurrence and activity a type II CRISPR-Cas system in *Lactobacillus gasseri*" MIcrobiolcay, 161:1762-1761 2015.
Westra et al. "CRISPR Immunity Relies on the Consecutive Binding and Degradation of Negatively Supercoiled invader DNA by Cascade and Cas3" Molecular Cell. 46:595-605 (2012).
Yosef et al. "High-temperature protein G is essenbal for activity of the *Escherichia coli* clustered regularly interspaced short palindromic, repeats (CRISPR)/Cas system" Proc Natl Acad Sci. 108(50):20136-20141 (2011).
Barrangou R. "CRISPR-Cas systems and RNA-guided interference", *Wiley interdisciplinary reviews, RNA* (2013)4: pp. 267-278.
Barrangou R., et al. "CRISPR: new horizons in phage resistance and strain identification" *Annu Rev Food Sci Technol* (2012) 3, pp. 143-162.
Barrangou R., et al. "CRISPR-Cas systems: prokaryotes upgrade to adaptive immunity", *Mol Cell* (2014) 54(2): pp. 234-244.
Barrangou, R. "Diversity of CRISPR-Cas immune systems and molecular machines", *Genome Biology* (2015) 16:247, 11 pages.
Barrangou, R., et al. "CRISPR provides acquired resistance against viruses in prokaryotes", *Science* (2007) 315(5819): pp. 1709-1712.
Bhaya et al. "CRISPR-Cas Systems in Bacteria and Archaea: Versatile Small RNAs for Adaptive Defense and Regulation", *Annu. Rev. Genet.* (2011) 45: pp. 273-297.

Bikard D. et al. "Programmable repression and activation of bacterial gene expression using an engineered CRISPR-Cas system" *Nucleic Acids Res* (2013) 41(15): pp, 7429-7437.
Bikard D., et al. "CRISPR interference can prevent natural transformation and virulence acquisition during in vivo bacterial infection", *Cell Host & Microbe* (2012), 10 pages.
Bikard D., et al. "Exploiting CRISPR-Cas nucleases to produce sequence-specific antimicrobial", *Nature Biotechnology* 2014, 6 pages.
Briner AE, Barrangou R. "*Lactobacillus buchneri* Genotyping on the Basis of Clustered Regularly Interspaced Short Palindromic Repeat (CRISPR) Locus Diversity", *Appl Environ Microbial.* 80:994-1001, (2014).
Briner at al. "Guide RNA Functional Modules Direct Cas9 Activity and Orthogonality", *Molecular Cell.* (2014) 56(2): pp. 333-339.
Brouns SJJ, et al. "Small CRISPR RNAs guide antiviral defense in prokaryotes", *Science* 2008) 321:5891, pp. 960-964.
Carte et al. "The three major types of CRISPR-Cas systems function independently in CRISPR RNA biogenesis in *Streptococcus thermophilus* ", *Molecular Microbiology*, 93(1), pp. 98-112 (2014).
Chylinski et al. "Classification and evolution of type ll CRiSPR-Cas Systems", *Nucleic Acids Research*, (2014) 15 pages.
Chylinski Krzysztof et al., "The tracrRNA and Cas9 families of type II CRISPR-Cas immunity systems", *RNA biology*, 10:5, 13 pages (2013).
Citorik R., et al. "Sequence-specific antimicrobials using efficiently delivered RNA-guided nucleases", *Nature Biotechnology* 2014, 7 pages.
Cong et al. "Multiplex Genome Engineering Using CRISPR/Cas Systems" *Science* (2013) vol. 339 (6121): pp. 819-823.
Darmon E, Leach DF "Bacterial Genome Instability", *Microbioi. Mol. Biol. Rev.* (2014) vol. 78, pp. 1-39.
Deltcheva, E. et al. "CRISPR RNA maturation by *trans*-encoded small RNA and host factor RNase III", *Nature*, vol. 471, (Mar. 2011) pp. 602-607.
Doench et al. "Rational design of highly active sgRNAs for CRISPR-Cas9—mediated gene inactivation", *Nature Biotechnology*, 32:12 (2014) 8 pages.
Dupuis Me et al., "CRISPR-Cas and restriction-modification systems are compatible and increase phage resistance", *Nat Commun.*, vol. 4, p. 2087 (2013).
Edgar R., et al. "The *Escherichia coli* CRISPR System Protects from Lysogenization, Lysogens, and Prophage Induction", *Journal of Bacteriotogy* (2010), vol. 192, No. 23, pp. 6292-6294.
Estvelt et al. "Orthogonal Cas9 proteins for RNA-guided gene regulation and editing", *Nature Methods*, 10:11 (2013) pp. 1116-1121.
Fonfara, I. at al. "Phylogeny of Cas9 determines functional exchangeability of dual-RNA and Cas9 among orthologous type II CRISPR-Cas systems", *Nucleic Acids Res* (2013) 14 pages.
Fu et al. "Improving CRISPR-Cas nuclease specificity using truncated guide RNAs", *Nature Biotechnology*, 32:3 (2013) 9 pages.
Garneau Je, et al. "The CRISPR/Cas bacterial immune system cleaves bacteriophage and plasmid DNA" *Nature* (2010) 468(7320): pp. 67-71.
Gasiunas et al. "Cas9-crRNA ribonucleoprotein complex mediates specific DNA cleavage for adaptive immunity in bacteria" *Proc. Natl. Acad. Sci.* (2012), 109:E2579-E2586.
Gilbert et al. "Genome-Scale CRISPR-Mediated Control of Gene Repression and Activation", *Cell*, 159 (2014) pp. 647-661.
Gilbert, L. A. et al. "CRISPR-Mediated Modular RNA-Guided Regulation of Transcription in Eukaryotes", *Cell 154*, (2013) pp. 442-451.
Gomaa AA, et al. "Programmable Removal of Bacterial Strains by Use of Genome-Targeting CRISPR-Cas Systems", *mBio* (2014), 5(1):e00928-13.
Haurwitz et al. "Sequence—and Structure-Specific RNA Processing by a CRISPR Endonuolease", *Science* (2010) 329: pp. 1355-1358.
Horvath and Barrangou "CRISPR/Cas, the Immune System of Bacteria and Archaea", *Science* (2010) 327, pp. 167-170.
Horvath, P. et al. "Diversity, Activity, and Evolution of CRISPR Loci in *Streptococcus thermophilus* ", *J Bacterial.* 190 (2008) pp. 1401-1412.

(56) References Cited

OTHER PUBLICATIONS

Hsu et al. "DNA targeting specificity of RNA-guided Cas9 nucleases", *Nature Biotechnology*, 31:9 (2013) pp. 827-834.

Jiang, W. et al. "Dealing with the Evolutionary Downside of CRISPR Immunity: Bacteria and Beneficial Plasmids", *PLOS Genetics* (2013) vol. 9, issue 9, 13 pages.

Jiang, W. et al. "RNA-guided editing of bacterial genomes using CRISPR-Cas systems", *Nat. Biotechnol.* (2013) vol. 31, pp. 233-239.

Jinek et al. "A Programmable Dual-RNA—Guided DNA Endonuclease in Adaptive Bacterial Immunity", *Science* (2012) vol. 337, pp. 816-821.

Jinek, M. et al., "Structures of Cas9 endonucleases reveal RNA-mediated conformational activation", *Science* (2014) vol. 343, 6176, 28 pages.

Karvelis et al. "crRNA and tracrRNA guide Cas9-mediated DNA interference in *Streptococcus thermophilus*", *RNA Biol.* (2013) vol. 10: pp. 841-851.

Kobayashi K, et ai. "Essential *Bacillus subtilis* genes", *Proc. Natl. Aced. Sci.* U.S.A. (2003) vol. 100, pp. 4678-4683.

Labrie SJ et al. "Bacteriophage resistance mechanisms" *Nat. Rev. Microbial* (2010) vol. 8, pp. 317-327.

Luo, M. et at., "Repurposing endogenous type I CRISPR-Cas systems for programmable gene repression", *Nucleic Acid Research* (2014) 8 pages.

Magadan et al. "Cleavage of Phage DNA by the *Streptococcus thermophilus* CRISPR3-Cas System", *PLoS One* (2012) 7:e40913. 8 pages.

Mahillon J. et al. "Insertion sequences", *Microbial Mol Biol Rev* (1998) vol. 62(3): pp. 725-774.

Makarova and Koonin "Annotation and Classification of CRISPR-Cas Systems", *Methods Mol Biol.* (2015), 1311: pp. 47-75.

Makarova et al. "An updated evolutionary classification of CRISPR—Cas systems", *Nat Rev Microbial.* 13:722-736 (2015), 15 pages.

Makarova et al. "Unification of Cas protein families and a simple scenario for the origin and evolution of CRISPRCas systems", *Biol Direct.* (2011) vol. 6:38, 27 pages.

Makarova, K. S. et al. "Evolution and classification of the CRISPR-Cas systems"; *Nat Rev Microbial* (2011) vol. 9, pp. 467-477.

Marraffini end Sontheimer "CRISPR Interference Limits Horizontal Gene Transfer in Staphylococci by Targeting DNA", *Science* (2008) vol. 322: pp. 1843-1845.

Mojica, F. et al. "Short motif sequences determine the targets of the prokaryotic CRISPR defence system", *Microbiology* (2009) vol. 155. 8 pages.

Nishimasu, H., et al. "Crystal Structure of Cas9 in Complex with Guide RNA and Target DNA", *Cell* (2014) vol. 156, pp. 935-949.

Notification of International Preliminary Report on Patentability corresponding to International Application No. PCT/IB2015/052515; dated Oct. 12, 2016, 7 pages.

Notification and Transmittal of International Search Report and Written Opinion of the International Searching Authority for international Application No. PCT/IB2015/052515; dated Oct. 10, 2015; 12 pages.

Notification of Transmittal of the International Search Report and the Written Opinion of the International Searching Authority, or the Declaration, PCT/US2016/034812, dated Sep. 15, 2016, 9 pages.

Novagen "pCDF-1b Vector" Sep. 10; 2003, Retrieved from the Internet on Sep. 1, 2015, at http://www.helmhoitz-muenchen.de/fieadmin/PEPF/pCDF_vectors/pCDF-1b_map.pdf, 2 pages.

Oh JH and van Pijkeren JP "CRISPR-Cas9-assisted recombineering in *Lactobacillus reuteri*", *Nucleic Acids Res* (2014) vol. 10.1093/nar/gku623.

Qi, L. S. et al. "Repurposing CRISPR as an RNA-Guided Platform for Sequence-Specific Control of Gene Expression", *Cell* 152, 1173-1183 (2013), 11 pages.

Sander JD, and Joung JK. "CRISPR-Cas systems for editing, regulating and targeting genomes", *Nat. Biotechnol.* (2014) vol. 32, pp. 347-355.

Sapranauskas et al. "The *Streptococcus thermophilus* CRISPR/Cas system provides immunity in *Escherichia coli*", *Nucleic Acid Res.* (2011) vol. 39: pp. 9275-9282.

Seed Kimberley D. et al., "A bacteriophage encodes its own CRISPR/Cas adaptive response to evade host innate immunity", *Nature*, 494:7438, pp. 489-491 (2013).

Salle K, Barrangou R. "Harnessing CRISPR—Cas systems for bacterial genome editing", *Cell Press: Trends Microbial.* (2015) vol. 23(4). pp. 225-232.

Selle, K. et al. "CRISPR-based screening of genomic island excision events in bacteria", *Proc. Natl Aced Sci USA*, (2015); 112(26): pp. 8076-8081.

Salle, K. et al., "CRISPR-Based Technologies and the Future of Food Science", *Journal of Food Science* (2015) vol. 80; 6 pages.

Semenova et al. "Interference by clustered regularly interspaced short palindromic repeat (CRISPR) RNA is governed by a seed sequence", *PNAS*, 108:25 (2011) 6 pages.

Sinkuna, T. et al. "In vitro reconstitution of Cascade-mediated CRISPR immunity in *Streptococcus thermophilus*", *The EMBO Journal* (2013) vol. 32, pp. 385-394.

Stern, A. et al., "Self-targeting by CRISPR: gene regulation or autoimmunity", *Cell Press: Trends in Genetics*, (2010) vol. 26, No. 8, 6 pages.

Sternberg et al. "DNA interrogation by the CRISPR RNA-gulded endonuclease Cas9", *Nature*, vol. 507, (2014) 17 pages.

Terns and Terns "CRISPR-based adaptive immune systems", *Curr. Opin. Microbial.* (2011) vol 14: pp. 321-327.

Vercoe RB, et al. "Cytotoxic chromosomal targeting by CRISPR/Cas systems can reshape bacterial genomes and expel or remodel pathogenicity islands", *PLoS Genet* (2013) vol. 9(4):e1003454.

Westra et al. "The CRISPRs. They are A-Changin': How Prokaryotes Generate Adaptive Immunity", *Annu. Rev. Genet.* (2012) vol. 46: pp. 311-339.

Wiedenheft et al. "RNA-guided complex from a bacterial immune system enhances target recognition through seed sequence interactions", *PNAS*, 108:36 (2011) 7 pages.

Written Opinion and International Search Report corresponding to International Application No. PCT/US2016/037493, dated Sep. 15, 2016, 8 pages.

Lido et al. "The CRISPR RNA-guided surveillance complex in *Escherichia coli* accommodates extended RNA Spacers" Nucleic Acids Research, 44(15):7385-7394 2016.

Final Office Action, U.S. Appl. No. 16/153.052, dated Dec. 26, 2018. 14 pages.

Final Office Action, U.S. Appl. No. 15/507,176, dated Jan. 16, 2019, 19 pages.

Claesson MJ et al. NCBI reference sequence NC_007929, direct submission Dec. 16, 2005, p. 1 (2005).

Cong et al. Supplementary Materials for "Multiplex Genome Engineering Using CRISPR/Cas Systems" Science (2013) vol. 339 (6121): pp. 819-823.

Luo et al. "The CRISPR RNA-guided surveillance complex in *Escherichia coli* accommodates extended RNA Spacers" Nucleic Acids Research, 44(15):7385-7394 2016.

Gutierrez et al. "Predicting CRISPR-Cas9 activity in *E. coli*" bioRxviv, https://doi.org/10.1101/308148, pp. 1-22 2018.

Hochstrassera et al. "CasA mediates Cas3-catalyzed target degradation during CRISPR RNA-guided interference" PNAS, 111(18):6618-23 2014.

Nizet et al. "Bacterial sepsis and meningitis" Remington and Klein's Infectious diseases of the fetus and newborn infant, 8th Edition, pp. 217-271 2011.

Verco et al. "Cytotoxic Chromosomal Targeting by CRISPR/Cas Systems Can Reshape Bacterial Genomes and Expel or Remodel Pathogenicity Islands" PLOS Genetics, 9(4):1-13 2013.

Shah, S. A. et al. "Protospacer recognition motifs: Mixed identities and functional diversity" RNA Biology, 10(5):891-899 (2013).

Wallace, R. A. et al. "A CRISPR with Roles in Myxococcus xanthus Development and Exopolysaccharide Production" Journal of Bacteriology, 196(23):4036-4043 (2014).

Chauthaiwale, V. M. et al. "Bacteriophage Lamda as a Cloning Vector" Microbiological Reviews, 56(4):577-591 (1992).

(56) References Cited

OTHER PUBLICATIONS

Dang, Y. et al. "Optimizing sgRNA structure to improve CRISPR-Cas9 knockout efficiency" Genome Biology, 16(280):1-10 (2015).

Edgar, R. et al. "Reversing Bacterial Resistance to Antibiotics by Phage-Mediated Delivery of Dominant Sensitive Genes" Applied and Environmental Microbiology, 78(3):744-751 (2011).

Extended European Search Report corresponding to European Patent Application No. 18806333.3 (8 pages) (dated Feb. 9, 2021).

Third Party Observation filed in European Patent Application No. 16804164.8 on Feb. 19, 2021, 15 pages.

Third Party Observation filed in European Patent Application No. 16812275.2 on Feb. 19, 2021, 38 pages.

Yosef, I. et al. "Temperate and lytic bacteriophages programmed to sensitize and kill antibiotic-resistant bacteria" PNAS, 112(23):7267-7272 (2015).

R. Edgar and U. Qimron, "The *Escherichia coli* CRISPR system protects from lysogenization, lysogens, and prophage induction," Journal of Bacteriology 192(23):6291-6294 (Oct. 1, 2010).†

A.A. Gomaa et al., "Programmable removal of bacterial strains by use of genome-targeting CRISPR-Cas systems," mbio 5(1):e00928-13 (Jan. 28, 2014).†

R.B. Vercoe et al. "Cytotoxic chromosomal targeting by CRISPR/Cas systems can reshape bacterial genomes and expel or remodel pathogenicity islands," PLOS Genetics 9(4):e1003454 (Apr. 18, 2013).†

S.J.J. Brouns et al., "Small CRISPR RNAs guide antiviral defense in prokaryotes," Science 321 (5891):960-964 (Aug. 15, 2008).†

I. Yosef et al., "High-temperature protein G is essential for activity of the *Escherichia coli* clustered regularly interspaced short palindromic repeats (CRISPR)/Cas system," Proceedings of the National Academy of Science USA 108(50):20136-20141 (Nov. 23, 2011).†

\* cited by examiner
† cited by third party

METHODS AND COMPOSITIONS FOR EFFICIENT DELIVERY OF NUCLEIC ACIDS AND RNA-BASED ANTIMICROBIALS

STATEMENT OF PRIORITY

This application is a 35 U.S.C. § 371 national phase application of International Application Serial No. PCT/US2016/037493, flied Jun. 15, 2016, which claims the benefit, under 35 U.S.C. § 119 (a) of U.S. Provisional Patent Application No. 62/175,749, filed Jun. 15, 2015, the entire contents of each of which are incorporated by reference herein.

STATEMENT OF FEDERAL SUPPORT

This invention was made with government support under Grant No. MCB-1452902 awarded by the National Science Foundation. The government has certain rights in this invention.

FIELD OF THE INVENTION

The invention relates to the methods and compositions for modifying the methylation pattern of bacteriophage DNA and phagemid DNA. The invention further relates to methods and compositions for selective killing of bacteria using bacteriophages comprising bacteriophage DNA or phagemid DNA comprising components of an engineered CRISPR-Cas system.

BACKGROUND OF THE INVENTION

Clustered Regularly Interspaced Short Palindromic Repeats (CRISPR), in combination with CRISPR-associated genes (cas) constitute the CRISPR-Cas system, which confers adaptive immunity in many bacteria and most archaea. CRISPR-mediated immunization occurs through the integration of DNA from invasive genetic elements such as plasmids and phages that can be used to thwart future infections by invaders containing the same sequence.

CRISPR-Cas systems consist of CRISPR arrays of short DNA "repeats" interspaced by hypervariable "spacer" sequences and a set of flanking cas genes. The system acts by providing adaptive immunity against invasive genetic elements such as phage and plasmids through the sequence-specific targeting and interference of foreign nucleic acids (Barrangou et al. 2007. Science. 315:1709-1712; Brouns et al. 2008. Science 321:960-4; Horvath and Barrangou. 2010. Science. 327:167-70; Marraffini and Sontheimer. 2008. Science. 322:1843-1845; Bhaya et al. 2011. Annu. Rev. Genet. 45:273-297; Terns and Terns. 2011. Curr. Opin. Microbiol. 14:321-327; Westra et al. 2012. Annu. Rev. Genet. 46:311-339; Barrangou R. 2013. RNA. 4:267-278). Typically, invasive DNA sequences are acquired as novel "spacers" (Barrangou et al. 2007. Science. 315:1709-1712), each paired with a CRISPR repeat and inserted as a novel repeat-spacer unit in the CRISPR locus. The "spacers" are acquired by the Cas1 and Cas2 proteins universal to all CRISPR-Cas systems (Makarova et al. 2011. Nature Rev. Microbiol. 9:467-477; Yosef et al. 2012. Nucleic Acids Res. 40:5569-5576), with involvement by the Cas4 protein in some systems (Plagens et al. 2012. J. Bact. 194: 2491-2500; Zhang et al. 2012. PLoS One 7:e47232). The resulting repeat-spacer array is transcribed as a long pre-CRISPR RNA (pre-crRNA) (Brouns et al. 2008. Science 321:960-4), which is processed into CRISPR RNAs (crRNAs) that drive sequence-specific recognition of DNA or RNA. Specifically, crRNAs guide nucleases towards complementary targets for sequence-specific nucleic acid cleavage mediated by Cas endonucleases (Garneau et al. 2010. Nature. 468:67-71; Haurwitz et al. 2010. Science. 329:1355-1358; Sapranauskas et al. 2011. Nucleic Acid Res. 39:9275-9282; Jinek et al. 2012. Science. 337:816-821; Gasiunas et al. 2012. Proc. Natl. Acad. Sci. 109:E2579-E2586; Magadan et al. 2012. PLoS One. 7:e40913; Karvelis et al. 2013. RNA Biol. 10:841-851).

These widespread systems occur in nearly half of bacteria (about 46%) and the large majority of archaea (about 90%). They are classified into six main types (Makarova et al. 2011. Nature Rev. Microbiol. 9:467-477; Makarova et al. 2013. Nucleic Acid Res. 41:4360-4377; Makarova et al. 2015. Nature Rev. Microbiol. 13:722-736; Shmakov et al. 2015. Mol. Cell. 60:385-397)) based on the cas gene content, organization and variation in the biochemical processes that drive crRNA biogenesis, as well as the Cas protein complexes that mediate target recognition and cleavage. In types I and III, the specialized Cas endonucleases process the pre-crRNAs, which then assemble into a large multi-Cas protein complex capable of recognizing and cleaving nucleic acids complementary to the crRNA. A different process is involved in Type II CRISPR-Cas systems. Here, the pre-crRNAs are processed by a mechanism in which a trans-activating crRNA (tracrRNA) hybridizes to repeat regions of the crRNA. The hybridized crRNA-tracrRNA are cleaved by RNase III and following a second event that removes the 5' end of each spacer, mature crRNAs are produced that remain associated with the both the tracrRNA and Cas9. The mature complex then locates a target dsDNA sequence ('protospacer' sequence) that is complementary to the spacer sequence in the complex and cuts both strands. Target recognition and cleavage by the complex in the type II system not only requires a sequence that is complementary between the spacer sequence on the crRNA-tracrRNA complex and the target 'protospacer' sequence (herein defined as the strand that is complementary to the spacer sequence) but also requires a protospacer adjacent motif (PAM) sequence located at the 5' end of the protospacer sequence. The exact PAM sequence that is required can vary between different type II systems.

The Type I systems are the most prevalent in bacteria and in archaea (Makarova et al. 2011. Nature Rev. Microbiol. 9:467-477) and target DNA (Brouns et al. 2008. Science 321:960-4). A complex of 3 to 8 Cas proteins called the CRISPR associated complex for antiviral defense (Cascade) process the pre-crRNAs (Brouns et al. 2008. Science 321: 960-4), retaining the crRNA to recognize DNA sequences called "protospacers" that are complementary to the spacer portion of the crRNA. Aside from complementarity between the crRNA spacer and the protospacer, targeting requires a protospacer-adjacent motif (PAM) located at the 3' end of the protospacer (Mojica et al. 2009. Microbiology 155:733-740; Sorek et al. 2013. Ann. Rev. Biochem. 82:237-266). For Type I systems, the PAM is directly recognized by Cascade (Sashital et al. 2012. Mol. Cell 46:606-615; Westra et al. 2012. Mol. Cell 46:595-605). The exact PAM sequence that is required can vary between different Type I systems and can be identified through established bioinformatics and experimental procedures (Esvelt et al. 2013. Nat. Methods 10:1116-11121; Jiang et al. 2013. Nat. Biotechnol. 31:233-239; Mojica et al. 2009. Microbiology 155:733-740). Once a protospacer is recognized, Cascade generally recruits the endonuclease Cas3, which cleaves and degrades the target DNA (Sinkunas et al. 2011. *EMBO J.* 30:1335-1342; Sinkunas et al. 2013. *EMBO J.* 32:385-394).

Bacteriophages (or phages) are bacterial viruses that rely on the host's cellular machinery to replicate. Generally, phages generally fall into three categories: lytic, lysogenic, and temperate. Lytic bacteriophages infect a host cell, undergo numerous rounds of replication, and trigger cell lysis to release newly made bacteriophage particles. Lysogenic bacteriophages permanently reside within the host cell, either within the bacterial genome or as an extrachromosomal plasmid. Temperate bacteriophages are capable of being lytic or lysogenic, and choose one versus the other depending on growth conditions and the physiological state of the cell.

Phages have been used to package and deliver synthetic DNA dating back to the 1950's (Lennox, E.s., Virology 1(2):190-206(1950)). In this time, three general approaches have been adopted. Under the first approach, the synthetic DNA is randomly recombined into the bacteriophage genome, which usually involves a selectable marker. This approach was often used in the early days of phage work before the advent of modern molecular biology techniques. Under the second approach, restriction sites within the phage are used to introduce synthetic DNA in vitro. The *E. coli* lambda phage is a prime example, where a few commercial sources of lambda bacteriophages with incorporated restriction sites are available (Chauthaiwale et al. *Microbiol. Rev.* 56, 577-591 (1992)). Under the third approach, a plasmid generally encoding the phage packaging sites and lytic origin of replication is packaged as part of the assembly of the bacteriophage particle (Westwater et al. *Microbiol. Read. Engl.* 148, 943-950 (2002); Sternberg, N. *Proc. Natl. Acad. Sci. U.S.A.* 87, 103-107 (1990)). The resulting plasmids have been coined 'phagemids.' Phagemids have been primarily used to deliver individual genes or constructs, for example, to reprogram endogenous pathways or to induce cell death (Sternberg, N., *Proc. Natl. Acad. Sci. U.S.A.* 87, 103-107 (1990); Lu & Collins. *Proc. Natl. Acad. Sci. U.S.A.* 104, 11197-11202 (2007); Citorik et al. *Nat. Biotechnol.* (2014) 32(11):1141-1145; Bikard et al. *Nat. Biotechnol.* (2014) 32(11):1146-1150; Kittleson et al. *ACS Synth. Biol.* 1, 583-589 (2012)).

Most phages are limited to a given bacterial strain for evolutionary reasons. Injecting their genetic material into an incompatible strain would be counterproductive, so phages have evolved to specifically infect a limited cross-section of strains. However, some phages have been discovered that can inject their genetic material into a wide range of bacteria. The classic example is the P1 phage, which has been shown to inject DNA in a range of gram-negative bacteria—some well beyond its natural *E. coli* host (Westwater et al. *Microbiol. Read. Engl.* 148, 943-950 (2002); Kaiser & Dworkin. *Science* 187, 653-654 (1975); O'Connor et al. *J. Bacteria* 155, 317-329 (1983).

While phages such as P1 could provide generalized platforms for delivering synthetic DNA, they face a ubiquitous barrier: restriction-modification (R-M) systems. These bacterial defense systems consist of methylases (methyltransferases) that methylate DNA at specific sequences and/or restriction enzymes that cleave DNA that are unmethylated (Types I, II, III) or methylated (Type IV). When these systems encounter DNA with a foreign methylation pattern, the restriction enzymes cleave the DNA in multiple locations, limiting the potential for repair. Any of the foreign DNA that does undergoes methylation can escape the restriction enzymes, although the probability of this occurring is low. As most bacteria encode multiple R-M systems that generate distinct methylation patterns, introducing synthetic DNA into a random bacterium can pose a major challenge.

The present invention overcomes previous shortcomings in the art by providing methods for modifying the methylation of bacteriophage and phagemid DNA and methods and compositions for use of bacteriophage particles in delivery of genome targeting CRISPR-Cas systems.

SUMMARY OF THE INVENTION

In one aspect, a method of modifying the methylation pattern of a bacteriophage DNA or phagemid DNA, comprising: altering methylating activity of a production host bacterium, comprising: (1) disrupting the activity at least one enzyme of an endogenous restriction modification system (R-M system) of a production host bacterium, thereby producing a modified production host bacterium having the activity of at least one enzyme of the endogenous R-M system disrupted, and/or (2) introducing into a production host bacterium a polynucleotide encoding at least one heterologous methyltransferase, thereby producing a modified production host bacterium expressing the heterologous methyltransferase; infecting the modified production host bacterium having an altered methylating activity with a bacteriophage particle comprising bacteriophage DNA or phagemid DNA, thereby methylating said bacteriophage DNA or phagemid DNA; and producing a bacteriophage particle comprising bacteriophage DNA or phagemid DNA having a modified methylation pattern. In some aspects, the infecting step can be carried out prior the step of altering the methylating activity of the production host bacterium.

In another aspect, a method of modifying the methylation pattern of a bacteriophage DNA or phagemid DNA, comprising: infecting a production host bacterium with a bacteriophage particle comprising bacteriophage DNA or phagemid DNA, wherein the production host bacterium has altered methylating activity via disruption of at least one enzyme of an endogenous R-M system and/or expression of at least one heterologous methyltransferase, thereby methylating said bacteriophage DNA or phagemid DNA; and producing a bacteriophage particle comprising bacteriophage DNA or phagemid DNA having a modified methylation pattern.

In a further aspect, the invention provides a method of increasing the efficiency of introducing a heterologous nucleic acid of interest into a target host bacterium via bacteriophage, comprising: infecting a production host bacterium with a bacteriophage particle comprising bacteriophage DNA or phagemid DNA comprising at least one heterologous nucleic acid of interest, wherein the production host bacterium has altered methylating activity via disruption of at least one enzyme of an endogenous restriction modification system (R-M system) and/or expression of at least one heterologous methyltransferase, thereby methylating said bacteriophage DNA or phagemid DNA; producing a bacteriophage particle comprising bacteriophage DNA or phagemid DNA having a modified methylation pattern and comprising/encoding the at least one heterologous nucleic acid of interest; and infecting a target host bacterium with said bacteriophage particle, wherein the target host bacterium has a methylation pattern (or R-M system(s)) that is substantially similar to (i.e., compatible with) that of the production host bacterium, thereby increasing the efficiency of introducing said heterologous nucleic acid of interest into said target host bacteriophage.

In some aspects, a bacteriophage particle produced by the methods of the invention is provided. A further aspect of the invention provides a bacteriophage particle comprising bacteriophage DNA or phagemid DNA comprising a modified DNA methylation pattern that is substantially similar to a target host bacterium's restriction-modification system(s). In some aspects, at least one heterologous nucleic acid of interest is introduced into the bacteriophage DNA or the phagemid DNA prior to infection of the production host bacterium with the bacteriophage, thereby methylating the at least one heterologous nucleic acid of interest along with the bacteriophage DNA or the phagemid DNA. In additional aspects, the at least one heterologous nucleic acid of interest encodes a CRISPR array (e.g., a Type I or Type II CRISPR array). In further aspects, the at least one heterologous nucleic acid of interest encodes a recombinant Type I CRISPR-Cas system or a recombinant Type II CRISPR-Cas system.

An additional aspect of the invention provides a bacteriophage particle comprising bacteriophage DNA comprising a polynucleotide encoding a Type II CRISPR array. In a further aspect a bacteriophage particle is provided that comprises a bacteriophage DNA or phagemid DNA comprising a polynucleotide encoding a Type I CRISPR array.

Another aspect of the invention provides a bacteriophage particle comprising bacteriophage DNA or phagemid DNA, wherein the bacteriophage DNA or phagemid DNA comprises a recombinant Type II CRISPR-Cas system comprising: (a) a polynucleotide encoding a Cas9 polypeptide; (b) a polynucleotide encoding a CRISPR array; and c) a tracr nucleic acid, optionally wherein the polynucleotide encoding a CRISPR array and the tracr nucleic acid are fused to one another to form a single guide nucleic acid.

A further aspect of the invention provides a bacteriophage particle comprising bacteriophage DNA or phagemid DNA, wherein the bacteriophage DNA or phagemid DNA comprises a recombinant Type I CRISPR-Cas system comprising: (a) a polynucleotide encoding a CRISPR array; and (b) at least one polynucleotide encoding one or more Type I CRISPR polypeptides. In some aspects, Type I CRISPR polypeptides comprise Type I Cascade polypeptides, and a polynucleotide encoding a Cas3 polypeptide, or a Cas3' polypeptide and a Cas3" polypeptide.

In a further aspect, the Type I CRISPR array, the Type II CRISPR array, the Type I CRISPR-Cas system or the Type II CRISPR-Cas system, the polynucleotide encoding a Cas9 polypeptide, the tracr nucleic acid, and/or the at least one polynucleotide encoding one or more Type I CRISPR polypeptides are integrated into the bacteriophage DNA at a dispensable site or at a complemented site.

An additional aspect of the invention provides a method of selectively killing at least one target bacterial species or strain, comprising: contacting said at least one target bacterial species or strain with a bacteriophage particle of the invention, wherein the CRISPR array comprised in said bacteriophage DNA or phagemid DNA comprises at least one spacer having substantial complementarity to a target DNA in said at least one target bacterial species or strain. In some aspect of the invention, the bacteriophage particle is produced in a bacterial species or strain that is different from the target bacterial species or strain.

Further provided herein are bacteriophage particles, expression cassettes and cells comprising the recombinant nucleic acid molecules, CRISPR arrays, and/or heterologous polynucleotides of the invention.

These and other aspects of the invention are set forth in more detail in the description of the invention below.

BRIEF DESCRIPTION OF THE DRAWINGS

FIG. 2B shows dsDNA extracted from P1 bacteriophage particle when produced in a methyltransferase-positive strain of E. coli. Lane 1: VWR 2-log DNA ladder. Lanes 2, 4, 6: DNA from phage produced in dam+dcm+ E. coli. Lanes 3, 5, 7: DNA from phage produced in dcm−dam− E. coli. Lanes 2-3: DNA digested with AleI, NheI, and XhoI. Lanes 4-5: DNA digested with AleI, NheI, XhoI, and DpnII. Lanes 6-7: DNA digested with AleI, NheI, XhoI, and StyD41. DNA size markers are shown on the left.

FIG. 3A provides a schematic showing the introduction of synthetic DNA sequences into the P1 bacteriophage genome. IS1, and simABC are dispensable genes within the bacteriophage P1 genome and coi/imcB is a complementable genes that are needed only to trigger the lytic cycle. The coi/imcB functions can be compensated for by the inducible expression of the coi gene from a plasmid vector. FIG. 3B shows efficient delivery of the P1 genome in which the kan resistance gene is integrated into different sites (landing sites) in the phage genome.

FIG. 4A provides the experimental procedure for testing superinfection. Cells harboring either P1-ΔimcB/coi:kan$^R$ (LB001) or P1-ΔsimABC:kan$^R$ (LB002) were infected with phage P1-ΔimcB/coi:cm$^R$ and plated on kan, cm, and kan+cm plates. FIG. 4B shows the delivery efficiencies of P1-ΔimcB/coi:cm$^R$ in cells harboring either P1-ΔimcB/coi:kan$^R$ or P1-ΔsimABC:kan$^R$. * means no colonies detected.

FIG. 5A provides a schematic showing the packaging and delivery of the P1 genome or an engineered phagemid. FIG. 5B shows that P1 particles more efficiently package and deliver the P1 genome into E. coli MG1655 and BL21 than it does for a P1 phagemid.

FIG. 7A shows DNA delivery to E. coli using P1 bacteriophage having +/− DNA methylation (i.e., P1 produced in a bacterium that is either DNA methylation (+) or DNA methylation (−)). The number of infected E. coli cells as measured by CFUs grown under kanamycin selection was compared between strains and infections. FIG. 7B shows differences in DNA delivery to E. coli and Klebsiella pneumoniae by bacteriophage LB002 +/− methylation. LB002 infectious units, as measured by E. coli or K. pneumoniae CFUs grown under kanamycin selection, were then compared between infections. FIG. 7C shows DNA delivery to E. coli using M13 variant bacteriophage that are +/− DNA methylation.

The number of infected *E. coli* cells was then compared by strain. TOP10F': encodes dam and dcm but lacks restriction enzymes; EMG2: restriction-methylation systems are intact (will degrade unmethylated double-stranded DNA); JM110: does not encode dam and dcm and lacks restriction enzymes.

Figure 8A:
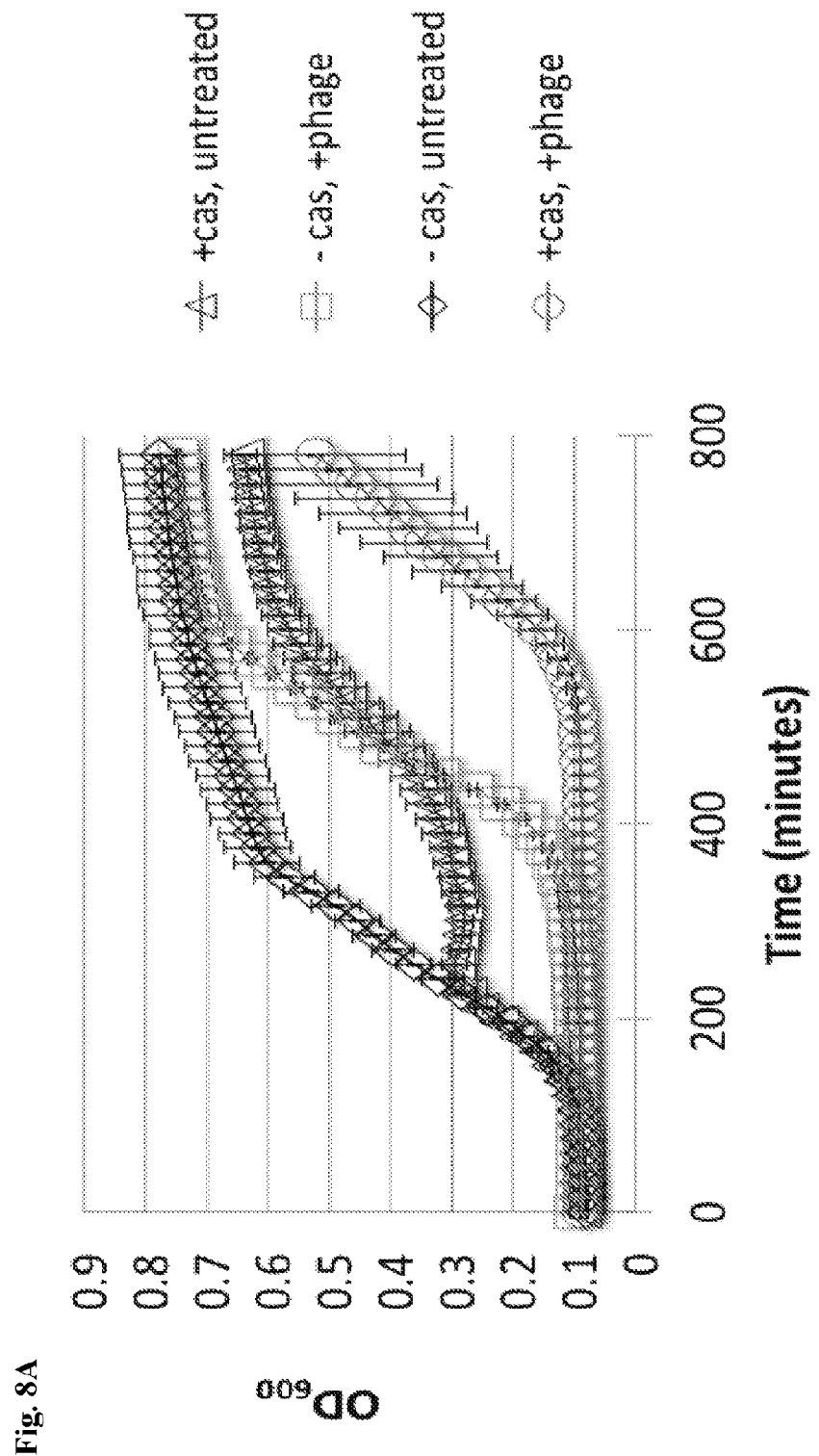
Figure 8B:
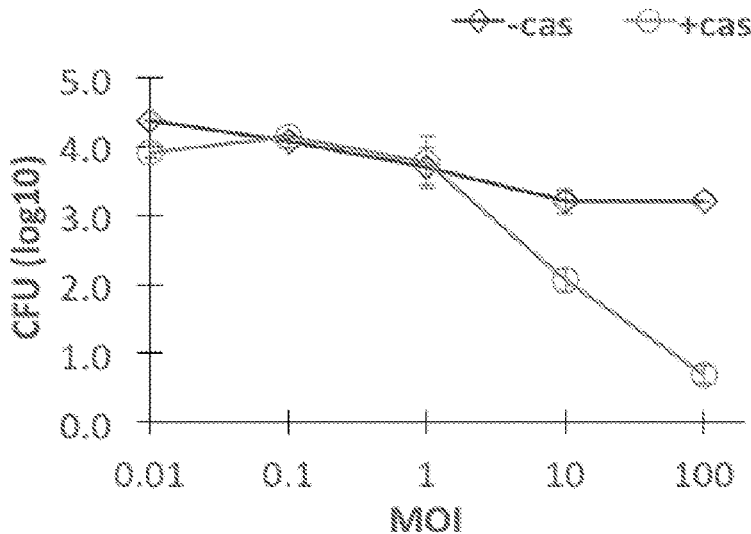
Figure 8C:
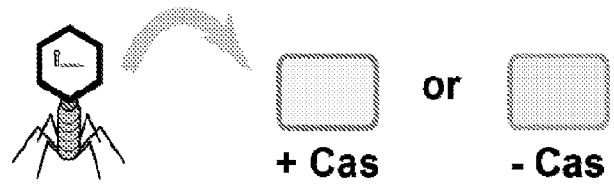
Figure 8C:
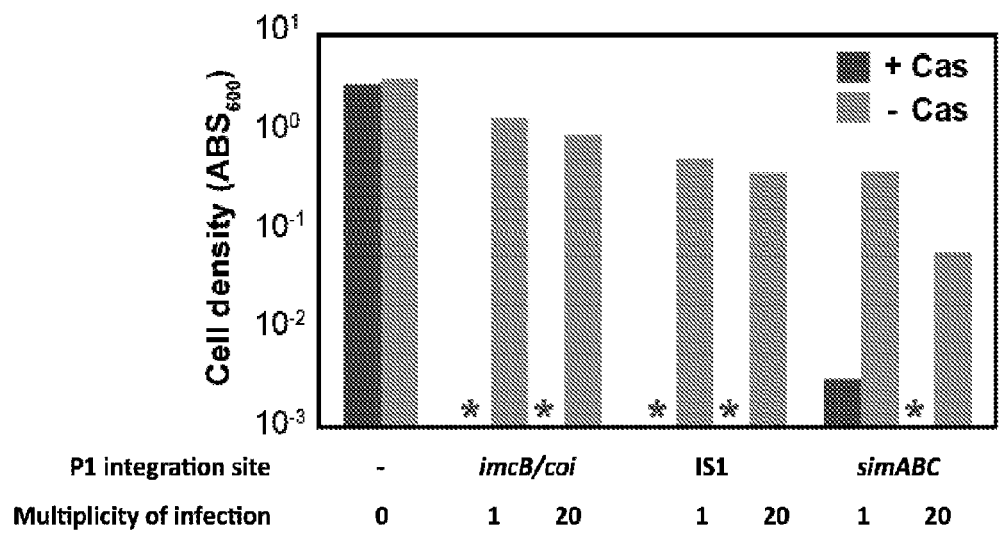
Figure 8D:
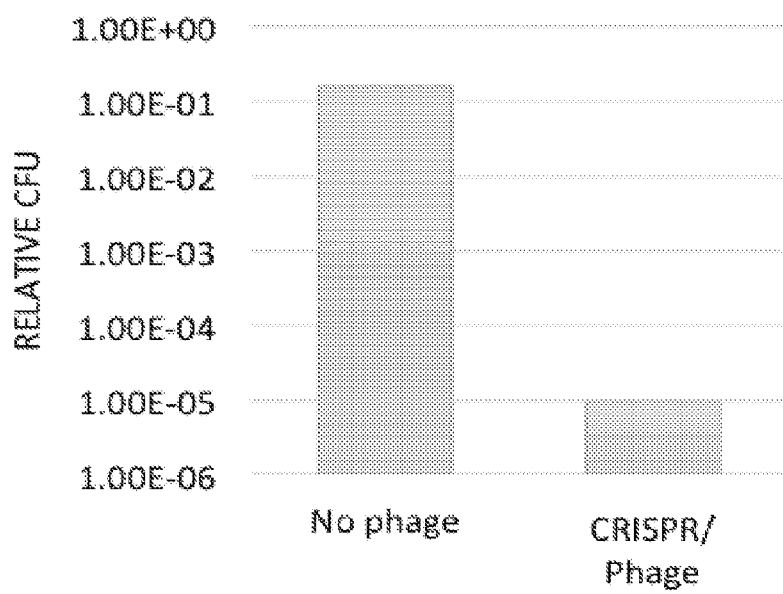

FIG. 8A shows that the Type I-E Cascade and Cas3 negatively affect growth following delivery of P1 that was equipped with a genome-targeting CRISPR RNA. Bacterial growth was measured by absorbance at a 600 nm (OD600). FIG. 8B shows Type I-E Cascade and Cas3 negatively affects survival following delivery of P1 equipped with a genome-targeting CRISPR RNA. The number of surviving bacterial cells at the different multiplicities of infection (MOIs) for each bacterial strain was then compared. FIG. 8C-8D show that delivering the P1 genome encoding a genome-targeting CRISPR RNA in different locations kills *E. coli* in the presence of the Type I-E Cascade and Cas3. FIG. 8C shows that CRISPR/phage treatment eliminates growth, and FIG. 8D shows that CRISPR/phage treatment during culture results in reduced viability.

Figure 9:
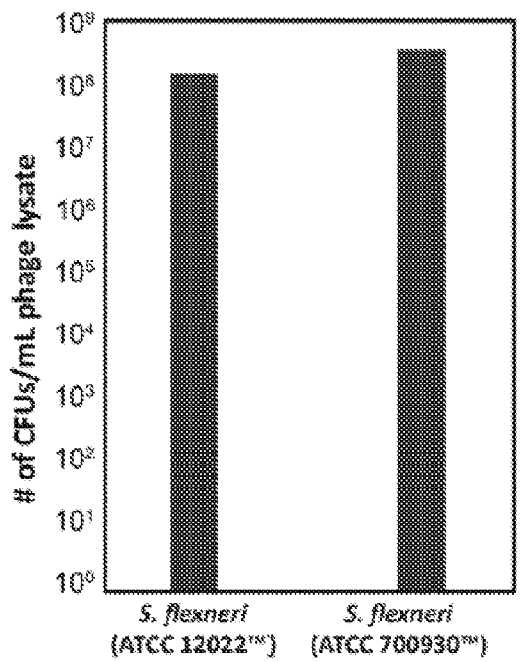

FIG. 9 shows efficient delivery of the bacteriophage P1 imcB-coi:kanR to two strains of *Shigella flexneri*.

Figure 10A:
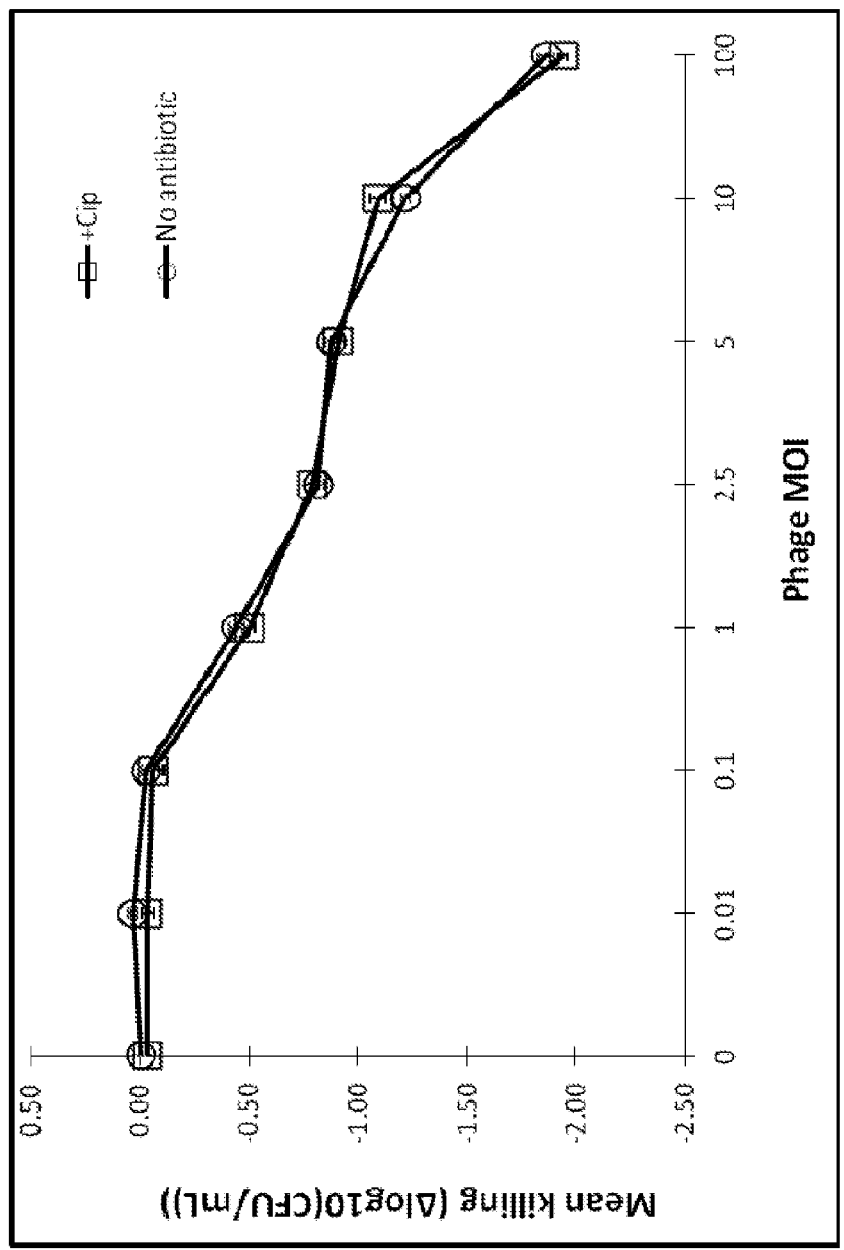
Figure 10B:
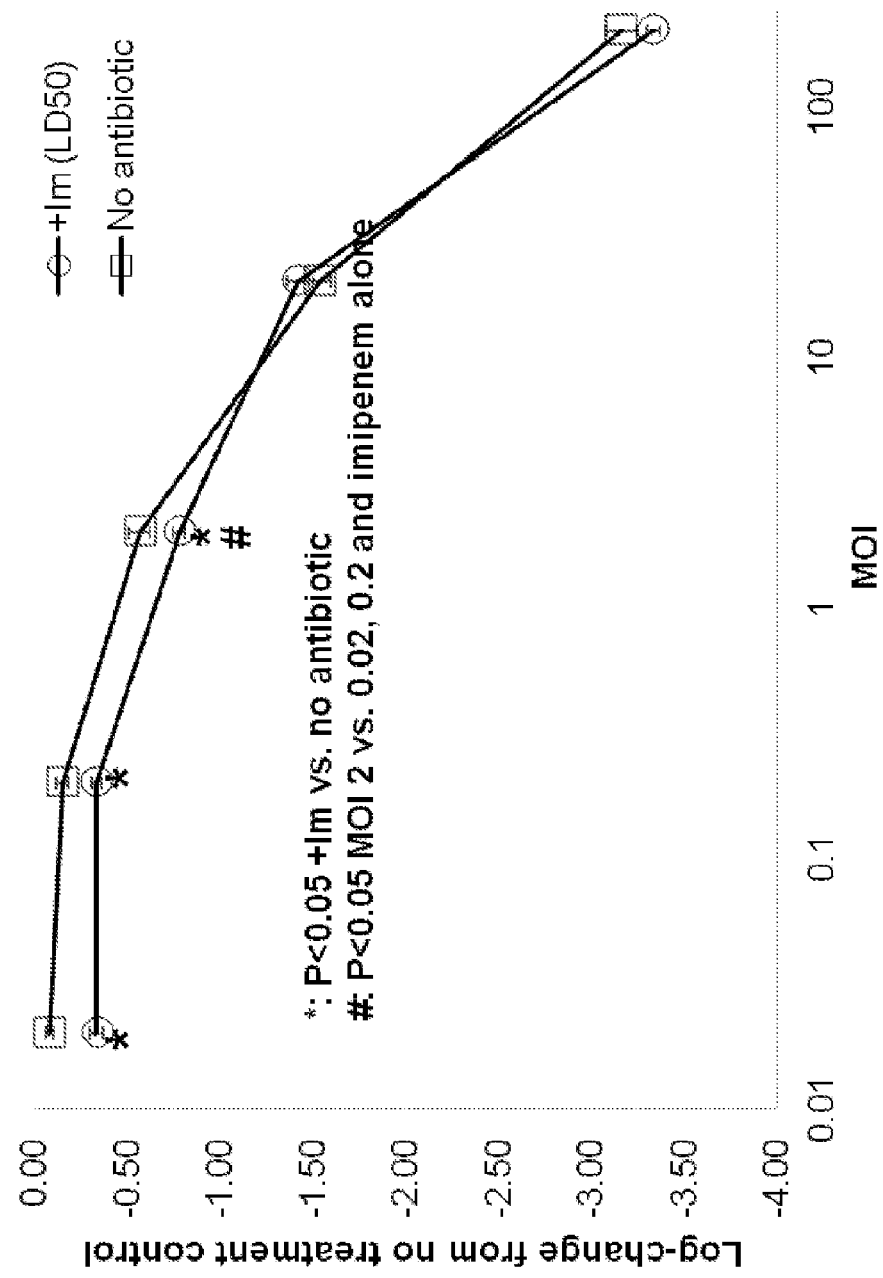
Figure 10C:
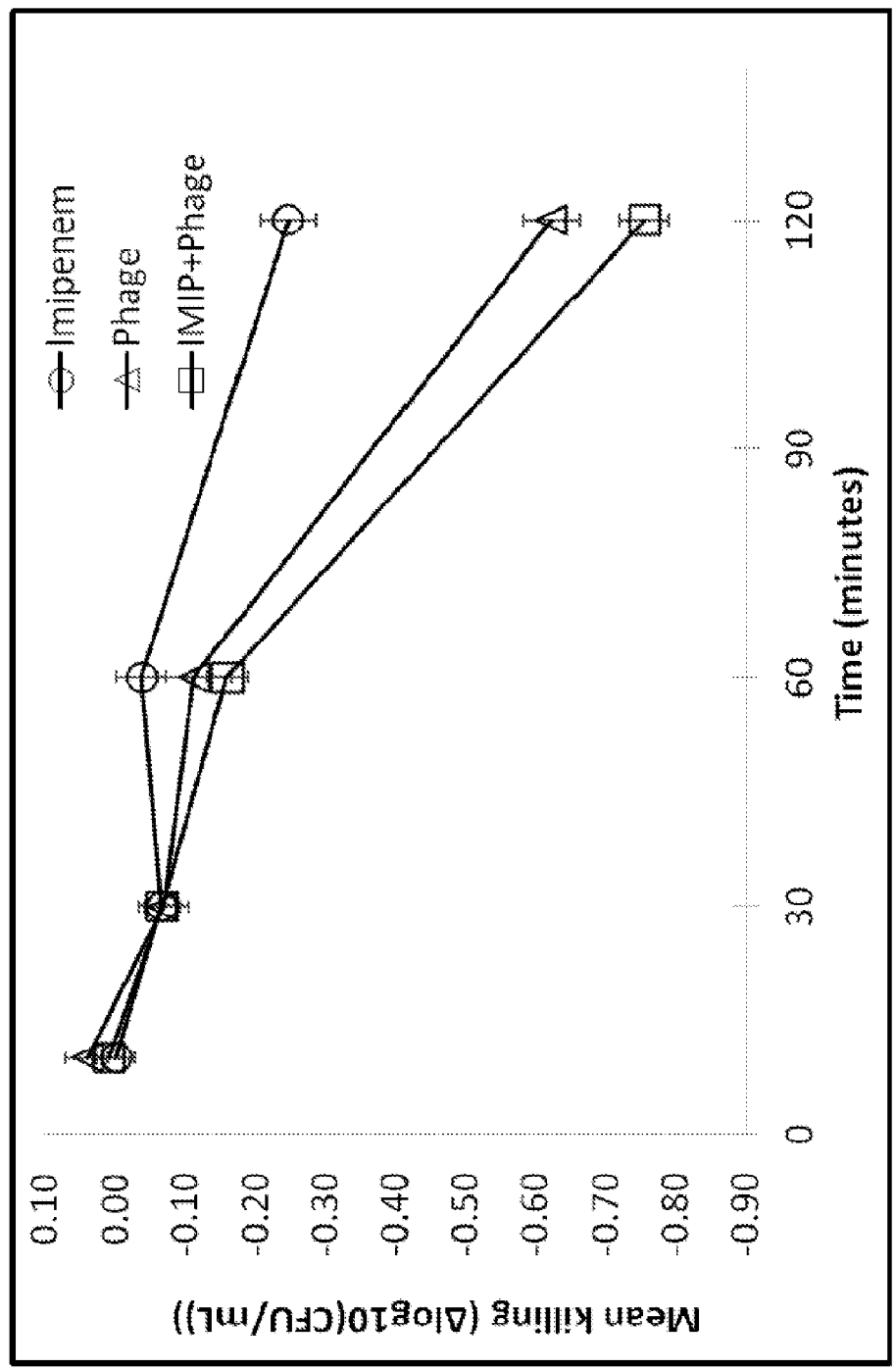

FIGS. 10A-10C. CRISPR phage (targeting ftsA) is demonstrated to kill antibiotic-resistant bacteria in FIG. 10A. Cip=Ciprofloxacin. FIG. 10B shows CRISPR phage exerts an additive antimicrobial effect when combined with effective antibiotics. IM=imipenem. FIG. 10C shows that CRISPR phage kills *E. coli* within 120 minutes with or without the presence of the antibiotic imipenem.

Figure 11A:
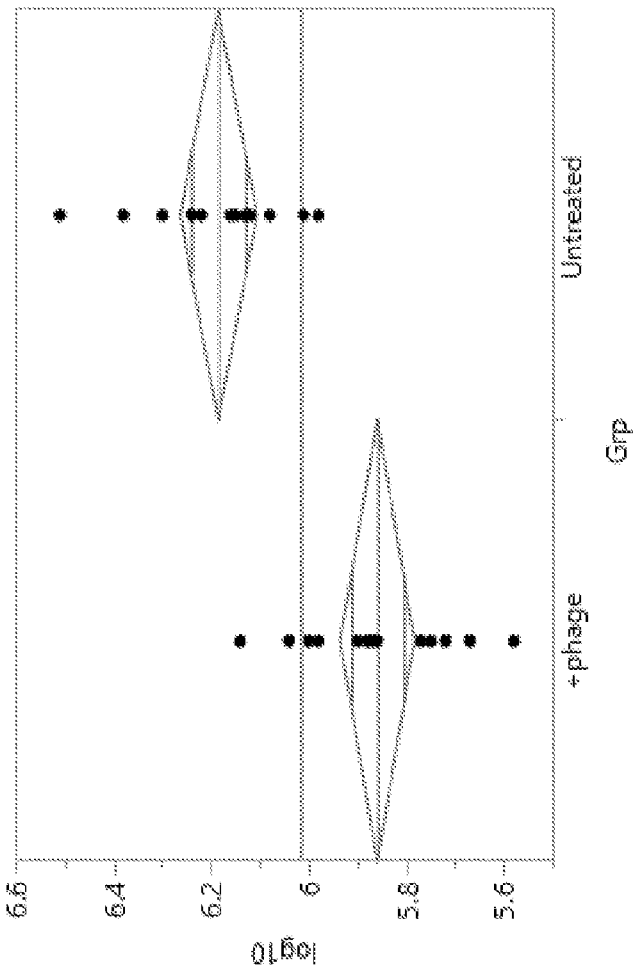
Figure 11B:
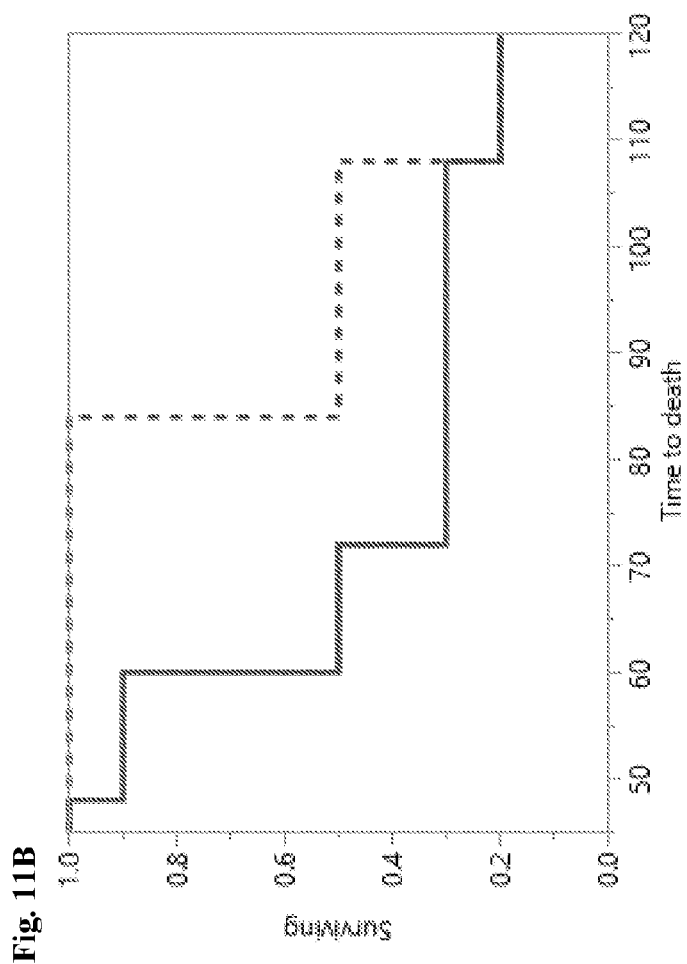

FIGS. 11A-11B show that CRISPR phage targeting *E. coli* decreases viable bacterial counts in a mouse model of thigh muscle infection (FIG. 11A) and that CRISPR phage targeting *E. coli* increases animal survival time in a mouse model (FIG. 11B).

Figure 12:
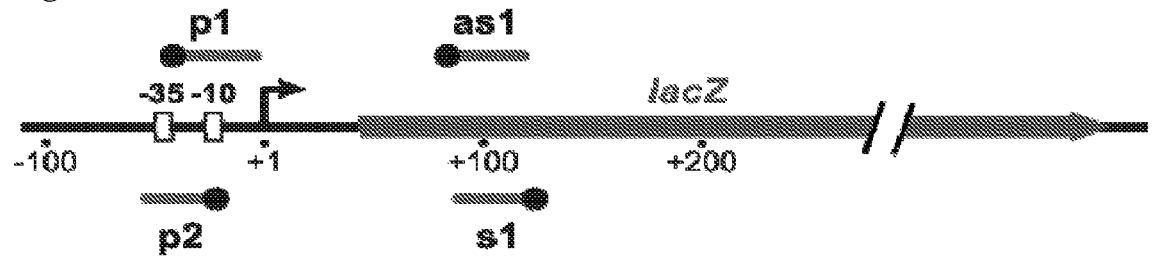
Figure 12:
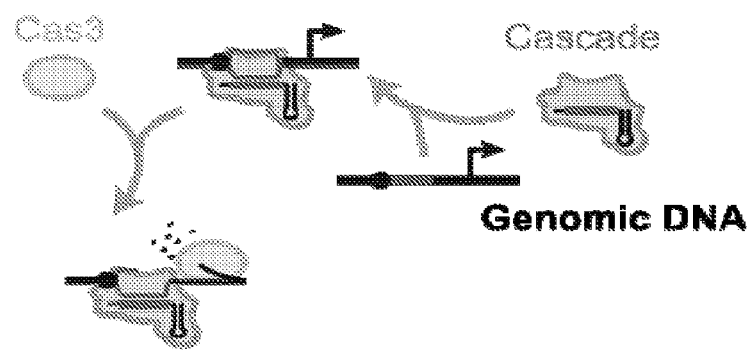
Figure 12:
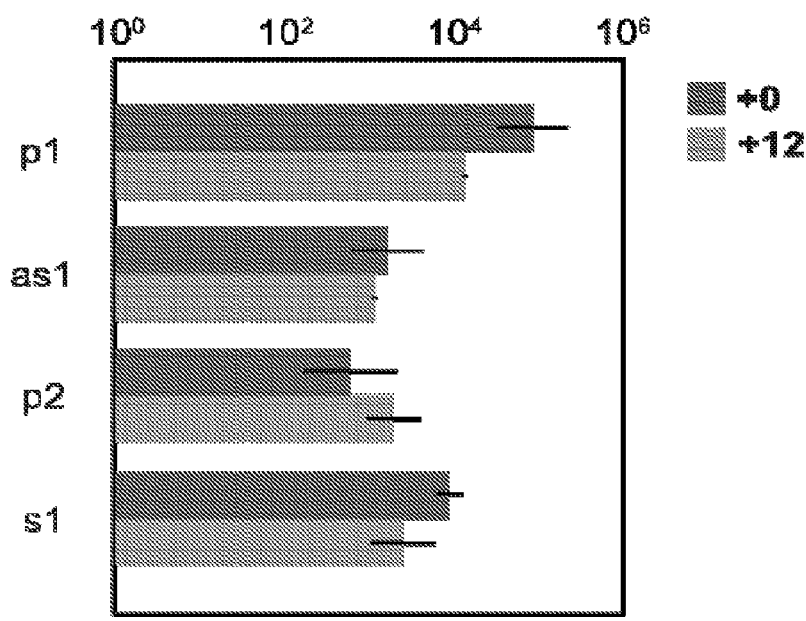

FIG. 12 shows extended CRISPR RNA spacers in the Type I-E system can elicit cell killing. Repeat-spacer-repeats (arrays) with spacers having lengths of 32 nts (+0) and 44 nts (+12) were tested, where the natural (wild-type) Type I-E system relies on spacers having a length of 32-nt. The spacers used (p1, as1, p2 and s1) targeted lacZ as shown in the schematic of the lacZ gene at the top of FIG. 12. A schematic of the DNA interference process is provided in the middle of FIG. 12 showing the spacer and Cascade complex binding to the genomic DNA and subsequent recruitment of Cas3. The bottom of FIG. 12 provides a graph showing transformation efficiency into *E. coli* MG1655 cells expressing the Type I-E proteins (Cas3, Cascade) for plasmids encoding each of the four spacers tested in relation to a non-targeting plasmid. The transformation efficiency is reported in relation to a plasmid encoding a non-targeting spacer.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, "chimeric" refers to a nucleic acid molecule or a polypeptide in which at least two components are derived from different sources (e.g., different organisms, different coding regions).

"Complement" as used herein can mean 100% complementarity or identity with the comparator nucleotide sequence or it can mean less than 100% complementarity (e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity). Complement or complementable may also be used in terms of a "complement" to or "complementing" a mutation. Thus, for example, a "complementable" site in a phage genome is a site comprising a gene that is essential for one aspect of phage function (e.g. lytic cycle), but this function can be restored by expressing the gene from a different position in the genome or on a plasmid.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, "contact," contacting," "contacted," and grammatical variations thereof, refers to placing the components of a desired reaction together under conditions suitable for carrying out the desired reaction (e.g., integration, transformation, screening, selecting, killing, identifying, amplifying, and the like). The methods and conditions for carrying out such reactions are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

A "fragment" or "portion" of a nucleotide sequence will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. In some embodiments, a fragment of a polynucleotide can be a functional fragment that encodes a polypeptide that retains its function (e.g., a fragment of a Type-I Cascade polypeptide that is reduce in length as compared to the wild type polypeptide but which retains at least one function of a Type-I Cascade polypeptide (e.g., process CRISPR RNAs, bind DNA and/or form a complex)). A functional fragment of a Cascade polypeptide may be encoded by a fragment of said Cascade polypeptide. In representative embodiments, the invention may comprise a functional fragment of a Cas9 nuclease. A Cas9 functional fragment retains one or more of the activities of a native Cas9 nuclease including, but not limited to, HNH nuclease activity, RuvC nuclease activity, DNA, RNA and/or PAM recognition and binding activities. A functional fragment of a Cas9 nuclease may be encoded by a fragment of a Cas9 polynucleotide.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5° and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "genome" as used herein includes an organism's chromosomal/nuclear genome as well as any mitochondrial, and/or plasmid genome.

A "hairpin sequence" as used herein, is a nucleotide sequence comprising hairpins (e.g., that forms one or more hairpin structures). A hairpin (e.g., stem-loop, fold-back) refers to a nucleic acid molecule having a secondary structure that includes a region of nucleotides that form a single strand that are further flanked on either side by a double stranded-region. Such structures are well known in the art. As known in the art, the double stranded region can comprise some mismatches in base pairing or can be perfectly complementary. In some embodiments, a repeat nucleotide sequence comprises, consists essentially of, consists of a hairpin sequence that is located within said repeat nucleotide sequence (i.e., at least one nucleotide (e.g., one, two, three, four, five, six, seven, eight, nine, ten, or more) of the repeat nucleotide sequence is present on either side of the hairpin that is within said repeat nucleotide sequence). In some embodiments, a hairpin sequence of a nucleic acid construct can be located at the 3'end of a tracr nucleic acid.

A "heterologous" or a "recombinant" nucleotide sequence is a nucleotide sequence not naturally associated with a host cell into which it is introduced, including non-naturally occurring multiple copies of a naturally occurring nucleotide sequence.

As used herein, a "heterologous methyltransferase" is a methyltransferase that is not naturally found in the bacterial host cell into which it is being introduced (e.g., production host bacterium). Thus, a "heterologous methyltransferase" that is introduced into a production host bacterium may be a methyltransferase from an archaeal species or from a bacterial strain or species that is different from methyltransferase(s) found in the production host bacterium.

A heterologous methyltransferase can be used to confer on a production host bacterium a similar methylation patters as that of a target strain. A non-limiting example of a DNA MTase useful with the invention includes LlaPI from phage Φ50, which can be introduced to protect against type II R-M systems in lactococci (Hill et al. *J Bacteria* 173(14):4363-70 (1991)). Additional DNA modification enzymes that can be expressed in a production host bacterium include those that encode polypeptides that acetimidate the adenine residues. Some R-M systems are sensitive to adenine methylation. Polypeptides that acetimidate the adenine residues in the bacteriophage DNA will protect the DNA against such systems. Non-limiting examples of polypeptides that can acetimidate adenine residues in the production host bacteria include the mom gene from phage Mu and the Mu-like prophage sequences (see, *Haemophilus influenzae* Rd (FluMu), *Neisseria meningitidis* type A strain Z2491 (Pnme1) and *H. influenzae* biotype *aegyptius* ATCC 11116), which converts adenine residues to N(6)-methyladenine, thereby protecting against adenine sensitive restriction enzymes. The methylation patterns conferred by individual methyltransferases can be assessed using established DNA sequencing technologies such as Pacbio SMRT sequencing (O'Loughlin et al. *PLoS One*. 2015:e0118533). Once generated, the production strain can be used to produce bacteriophage particles for DNA delivery into the target strain.

Bacterial "restriction-modification systems" (R-M systems) comprise (1) methyltransferases that methylate DNA at specific sequences and/or (2) restriction enzymes that cleave DNA that are unmethylated (Types I, II, and III) or methylated (Type IV). The R-M systems constitute a bacterial defense system wherein DNA with foreign methylation patterns is cleaved in multiple locations by the restriction enzymes of the R-M systems. Most bacteria comprise more than one R-M system. Roberts, R. J. et al. *Nucleic Acids Res*. 31, 1805-1812 (2003). Type I methyltransferases require the presence of a compatible specificity protein for functionality. Type II and type III methyltransferases do not require any additional proteins to function. Thus, methyltransferases and restriction enzymes useful with this invention (either as targets for modification or inhibition, or as heterologous polypeptides to be expressed in a production host bacterium, thereby modifying the R-M system of the production host bacterium) can include any methyltransferase or restriction enzyme comprised in a bacterial restriction-modification system (e.g., Type I, II, III, or IV).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention. Thus, for example, a homologue of a repeat, a tracr nucleic acid, a Cas9 polypeptide, a Cas3 polypeptide, a Cas3' polypeptide, a Cas3" polypeptide, and/or a Cascade polypeptide useful with this invention can be about 70% homologous or more to any known repeat, tracr nucleic acid, Cas9 polypeptide, Cas3 polypeptide, Cas3' polypeptide, Cas3" polypeptide, and/or Cascade polypeptide.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci*. 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control. Thus, for example, increased transcription of a target DNA can mean an increase in the transcription of the target gene of at least about 25%, 50%, 75%, 100%, 150%, 200%, 300%, 400%, 500% or more as compared to a control.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is a mRNA that is naturally occurring in or endogenous to the organism. A "homologous" nucleic acid is a nucleotide sequence naturally associated with a host cell into which it is introduced. Thus, for example, as used herein, the term "an endogenous restriction enzyme" means a restriction enzyme that is naturally occurring in (native to) the production host bacterium.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

A "synthetic" nucleic acid or polynucleotide, as used herein, refers to a nucleic acid or polynucleotide that is not found in nature but is constructed by the hand of man and as a consequence is not a product of nature.

As used herein, the term "polynucleotide" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "polynucleotide," "nucleotide sequence" "nucleic acid," "nucleic acid molecule," and "oligonucleotide" are also used interchangeably herein to refer to a heteropolymer of nucleotides. Except as otherwise indicated, nucleic acid molecules and/or polynucleotides provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "percent sequence identity" or "percent identity" refers to the percentage of identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences, CRISPR repeat-spacer-repeat sequences, and/or CRISPR arrays.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even less than about 5%) detectable activity or amount. Thus, for example, a mutation in a Cas3 nuclease or a Cas9 nuclease can reduce the nuclease activity of the Cas3 nuclease or the Cas9 nuclease by at least about 90%, 95%, 97%, 98%, 99%, or 100% as compared to a control (e.g., wild-type Cas3).

A "repeat sequence" as used herein, refers to, for example, any repeat sequence of a wild-type CRISPR locus or a repeat sequence of a synthetic CRISPR array that are separated by "spacer sequences" (e.g., a repeat-spacer-repeat sequence). A repeat sequence useful with this invention can be any known or later identified repeat sequence of a CRISPR locus or it can be a synthetic repeat designed to function in a CRISPR Type I system or a CRISPR Type II system. Thus, in some embodiments, a repeat sequence can be identical to or substantially identical to a repeat sequence from a wild-type CRISPR Type I loci or a wild-type CRISPR Type II loci. In some embodiments, a repeat sequence can comprise a portion of a wild type repeat sequence (e.g., 1, 2, 3, 4, 5, 6, 7, 8, 9, 10, 11, 12, 13, 14, 15 or more contiguous nucleotides of a wild type repeat sequence).

In some embodiments, a repeat sequence comprises, consists essentially of, or consists of at least one nucleotide (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, or more nucleotides, or any range therein). In other embodiments, a repeat sequence comprises, consists essentially of, or consists of at least about one to about 150 nucleotides. In still other embodiments, a repeat sequence comprises, consists essentially of, or consists of at least about one nucleotide to about 100 nucleotides, or any range or value therein. In further embodiments, a repeat sequence can comprise, consist essentially of, or consist of about 3 nucleotides to about 100 nucleotides, about 10 nucleotides to about 100 nucleotides, about 15 nucleotides to about 100 nucleotides, about 20 to about 50 nucleotides, about 20 to about 40 nucleotides, about 20 to about 30 nucleotides, about 30 to about 40 nucleotides, about 25 to about 40 nucleotides, about 25 to about 45 nucleotides, and/or about 25 to about 50 nucleotides, or any range or value therein. In representative embodiments, a repeat sequence can comprise, consist essentially of, or consist of about 25 nucleotides to about 38 nucleotides, or any range or value therein. In still further embodiments, a repeat sequence can comprise, consist essentially of, or consist of about 29 nucleotides. In yet further embodiments, the repeat sequence can comprise, consist essentially of, or consist of a hairpin only having at least about 20 to 30 nucleotides in length. In still other embodiments, a repeat sequence comprises, consists essentially of, or consists of at least about at least three nucleotides. When more than one spacer nucleotide sequence is present in a CRISPR array, each spacer nucleotide sequence is separated from another by "repeat nucleotide sequences." Thus, in some representative embodiments, a repeat sequence linked to the 5' end of a spacer sequence can be about three nucleotides in length (e.g., 3, 4, 5, 6, 7, 8, 9, 10 nucleotides or more) and have at least 90% identity (e.g., at least 90%, 91%, 92%, 93%, 94%, 95%, 96%, 97%, 98%, 99%, or more) to the same region (e.g., 5' end) of a wild type repeat nucleotide sequence. In other embodiments, the portion of a repeat sequence linked to the 3' end of a spacer sequence can have 10 or more nucleotides having at least about 50% or more identity to a wild type repeat nucleotide sequence. In yet further embodiments, a repeat sequence can comprise, consist essentially of, or consist of a hairpin only having at least about 20 to 30 nucleotides in length.

A "CRISPR array" as used herein means a nucleic acid molecule that comprises at least two repeat sequences, or a portion of each of said repeat sequences, and at least one spacer sequence, wherein one of the two repeat sequences, or a portion thereof, is linked to the 5' end of the spacer sequence and the other of the two repeat sequences, or portion thereof, is linked to the 3' end of the spacer sequence. In a recombinant CRISPR array, the combination of repeat sequences and spacer sequences is synthetic, made by man and not found in nature. In some embodiments, a "CRISPR array" refers to a nucleic acid construct that comprises from 5' to 3' at least one repeat-spacer sequences (e.g., about 1, 2, 3, 4, 5, 6, 7, 8, 9, 10, 11, 12, 13, 14, 15, 16, 17, 18, 19, 20, 21, 22, 23, 24, 25 or more repeat-spacer sequences, and any range or value therein), wherein the 3' end of the 3' most repeat-spacer sequence of the array is linked to a repeat sequence, thereby all spacers in said array are flanked on both the 5' end and the 3' end by a repeat sequence.

A CRISPR array of the invention can be of any length and comprise any number of spacer sequences alternating with repeat sequences, as described above. In some embodiments, a CRISPR array can comprise, consist essentially of, or consist of 1 to about 100 spacer sequences, each linked on its 5' end and its 3' end to a repeat sequence (e.g., repeat-spacer-repeat-spacer-repeat-spacer-repeat-spacer-repeat, and so on, so that each CRISPR array begins and ends with a repeat). Thus, in some embodiments, a recombinant CRISPR array of the invention can comprise, consist essentially of, or consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more, spacer sequences each linked on its 5' end and its 3' end to a repeat sequence.

"CRISPR phage," as used herein means phage particle comprising bacteriophage DNA comprising at least one heterologous polynucleotide encoding at least one component of a CRISPR-Cas system (e.g., CRISPR array, crRNA; e.g., P1 bacteriophage comprising an insertion of crRNA targeting ftsA).

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

A "spacer sequence" as used herein is a nucleotide sequence that is complementary to a target DNA (i.e., target region in the genome or the "protospacer sequence," which is adjacent to a protospacer adjacent motif (PAM) sequence). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target DNA. Thus, in some embodiments, the spacer sequence can have one, two, three, four, or five mismatches as compared to the target DNA, which mismatches can be contiguous or noncontiguous. In some embodiments, the spacer sequence can have 70% complementarity to a target DNA. In other embodiments, the spacer nucleotide sequence can have 80% complementarity to a target DNA. In still other embodiments, the spacer nucleotide sequence can have 85%, 90%, 95%, 96%, 97%, 98%, 99%, and the like, complementarity to a target nucleotide sequence of a target gene. In representative embodiments, the spacer sequence has 100% complementarity to the target DNA. In particular embodiments, a spacer sequence has complete complementarity or substantial complementarity over a region of a target nucleotide sequence that is at least about 8 nucleotides to about 150 nucleotides in length. In representative embodiments, a spacer sequence has complete complementarity or substantial complementarity over a region of a target nucleotide sequence that is at least about 20 nucleotides to about 100 nucleotides in length. In some embodiments, the 5' region of a spacer sequence can be 100% complementary to a target DNA while the 3' region of said spacer can be substantially complementary to the said target DNA and therefore the overall complementarity of the spacer sequence to the target DNA is less than 100%. Thus, for example, the first 7, 8, 9, 10, 11, 12, 13, 14, 15, 16, and the like, nucleotides in the 3' region of a 20 nucleotide spacer sequence (seed region) can be 100% complementary to the target DNA, while the remaining nucleotides in the 5' region of the spacer sequence are substantially complementary (e.g., at least about 70% complementary) to the target DNA. In some embodiments, the first 7 to 12 nucleotides of the 3' end of the spacer sequence can be 100% complementary to the target DNA, while the remaining nucleotides in the 5' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA. In some embodiments, the first 7 to 10 nucleotides in the 3' end of the spacer sequence can be 75%-99% complementary to the target DNA, while the remaining nucleotides in the 5' region of the spacer sequence are at least about 50% to about 99% complementary to the target DNA. In other embodiments, the first 7 to 10 nucleotides in the 3' end of the spacer sequence can be 100% complementary to the target DNA, while the remaining nucleotides in the 5' region of the spacer sequence are substantially complementary (e.g., at least about 70% complementary) to the target DNA. In representative embodiments, the first 10 nucleotides (within the seed region) of the spacer sequence can be 100% complementary to the target DNA, while the remaining nucleotides in the 5' region of the spacer sequence are substantially complementary (e.g., at least about 70% complementary) to the target DNA. In an exemplary embodiment, the 5' region of a spacer sequence (e.g., the first 8 nucleotides at the 5' end, the first 10 nucleotides at the 5' end, the first 15 nucleotides at the 5' end, the first 20 nucleotides at the 5' end) can have about 75% complementarity or more (75% to about 100% complementarity) to a target DNA, while the remainder of the spacer sequence can have about 50% or more complementarity to the target DNA. Thus, for example, the first 8 nucleotides at the 5' end of a spacer sequence can have 100% complementarity to the target nucleotide sequence or it can have one or two mutations and therefore can be about 88% complementary or about 75% complementary to a target DNA, respectively, while the remainder of the spacer nucleotide sequence can be at least about 50% or more complementary to the target DNA.

In some embodiments, a spacer sequence of this invention can be about 15 nucleotides to about 150 nucleotides in length. In other embodiments, a spacer nucleotide sequence of this invention can be about 15 nucleotides to about 100 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides or more). In some particular embodiments, a spacer nucleotide sequence can be a length of about 8 to about 150 nucleotides, about 8 to about 100 nucleotides, about 8 to about 50 nucleotides, about 8 to about 40 nucleotides, about 8 to about 30 nucleotides, about 8 to about 25 nucleotides, about 8 to about 20 nucleotides, about 10 to about 150 nucleotides, about 10 to about 100 nucleotides, about 10 to about 80 nucleotides, about 10 to about 50 nucleotides, about 10 to about 40, about 10 to about 30, about 10 to about 25, about 10 to about 20, about 15 to about 150, about 15 to about 100, about 15 to about 50, about 15 to about 40, about 15 to about 30, about 20 to about 150 nucleotides, about 20 to about 100 nucleotides, about 20 to about 80 nucleotides, about 20 to about 50 nucleotides, about 20 to about 40, about 20 to about 30, about 20 to about 25, at least about 8, at least about 10, at least about 15, at least about 20, at least about 25, at least about 30, at least about 32, at least about 35, at least about 40, at least about 44, at least about 50, at least about 60, at least about 70, at least about 80, at least about 90, at least about 100, at least about 110, at least about 120, at least about 130, at least about 140, at least about 150 nucleotides in length, or more, and any value or range therein.

In some embodiments, a spacer can be modified relative to the typical length of a wild type spacer Type I-E CRISPR Cas system in *E. coli* (e.g., about 32 nucleotides long) (i.e., made longer (extended) or shorter). In some embodiments, the spacer is made longer by extending the 3' end of the spacer to include additional nucleotides that are complementary to the target DNA. Thus, as discussed above, in some aspects, a spacer sequence has complete complementarity or substantial complementarity over a region of a target nucleotide sequence that is at least about 15 nucleotides to about 150 nucleotides in length, about 15 nucleotides to about 100 nucleotides in length, about 20 nucleotides to about 150 nucleotides in length, about 20 nucleotides to about 100 nucleotides in length and the like (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150 nucleotides, or any range or value therein). In some aspects, the spacer at its 3' end can be fully complementary or substantially complementary (e.g., at least about 20, 30, 40, 50, 55, 60, 65, 70, 75, 80, 85, 90, 95, 96, 97, 98, 99% or more) to a portion of consecutive nucleotides of the target DNA.

In representative embodiments, a spacer sequence of a Type II CRISPR repeat-spacer nucleic acid of the invention comprises at least about 16 nucleotides, wherein at the 3' end of said spacer at least about 10 consecutive nucleotides of said at least about 16 nucleotides have at least about 90% complementarity to 10 consecutive nucleotides of a target nucleic acid, wherein the target nucleic acid is adjacent to a protospacer adjacent motif (PAM) sequence in the genome of an organism of interest.

In representative embodiments, a spacer sequence of a Type I CRISPR repeat-spacer nucleic acid of the invention comprises at least about 15 nucleotides, wherein at the 5' end of said spacer at least about 7 consecutive nucleotides of said at least about 15 nucleotides have at least about 90% complementarity to 7 consecutive nucleotides of a target nucleic acid, wherein the target nucleic acid is adjacent to a protospacer adjacent motif (PAM) sequence in the genome of an organism of interest.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In particular embodiments, substantial identity can refer to two or more sequences or subsequences that have at least about 70%, at least about 75%, at least about 80%, at least about 85%, at least about 90%, at least about 95, 96, 96, 97, 98, or 99% identity.

As used herein, the phrase "substantially complementary," or "substantial complementarity" in the context of two nucleic acid molecules or nucleotide sequences refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide complementarity, when compared and aligned for maximum correspondence, as measured using one of the following sequence comparison algorithms or by visual inspection. In particular embodiments, substantial complementarity can refer to two or more sequences or subsequences that have at least about 70%, at least about 75%, at least about 80%, at least about 85%, at least about 90%, at least about 95, 96, 96, 97, 98, or 99% complementarity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)).

One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

As used herein, a "target DNA," "target nucleotide sequence," "target region," or a "target region in the genome" refers to a region of an organism's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a CRISPR array. In some embodiments, a target region may be about 10 to about 40 consecutive nucleotides in length located immediately adjacent to a PAM sequence (PAM sequence located immediately 3' of the target region) in the genome of the organism.

In some aspects, a target nucleotide sequence is located adjacent to or flanked by a PAM (protospacer adjacent motif). While PAMs are often specific to the particular CRISPR-Cas system, a PAM sequence can be determined by those skilled in the art through established experimental and computational approaches. Thus, for example, experimental approaches include targeting a sequence flanked by all possible nucleotides sequences and identifying sequence members that do not undergo targeting, such as through in vitro cleavage of target DNA (Patanayak et al. 2013. *Nat. Biotechnol.* 31:839-843) or the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

A "trans-activating CRISPR (tracr) nucleic acid" or "tracr nucleic acid" as used herein refers to any tracr RNA (or its encoding DNA). A tracr nucleic acid comprises from 5' to 3' a bulge, a nexus hairpin and terminal hairpins, and optionally, at the 5' end, an upper stem (See, Briner et al. (2014) *Molecular Cell.* 56(2):333-339). A tracr nucleic acid functions in hybridizing to the repeat portion of mature or immature crRNAs, recruits Cas9 protein to the target site, and may facilitate the catalytic activity of Cas9 by inducting structural rearrangement. Sequences for tracrRNAs are specific to the CRISPR-Cas system and can be variable. Any tracr nucleic acid, known or later identified, can be used with this invention. In some embodiments, a tracr nucleic acid can be fused to a CRISPR array to form a single guide nucleic acid and therefore, the tracr nucleic acid and CRISPR array can be introduced as a single guide.

Any polynucleotide, nucleotide sequence and/or recombinant nucleic acid molecule of this invention (e.g., polynucleotides comprising a CRISPR array, polynucleotides encoding heterologous methyltransferases, Cascade polypeptides, Cas9 polypeptides, Cas3 polypeptides, Cas3' polypeptides, Cas3" polypeptides, recombinant Type I and Type II CRISPR-Cas systems of the invention, and the like) can be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species-specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original nucleotide sequence. Thus, in representative embodiments of the invention, the nucleotide sequence and/or recombinant nucleic acid molecule of this invention can be codon optimized for expression in the particular organism/species of interest.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, polynucleotide or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, by the hand of man, they exist apart from their native environment and therefore are not products of nature, however, in some embodiments, they can be introduced into and exist in a recombinant host cell.

In further embodiments of the invention, polynucleotides comprising tracr nucleic acids and/or CRISPR arrays or, and polynucleotides encoding heterologous methyltransferases, Cas9 polypeptides, Cas3 polypeptides, Cas3' polypeptides, Cas3" polypeptides, Cascade polypeptides and/or Type I and II CRISPR-Cas systems can be operatively associated with a variety of promoters, terminators and other regulatory elements for expression in various organisms or cells. Thus, in representative embodiments, at least one promoter and/or terminator can be operably linked to a polynucleotide of the invention. Any promoter useful with this invention can be used and includes, for example, promoters functional with the organism of interest including but not limited to constitutive, inducible, developmentally regulated, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase and directs the initiation of transcription. In general, promoters are found 5', or upstream, relative to the start of the coding region of the corresponding coding sequence. The promoter region may comprise other elements that act as regulators of gene expression. These include, but are not limited to, a −35 element consensus sequence and a −10 consensus sequence (Simpson. 1979. *Proc. Natl. Acad. Sci. U.S.A.* 76:3233-3237).

Promoters can include, for example, constitutive, inducible, temporally regulated, developmentally regulated, chemically regulated promoters for use in the preparation of recombinant nucleic acid constructs, polynucleotides, expression cassettes and vectors comprising the polynucleotides and recombinant nucleic acid constructs of the invention. These various types of promoters are known in the art.

Thus, in some embodiments, expression of a construct of the invention can be made constitutive, inducible, temporally regulated, developmentally regulated, chemically regulated promoters using the recombinant nucleic acid constructs of the invention operatively linked to the appropriate promoter functional in an organism of interest. In representative embodiments, repression can be made reversible using the recombinant nucleic acid constructs of the invention operatively linked to, for example, an inducible promoter functional in an organism of interest.

The choice of promoter will vary depending on the quantitative, temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

Exemplary promoters include useful with this invention include promoters functional in bacteria. A promoter useful with bacteria can include, but is not limited to, L-arabinose inducible (araBAD, $P_{BAD}$) promoter, any lac promoter, L-rhamnose inducible ($rhaP_{BAD}$) promoter, T7 RNA polymerase promoter, trc promoter, tac promoter, lambda phage promoter ($p_L, p_L$-9G-50), anhydrotetracycline-inducible (tetA) promoter, trp, lpp, phoA, recA, proU, cst-1, cadA, nar, lpp-lac, cspA, T7-lac operator, T3-lac operator, T4 gene 32, 15-lac operator, nprM-lac operator, Vhb, Protein A, corynebacterial-*E. coli* like promoters, thr, horn, diphtheria toxin promoter, sig A, sig B, nusG, SoxS, katb, α-amylase (Pamy), Ptms, P43 (comprised of two overlapping RNA polymerase σ factor recognition sites, σA, σB), Ptms, P43, rplK-rplA, ferredoxin promoter, and/or xylose promoter. (See, K. Terpe *Appl. Microbiol, Biotechnol.* 72:211-222 (2006); Hannig et al. Trends in Biotechnology 16:54-60 (1998); and Srivastava Protein Expr Purif 40:221-229 (2005)).

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the RNAs and/or the polypeptides of the invention to be synthesized only when, for example, an organism is treated with the inducing chemicals. Depending upon the objective, the promoter may be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induce gene expression (Levskaya et al. 2005. *Nature* 438:441-442).

In some embodiments, a nucleic acid construct of the invention can be an "expression cassette" or can be comprised within an expression cassette. As used herein, "expression cassette" means a recombinant nucleic acid construct comprising one or more polynucleotides of the invention, wherein said recombinant nucleic acid construct is operably associated with at least one control sequence (e.g., a promoter). Thus, some aspects of the invention provide expression cassettes designed to express the polynucleotides of the invention.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof). In some embodiments of this invention, terminators can be operably linked to the recombinant nucleic acid molecule and CRISPR array of the invention.

An expression cassette also can include a nucleotide sequence encoding a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or whether the marker is simply a trait that one can identify through observation or testing, such as by screening (e.g., fluorescence). Of course, many examples of suitable selectable markers are known in the art and can be used in the expression cassettes described herein.

In addition to expression cassettes, the recombinant polynucleotides described herein (e.g., polynucleotides comprising a CRISPR array and/or a tracr nucleic acid, and polynucleotides encoding heterologous methyltransferases, Cascade polypeptides, Cas9 polypeptides, Cas3 polypeptides, Cas3' polypeptides, Cas3" polypeptides, recombinant Type I and Type II CRISPR-Cas systems of the invention, and the like) can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform a prokaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, such as broad-host plasmids or shuttle vectors with multiple origins-of-replication. In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the recombinant polynucleotides of this invention and/or expression cassettes comprising the recombinant polynucleotides of this invention can be comprised in vectors as described herein and as known in the art.

As used herein, the terms "contacting," "introducing," "delivering," and "administering" can refer to a process by which the recombinant polynucleotides of the present invention are delivered to a cell, for example, to alter the methylation activity of the host cell or to kill a cell comprising target DNA having substantial complementarity to at least one spacer of an introduced (heterologous/exogenous) CRISPR array. Thus, in the context of a polynucleotide of interest, the terms "contacting," "introducing," "delivering," and "administering" (and grammatical variations thereof) in the context of a polynucleotide of interest mean presenting a polynucleotide of interest to a host organism or a cell of said organism (e.g., host cell such as a bacterial cell) in such a manner that the polynucleotide gains access to the interior of a cell and includes such terms as transformation," "transfection," and/or "transduction." Where more than one polynucleotide is to be introduced, these polynucleotides can be assembled as part of a single polynucleotide or nucleic acid construct, or as separate polynucleotide or nucleic acid constructs, and can be located on the same or different expression constructs or transformation vectors. Accordingly, these polynucleotides can be introduced into cells in a single transformation event and/or in separate transformation events. Thus, in some aspects of the present invention one or more polynucleotides of this invention can be introduced into a cell of a host bacterium.

The terms "transformation," "transfection," and "transduction" as used herein refer to the introduction of a heterologous polynucleotide into a cell. Such introduction into a cell may be stable or transient. Thus, in some embodiments, a host cell or host organism is stably transformed with a nucleic acid molecule of the invention. In other embodiments, a host cell or host organism is transiently transformed with a recombinant nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plasmid genome, and therefore includes integration of the nucleic acid construct into, for example, the plasmid genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a bacterium). Stable transformation of a cell can be detected by, for example, a Northern blot hybridization assay of RNA of the cell with nucleic acid sequences which specifically hybridize with a nucleotide sequence of a transgene introduced into said cell. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or by hybridization protocols well known in the art.

Accordingly, in some embodiments, the polynucleotide sequences, nucleic acid constructs, expression cassettes, and/or vectors of the invention can be expressed transiently and/or they can be stably incorporated into the genome of the host organism.

A polynucleotide of the invention can be introduced into a cell by any method known to those of skill in the art. Exemplary methods of transformation include transformation via electroporation of competent cells, passive uptake by competent cells, chemical transformation of competent cells, as well as any other electrical, chemical, physical (mechanical) and/or biological mechanism that results in the introduction of nucleic acid into a cell, including any combination thereof.

In some embodiments of the invention, transformation of a cell comprises nuclear transformation. In some embodiments of the invention, transformation of a cell comprises plasmid transformation and conjugation.

Procedures for transforming prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

A nucleotide sequence therefore can be introduced into a host organism or its cell in any number of ways that are well known in the art. The methods of the invention do not depend on a particular method for introducing one or more nucleotide sequences into the organism, only that they gain access to the interior of the cell. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events.

The present inventors have identified novel integration sites for incorporating heterologous DNA into a bacteriophage genome including simABC, imcB/coi, res-mod, darA, phd-doc, kilA, tRNA 1,2, cixL, cixR and Is1. Further, the inventors have surprisingly found that the phage DNA including that comprising introduced heterologous polynucleotide(s) can be methylated to be substantially similar to a target host bacterium by growing the phage in a production host bacterium having a methylation pattern (R-M system) that is substantially similar to the target host bacterium. Efficient methylation of the phage is unexpected due to the rapid replication of the phage DNA prior to packaging (e.g., for P1) or for the packaging of single-stranded DNA (e.g. M13), which would otherwise be expected to prevent methylation prior to DNA packaging.

Thus, in some aspects, the present invention is directed to methods and compositions for modifying the methylation pattern of bacteriophage DNA and phagemid DNA.

Accordingly, in some embodiments, the present invention provides an in vivo method of modifying the methylation pattern of a bacteriophage DNA or phagemid DNA, comprising: altering methylating activity of a production host bacterium, comprising (1) disrupting the activity at least one enzyme of an endogenous restriction modification system (R-M system) of a production host bacterium, thereby producing a modified production host bacterium having the activity of at least one enzyme of the endogenous R-M system disrupted, and/or (2) introducing into a production host bacterium a polynucleotide encoding at least one heterologous methyltransferase, thereby producing a modified production host bacterium expressing the heterologous methyltransferase; infecting the modified production host bacterium having an altered methylating activity with a bacteriophage particle comprising bacteriophage DNA or phagemid DNA, thereby methylating said bacteriophage DNA or phagemid DNA; and producing a bacteriophage particle comprising bacteriophage DNA or phagemid DNA having a modified methylation pattern as compared to a bacteriophage grown in a control production host bacterium (wherein the control production host bacterium has not had its methylation activity altered as described herein).

In some aspects, the infecting step can be carried out prior the step of altering the methylating activity of the production host bacterium. Thus, in some aspects the present invention provides an in vivo method of modifying the methylation pattern of a bacteriophage DNA or phagemid DNA, comprising: infecting the modified production host bacterium having an altered methylating activity with a bacteriophage particle comprising bacteriophage DNA or phagemid DNA, thereby methylating said bacteriophage DNA or phagemid DNA; altering methylating activity of a production host bacterium, comprising (1) disrupting the activity at least one enzyme of an endogenous restriction modification system (R-M system) of a production host bacterium, thereby producing a modified production host bacterium having the activity of at least one enzyme of the endogenous R-M system disrupted, and/or (2) introducing into a production host bacterium a polynucleotide encoding at least one heterologous methyltransferase, thereby producing a modified production host bacterium expressing the heterologous methyltransferase; and producing a bacteriophage particle comprising bacteriophage DNA or phagemid DNA having a modified methylation pattern as compared to a bacteriophage grown in a control production host bacterium (wherein the control production host bacterium has not had its methylation activity altered as described herein).

Further provided is an in vivo method of modifying the methylation pattern of a bacteriophage DNA or phagemid DNA, comprising: infecting a production host bacterium with a bacteriophage particle comprising bacteriophage DNA or phagemid DNA, wherein the production host bacterium has altered methylating activity via disruption of at least one enzyme of an endogenous R-M system and/or expression of at least one heterologous methyltransferase, thereby methylating said bacteriophage DNA or phagemid DNA; and producing a bacteriophage particle comprising bacteriophage DNA or phagemid DNA having a modified methylation pattern as compared to a bacteriophage grown in a control production host bacterium (wherein the control production host bacterium has not had its methylation activity altered as described herein).

In some embodiments, two or more (e.g., 2, 3, 4, 5, 6, 7, 8, 9, 10, 11, 12, 13, 14, 15, etc) enzymes of the endogenous restriction modification system of a production host bacterium may be disrupted or altered in activity.

A production host bacterium can be any gram positive or gram negative bacterium. Thus, in some embodiments, production host bacterium includes but is not limited to *Escherichia coli, Bacillus subtilis, Lactobacillus rhamnosus, Salmonella enteria, Streptococcus thermophilus, Listeria, Campylobacter* or *Staphylococcus aureus*. In representative embodiments, the production host bacterium can be *E. coli*. In further embodiments, the production host bacterium can be *E. coli* strain MG1655, BW25113, BL21, TOP10, or MG1655 Δdam Δdcm ΔhsdRMS.

In some embodiments of the invention, the methylating activity of the production host bacterium is not modified. Accordingly, in some embodiments, a production host bacterium that is not modified to alter its methylating activity can be infected with a bacteriophage particle comprising recombinant bacteriophage DNA or phagemid DNA.

Any known or later identified bacteriophage DNA can be used with the present invention. In some embodiments, the bacteriophage DNA can be from a lysogenic or temperate bacteriophage. In some embodiments, the bacteriophage DNA can be from a lytic bacteriophage when coupled with a phagemid.

In some embodiments, the bacteriophage DNA can be from a temperate bacteriophage. However, an event such as UV exposure, starvation, altering the temperature, the presence of inducing chemicals, and/or inducing expression of lytic transcription factor can induce the lytic cycle causing proliferation of new phages. In some embodiments of the invention, a bacteriophage DNA can include but is not limited to DNA of a P1 phage, a M13 phage, a λ phage, a T4 phage, a PhiC2 phage, a PhiCD27 phage, a PhiNM1 phage, Bc431v3 phage, phage, Phi10 phage, Phi25 phage, Phi151 phage, A511-like phages, B054, 01761-like phages, or *Campylobacter* phages (such as NCTC12676 and NCTC12677). In some embodiments, a production host bacterium can be a gram-negative bacterium and the bacteriophage DNA can be, for example, P1 phage, M13 phage, λ phage, Phi10, Phi25, Phi151, *Campylobacter* phages (such as NCTC12676 and NCTC12677), or T4 phage. In other embodiments, a production host bacterium can be a gram-positive bacterium and the bacteriophage DNA can be, for example, a PhiC2 phage, a PhiCD27 phage, a PhiNM1 phage, B054, 01761-like phages, or a Bc431v3 phage.

Any known or later identified phagemid DNA can be used with the present invention. In some embodiments, a phagemid DNA useful with this invention can include, but is not limited to, the DNA of a P1 phagemid, a M13 phagemid, a λ phagemid, a T4 phagemid, a PhiC2 phagemid, a PhiCD27 phagemid, a PhiNM1 phagemid, Bc431v3 phagemid, Phi10 phagemid, Phi25 phagemid, Phi151 phagemid, A511-like phagemids, B054, 01761-like phagemids, *Campylobacter* phagemids (such as NCTC12676 and NCTC12677).

The activity of an enzyme of an endogenous R-M system may be disrupted using methods well known in the art or later developed for disrupting the function and activity of a polypeptide. Such methods can include, but are not limited to, generating point mutations (e.g., missense, or nonsense, or insertions or deletions of single base pairs that result in frame shifts), insertions, deletions, and/or truncations. In some embodiments, a polypeptide inhibitor may be used to disrupt or suppress the activity of an enzyme of a bacterial restriction modification system (R-M system). Such polypeptide inhibitors are known in the art. Polypeptide inhibitors may be encoded, for example, within the bacteriophage DNA, phagemid DNA and/or packaged as proteins in the bacteriophage particle. For example, P1 phage encodes two polypeptide inhibitors that inhibit Type I restriction enzymes found in *E. coli* (Lobocka et al. *J. Bacteria* 186, 7032-7068 (2004)). In some embodiments, an endogenous R-M system may be inhibited or disrupted by the introduction of polypeptide inhibitors, polypeptides that stimulate the activity of the host methylation enzymes to accelerate the methylation and protection of the delivered DNA.

Inhibitors of R-M system enzymes include but are not limited to proteins that degrade the REase (restriction endonuclease), thereby preventing the host R-M enzyme system from cleaving the phage DNA. Non-limiting examples of an R-M enzyme inhibitor that may be used with this invention to disrupt or modify the activity of an endogenous bacterial R-M system enzyme include (a) orf18 from *Enterococcus faecalis*, which produces the protein ArdA that inhibits all major classes of type I R-M systems; and (b) gp0.3 from bacteriophage T7 produces the protein Ocr that sequesters the type I R-M enzyme EcoKI. Additional non-limiting examples of proteins that may be used to block the activity of an enzyme of an R-M system include masking proteins. Masking proteins are packaged into the phage head and upon DNA injection bind the phage DNA, thereby masking R-M recognition sites. Non-limiting examples of masking proteins useful with this invention include DarA and DarB proteins (Iida et al. *Virology.* 157(1):156-66 (1987)). These proteins are expressed by the P1 bacteriophage during the lytic cycle and are packaged into the head. Upon DNA injection to a host bacterium, they bind and mask the Type I R-M recognition sites.

In addition to or in the alternative, an endogenous R-M system of a production host bacterium can be altered/modified through the expression of at least one heterologous methyltransferase. Any methyltransferase that alters the endogenous methylation pattern of a production host bacterium so that the methylation pattern of the production host bacterium is substantially similar to the methylation pattern of the target bacterium can be used with this invention. The heterologous methyltransferase may be from the same or a different organism as long as it confers a methylation pattern substantially similar to the production host bacterium as the target bacterial strain. A non-limiting example of a DNA MTase useful with the invention includes LlaPI from phage Φ50, which can be introduced to protect against type II R-M systems in lactococci (McGrath et al. *Applied Environmental Microbiology.* 65:1891-1899 (1999)). The methylation patterns conferred by individual methyltransferases are then assessed using established DNA sequencing technologies such as Pacbio SMRT sequencing (O'Loughlin et al. *PLoS One.* 2015:e0118533.). Once generated, the production strain is used to produce bacteriophage particles for DNA delivery into the target strain.

Further heterologous DNA modification enzymes can be expressed in a production host bacterium so that the R-M system of the production host bacterium is made substantially similar to the R-M system of the target bacterium. Examples of such DNA modification enzymes useful for this purpose include those that encode polypeptides that convert the adenine residues in the DNA to acetamidoadenine. Polypeptides that convert the adenine residues in the bacteriophage DNA to acetamidoadenine will protect the DNA against restriction enzymes that are sensitive to adenine methylation. Non-limiting examples of polypeptides that can convert the adenine residues in the DNA to acetamidoadenine.in the production host bacteria include the mom gene from phage Mu and the Mu-like prophage sequences (see, *Haemophilus influenzae* Rd (FluMu), *Neisseria meningitidis* type A strain Z2491 (Pnme1) and *H. influenzae* biotype *aegyptius* ATCC 11116; (Drozdz et al. *Nucleic Acids*

*Res.* 40(5):2119-30 (2012)), which converts adenine residues to N(6)-methyladenine, thereby protecting against adenine-sensitive restriction enzymes.

In some embodiments, the polynucleotides encoding polypeptide inhibitors and other DNA modification enzymes as described herein can be introduced into the phage genome directly for use in protecting the delivered DNA from the R-M system of the target host bacterium.

The process of infecting bacteria with bacteriophage particles is well known and may comprise, for example, incubating the bacterial host cells with the bacteriophage particles under specified conditions. Following replication in the bacterial host cells, the lytic cycle can be triggered through different established methods including, but not limited to, UV exposure, starvation, altering the temperature, or inducing expression of a lytic transcription factor to obtain bacteriophage particles comprising the bacteriophage DNA or the phagemid DNA.

The present invention further relates to methods and compositions for the use of bacteriophage particles of the invention for increasing the efficiency of introducing heterologous DNA via bacteriophage and phagemids. Thus, in some embodiments, at least one heterologous nucleic acid of interest can be introduced into a bacteriophage DNA or into a phagemid DNA. Methods for introducing heterologous polynucleotides into bacteriophage DNA or phagemid DNA are well known in the art. In some embodiments, at least one heterologous nucleic acid of interest can be introduced into a bacteriophage DNA, for example, via homologous recombination while the bacteriophage DNA is in a host bacterium (e.g., production host bacterium), or into a phagemid DNA via standard cloning techniques.

In some embodiments, the at least one heterologous nucleic acid of interest can be a reporter gene (e.g. gfp, lacZ), an antibiotic resistance marker (e.g. cat, bla), polynucleotides encoding one or more polypeptides in a metabolic pathway (e.g. carotenoid biosynthesis), a gene regulator (e.g. dCas9, tetR), and/or further copies of any endogenous gene (e.g. for overexpression).

Accordingly, in some embodiments, the invention provides a method of increasing the efficiency of introducing a heterologous nucleic acid of interest into a target host bacterium via bacteriophage, comprising introducing at least one heterologous nucleic acid of interest into a bacteriophage DNA or a phagemid DNA prior to infection of a production host bacterium, wherein the production host bacterium has been modified to disrupt at least one enzyme of an endogenous R-M system and/or to comprise a polynucleotide encoding at least one heterologous methyltransferase, thereby methylating said bacteriophage DNA or phagemid DNA and producing recombinant bacteriophage DNA or a phagemid DNA comprising the at least one heterologous nucleic acid of interest having a modified methylation pattern (as compared to bacteriophage or phagemid DNA produced in a production host bacterium without said altered methylating activity); producing a bacteriophage particle comprising said recombinant bacteriophage DNA or a phagemid DNA comprising the at least one heterologous nucleic acid of interest; and infecting a target host bacterium with said bacteriophage particle, wherein the target host bacterium has a methylation pattern (or R-M system(s)) that is substantially similar to that of the production host bacterium, thereby increasing the efficiency of introducing said heterologous nucleic acid of interest into said target host bacterium as compared to introducing said heterologous nucleic acid of interest using a bacteriophage grown in a control production host bacterium (wherein the control production host bacterium has not had its methylation activity altered to be substantially similar with that of the target host bacterium). In some aspects, the production host bacterium can be modified to alter its R-M system (e.g., disrupt at least one enzyme of an endogenous R-M system and/or to comprise a polynucleotide encoding at least one heterologous methyltransferase) after infection by the bacteriophage.

In some embodiments a method of increasing the efficiency of introducing a heterologous nucleic acid of interest into a target host bacterium via bacteriophage is provided, comprising: infecting a production host bacterium with a bacteriophage particle comprising bacteriophage DNA or phagemid DNA comprising at least one heterologous nucleic acid of interest, wherein the production host bacterium has altered methylating activity via disruption of at least one enzyme of an endogenous R-M system and/or expression of at least one heterologous methyltransferase, thereby methylating said bacteriophage DNA or phagemid DNA; producing a bacteriophage particle comprising bacteriophage DNA or phagemid DNA having a modified methylation pattern and comprising/encoding the at least one heterologous nucleic acid of interest; and infecting a target host bacterium with said bacteriophage particle, wherein the target host bacterium has a methylation pattern (or R-M system(s)) that is substantially similar with that of the production host bacterium, thereby increasing the efficiency of introducing said heterologous nucleic acid of interest into said target host bacterium as compared to introducing said heterologous nucleic acid of interest using a bacteriophage grown in a control production host bacterium (wherein the control production host bacterium has not had its methylation activity altered to be substantially similar to that of the target host bacterium as described herein). In some aspects, the production host bacterium can be modified to alter its R-M system (e.g., disrupt at least one enzyme of an endogenous R-M system and/or to comprise a polynucleotide encoding at least one heterologous methyltransferase) after infection by the bacteriophage.

The present invention further relates to methods and compositions for the use of bacteriophage particles of the invention for delivery of genome targeting CRISPR-Cas systems. In particular embodiments, methods and compositions are provided for selective killing of bacteria using temperate bacteriophages comprising bacteriophage DNA or phagemid DNA that comprise an engineered CRISPR-Cas system as described herein.

Thus, in some embodiments, a bacteriophage DNA or phagemid DNA can be transformed with at least one heterologous nucleic acid of interest, wherein the at least one heterologous nucleic acid of interest comprises a CRISPR array. In additional embodiments, the CRISPR array can be a Type II CRISPR array or a Type I CRISPR array. In some embodiments, the Type II CRISPR array is introduced into bacteriophage DNA and not phagemid DNA. In some embodiments, the Type I CRISPR array is introduced into bacteriophage DNA and not phagemid DNA. Thus, in some embodiments, the invention provides a bacteriophage particle comprising bacteriophage DNA or phagemid DNA, wherein the bacteriophage DNA or phagemid DNA comprise a polynucleotide encoding a CRISPR array, the CRISPR array comprises a repeat-spacer-repeat sequence, or at least two or more repeat-spacer sequences and the at least two or more repeat-spacer sequences comprise at least a first repeat-spacer sequence and a final repeat-spacer sequence and the 3' end of the spacer of said first repeat-spacer sequence is linked to the 5' end of a repeat of a next repeat-spacer sequence and the final repeat-spacer sequence is linked at the 3' end to a repeat.

In some embodiments, when the CRISPR array is a Type II CRISPR array, the bacteriophage DNA or phagemid DNA can be additionally transformed to comprise (a) a tracr nucleic acid and a polynucleotide encoding a Cas9. Accordingly, in some embodiments, a bacteriophage DNA can be engineered to comprise a recombinant Type II CRISPR-Cas system (e.g., a CRISPR array, tracr nucleic acid and polynucleotide encoding a Cas9 polypeptide). In other embodiments, a phagemid DNA can be engineered to comprise a recombinant Type II CRISPR-Cas system.

Accordingly, in some embodiments, the present invention provides a bacteriophage particle comprising bacteriophage DNA or phagemid DNA, wherein the bacteriophage DNA or phagemid DNA comprise a recombinant Type II CRISPR-Cas system comprising: (a) a polynucleotide encoding a Cas9 polypeptide; (b) a polynucleotide encoding a CRISPR array; and c) a tracr nucleic acid, optionally wherein the polynucleotide encoding a CRISPR array and the tracr nucleic acid are fused to one another (to form a single guide nucleic acid(sgRNA, sgDNA). In some embodiments, the invention provides a bacteriophage particle comprising bacteriophage DNA comprising a polynucleotide encoding a Type II CRISPR array. In further embodiments, the invention provides a bacteriophage particle comprising phagemid DNA comprising a polynucleotide encoding a Type II CRISPR array and/or a single guide nucleic acid (fused CRISPR array and tracr nucleic acid).

In some embodiments, a Type II CRISPR-Cas system or components thereof may be introduced in the same or in a different bacteriophage from the bacteriophage comprising the CRISPR array or from one another. Thus, for example, a recombinant phage may be introduced into a target bacterium, wherein the recombinant phage comprises in its DNA an array only. In this case, the target bacterium may comprise the Type II CRISPR-Cas system that is compatible to the CRISPR array being introduced or a Type II CRISPR-Cas system or components thereof may be introduced in one or more further recombinant bacteriophage. Accordingly, a bacteriophage may be engineered to comprise and introduce only a Type II CRISPR array; a single guide; a Cas9; a tracr; a Type II CRISPR array and a Cas9; a Type II CRISPR array and a tracr; a Type II CRISPR array, a Cas9 and a tracr; a Type II CRISPR array and a single guide; and the like.

In some embodiments, when the CRISPR array is a Type I CRISPR array, the bacteriophage DNA or phagemid DNA can be additionally transformed to comprise at least one a polynucleotide encoding a Cas3 polypeptide, or aCas3' and a Cas3" polypeptide, and/or one or more polynucleotides encoding Type I Cascade polypeptides. Accordingly, in some embodiments, a bacteriophage DNA can be engineered to comprise a Type I CRISPR-Cas system (e.g., a CRISPR array, and Type I polypeptides (e.g., polynucleotides encoding a Cas3 polypeptide, or aCas3' and a Cas3" polypeptide, and one or more polynucleotides encoding Type I Cascade polypeptides). In other embodiments, a phagemid DNA can be engineered to comprise a Type I CRISPR-Cas system. Accordingly, in some embodiments, the present invention provides a bacteriophage particle comprising bacteriophage DNA or phagemid DNA, wherein the bacteriophage DNA or phagemid DNA comprise a recombinant Type I CRISPR-Cas system comprising (a) a polynucleotide encoding a CRISPR array; and (b) at least one polynucleotide encoding one or more Type I CRISPR polypeptides. In some embodiments, the invention provides a bacteriophage particle comprising bacteriophage DNA comprising a polynucleotide encoding a Type I CRISPR array. In further embodiments, the invention provides a bacteriophage particle comprising phagemid DNA comprising a polynucleotide encoding a Type I CRISPR array.

In some embodiments, a Type I CRISPR-Cas system or components thereof may be introduced in the same or in a different bacteriophage from the bacteriophage comprising the CRISPR array or from one another. Thus, for example, a recombinant phage may be introduced into a target bacterium, wherein the recombinant phage comprises in its DNA a CRISPR array only. In this case, the target bacterium may comprise the Type I CRISPR-Cas system that is compatible to the CRISPR array being introduced or a Type I CRISPR-Cas system or components thereof may be introduced in one or more further recombinant bacteriophage. Accordingly, a bacteriophage may be engineered to comprise and introduce only a Type I CRISPR array; a Cas3; one or more Cascade polynucleotides; a CRISPR array and a Cas3, a CRISPR array and one or more Cascade polypeptides; a Cas3 and one or more Cascade polypeptides; a CRISPR array, a Cas3, and one or more Cascade polypeptides; and the like.

In some embodiments, the bacteriophage DNA and the phagemid DNA comprising a recombinant Type II CRISPR-Cas system or a recombinant Type I CRISPR-Cas system can be modified as described herein to comprise a modified DNA methylation pattern as compared to a bacteriophage DNA or phagemid DNA not so modified, optionally wherein the modified DNA methylation pattern results in the bacteriophage DNA or phagemid DNA comprising a modified DNA methylation pattern that is substantially similar to the restriction-modification system(s) of a target host bacterium. Thus, in some embodiments, the at least one heterologous nucleic acid of interest can be introduced into a bacteriophage DNA or a phagemid DNA prior to infection of said bacteriophage DNA or phagemid DNA into a production host bacterium that has modified methylating activity. In such a manner, the bacteriophage DNA or phagemid DNA transformed with the nucleic acid of interest is methylated by the host bacterium methylation machinery while replicating in the production host bacterium. Repackaging and lysis of the host cell then produces bacteriophage particles comprising the bacteriophage DNA or phagemid DNA comprising the at least one heterologous nucleic acid of interest having a methylation pattern corresponding to that which is present in the production host bacterium. The bacteriophage particles produced by the production host bacterium can then be used to infect a target host bacterium, thereby introducing the nucleic acid of interest into the target host bacterium. Typically, the target host bacterium is chosen on the basis of having a DNA methylation pattern substantially similar to a production host bacterium's restriction-modification system(s) (R-M system). Alternatively, the production host bacterium's methylating activity is modified to be substantially similar to the R-M system of a target host bacterium, thereby providing a production host bacterium that can be used to produce bacteriophage DNA and/or phagemid DNA that has a methylation pattern that is substantially similar to the R-M system(s) of a target host bacterium. Thus, in some embodiments, the DNA methylation activity of the production host bacterium is altered prior to infection with the bacteriophage particles as described herein, thereby producing bacteriophage particles comprising transformed bacteriophage DNA or phagemid DNA having an altered methylation pattern as compared to bacteriophage DNA or phagemid DNA grown in a control production host bacterium (e.g., wherein the control production host bacterium has not had its methylation activity altered as described herein). In some embodiments, the altered methylation pattern of the transformed bacteriophage DNA or phagemid DNA can correspond to the methylation activity (the R-M system) of a target host bacterium, thereby increasing delivery of the transformed DNA to the target host bacterium as compared to bacteriophage DNA or phagemid DNA having a methylation pattern that does not correspond to that of the target host bacterium.

In some embodiments, the production host bacterium can naturally comprise a methylation pattern that is substantially similar to that of a target bacterium. Thus, when the bacteriophage DNA or phagemid DNA is produced in the production host bacterium, the bacteriophage DNA or phagemid DNA will have the methylation pattern of both the production host bacterium as well as that of the target host bacterium, thereby increasing delivery of the transformed DNA to the target host bacterium as compared to bacteriophage DNA or phagemid DNA having a methylation pattern that is not substantially the same as that of the target host bacterium.

A methylation pattern is determined by the type of methylation (e.g. m4C) present in the bacterium as well as the particular sequence that is methylated (e.g. GmATC). Thus, the level of similarity (whether it is natural or the result of modifications) between methylation patterns refers to the frequency by which target sites having the appropriate type of methylation. Thus, a substantially similar methylation pattern means having at least about 20% or greater similarity (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or more, or any range or value therein) between the target sites having the appropriate type of methylation as described herein. Thus, in some embodiments, a methylation pattern can be between about 20% to 99% or more similar, about 30% to 99% or more % similar, about 40% to 99% or more similar, about 50% to 99% or more similar, about 60% to 99% or more similar, about 70% to 99% or more similar, about 80% to 99% or more similar, about 85% to 99% or more similar, about 90% to 99% or more similar, or about 95% to 99% or more similar, between host and target bacteria. Substantial similarity between methylation patterns of a target host bacterium and the introduced DNA (bacteriophage DNA that has been modified) means that the introduced DNA is less degraded than that of an introduced DNA that does not share a substantially similar methylation pattern with the target host bacterium. In some embodiments, the methylation pattern of a host bacterium and a target bacterium can be identical.

In some embodiments, the invention provides a bacteriophage particle comprising bacteriophage DNA or phagemid DNA, wherein said bacteriophage DNA or phagemid DNA comprise a modified DNA methylation pattern that is substantially similar to a target host bacterium's R-M system(s) and at least one heterologous nucleic acid of interest integrated into the bacteriophage DNA (genome). Thus, for example, a bacteriophage DNA or a phagemid DNA having a modified methylation pattern (that is substantially similar to a target host bacterium's R-M system(s)) can comprise (1) a polynucleotide encoding a CRISPR array or (2) a Type II CRISPR-Cas system comprising: (a) a polynucleotide encoding a Cas9 polypeptide; (b) a polynucleotide encoding a CRISPR array; and/or c) a tracr nucleic acid. In some embodiments, the polynucleotide encoding a CRISPR array (a) and the tracr nucleic acid (c) can be fused to one another. In additional embodiments, a bacteriophage DNA or a phagemid DNA having a modified methylation pattern (that is substantially similar to a target host bacterium's R-M system(s)) can comprise (1) a polynucleotide encoding a CRISPR array or (2) a recombinant Type I CRISPR-Cas system comprising: (a) a polynucleotide encoding a CRISPR array; and/or (b) at least one polynucleotide encoding one or more Type I CRISPR polypeptides. In some embodiments, the at least one heterologous nucleic acid of interest can be integrated into the bacteriophage DNA (e.g., genome) at a dispensable site of integration or at a complemented site of integration.

As used herein, "dispensable site" means a site in the bacteriophage DNA or genome that is not necessary for maintenance of the bacteriophage genome, the generation of phage particles, and the delivery of packaged DNA. Thus, any site in a bacteriophage genome that is not required for carrying out such functions can be used as a "landing" site for integrating a nucleic acid of interest into a bacteriophage genome. Some exemplary dispensable sites in a bacteriophage genome can include, but are not limited to, (a) a phage-encoded restriction-modification system (e.g., res/mod in P1 phage), (b) a gene that blocks superinfection (e.g., simABC), (c) an inhibitor of a restriction-modification system (e.g., darA in P1 phage), (d) an insertion sequence element (e.g., IS1 in P1 phage), (e) an addiction system (e.g., phd/doc in P1 phage) or (f) any combination thereof.

A "complemented site" or a "complementable site" as used herein means an indispensible site in the bacteriophage DNA or genome that is necessary for maintenance of the bacteriophage genome, the generation of phage particles, and the delivery of packaged DNA but which can be complemented by a complementing polynucleotide encoding the nucleic acid that is disrupted by the integration (complemented site of integration) of the nucleic acid of interest. The complementing polynucleotide can be integrated into the genome of the production host bacterium or it can be comprised on a plasmid in the production host bacterium. Accordingly, when the nucleic acid of interest is integrated into a complemented site of a bacteriophage DNA, the host bacterium can comprise on a plasmid or in its genome a polynucleotide encoding a complement to the complemented site in the bacteriophage. Exemplary complemented sites can include, but are not limited to, (a) an activator of the lytic cycle (e.g., coi in P1 phage), (b) a lytic gene (e.g., kilA in P1 phage), (c) a tRNA (e.g., tRNA1,2 in P1 phage), (d) a particle component (e.g., cixL, cixR tail fiber genes in P1 phage), or (e) any combination thereof.

Thus, in some embodiments, a recombinant Type I CRISPR-Cas system, a recombinant Type II CRISPR-Cas system, a polynucleotide encoding a CRISPR array (Type I or Type II) and/or a tracr nucleic acid, an at least one polynucleotide encoding one or more Type I CRISPR polypeptides, and/or a polynucleotide encoding a Cas9 polypeptide can be integrated into a dispensable site in a bacteriophage DNA. In some embodiments, a recombinant Type I CRISPR-Cas system, a recombinant Type II CRISPR-Cas system, a polynucleotide encoding a CRISPR array (Type I or Type I) and/or tracr nucleic acid, at least one polynucleotide encoding one or more Type I CRISPR polypeptides, and/or a polynucleotide encoding a Cas9 polypeptide, can be integrated into a complemented site in a bacteriophage DNA, wherein the host bacterium to the bacteriophage comprises on a plasmid or in its genome a polynucleotide encoding the complemented site in the bacteriophage (e.g., a gene that complements the site in the phage genome into which the CRISPR polynucleotide has been integrated).

As used herein, "Type I polypeptide" refers to any of a Cas3 polypeptide, Cas3' polypeptide, a Cas3" polypeptide and any one or more of the Type I Clustered Regularly Interspaced Short Palindromic Repeats (CRISPR)-associated complex for antiviral defense ("Cascade") polypeptides. Thus, the term "Type I polypeptide" refers to the polypeptides that make up a Type I-A CRISPR-Cas system, a Type I-B CRISPR-Cas system, a Type I-C CRISPR-Cas system, a Type I-D CRISPR-Cas system, a Type I-E CRISPR-Cas system, and/or a Type I-F CRISPR-Cas system. Each Type-I CRISPR-Cas system comprises at least one Cas3 polypeptide. Cas3 polypeptides generally comprise both a helicase domain and an HD domain. However, in some Type I CRISPR-Cas systems, the helicase and HD domain are found in separate polypeptides, Cas3' and Cas3". In particular, Cas3' encodes the helicase domain whereas Cas3" encodes the HD domain. Consequently, because both domains are required for Cas3 function, Type I subtypes either encode Cas3 (I-C, I-D, I-E, I-F) or Cas3' and Cas3" (I-A, I-B).

As used herein, "Type I Cascade polypeptides" refers to a complex of polypeptides involved in processing of pre-crRNAs and subsequent binding to the target DNA in type I CRISPR-Cas systems. These polypeptides include, but are not limited to, the Cascade polypeptides of Type I subtypes I-A, I-B, I-C, I-D, I-E and I-F. Non-limiting examples of Type I-A polypeptides include Cas7 (Csa2), Cas8a1 (Csx13), Cas8a2 (Csx9), Cas5, Csa5, Cas6a, Cas3' and/or a Cas3". Non-limiting examples of Type I-B polypeptides include Cas6b, Cas8b (Csh1), Cas7 (Csh2) and/or Cas5. Non-limiting examples of Type-IC polypeptides include Cas5d, Cas8c (Csd1), and/or Cas7 (Csd2). Non-limiting examples of Type-ID polypeptides include Cas10d (Csc3), Csc2, Csc1, and/or Cas6d. Non-limiting examples of Type I-E polypeptides include Cse1 (CasA), Cse2 (CasB), Cas7 (CasC), Cas5 (CasD) and/or Cas6e (CasE). Non-limiting examples of Type I-F polypeptides include Cys1, Cys2, Cas7 (Cys3) and/or Cas6f (Csy4). Thus, in some embodiments of this invention, the Type-I Cascade polypeptides that are useful with this invention process CRISPR arrays to produce a processed RNA that is then used to bind the complex to a DNA that is complementary to a spacer in the processed RNA. In some embodiments, the Type I Cascade polypeptides that are involved in acquisition are not comprised in a nucleic acid molecule of the invention (e.g., Cas1, Cas2, Cas4). Any such subset of Cascade polypeptides from a Type I CRISPR-Cas system known in the art or those later discovered can be comprised in a nucleic acid construct of this invention. Such polypeptides can be identified, for example, via BLAST searching.

Thus, in some embodiments, a bacteriophage particle can comprise bacteriophage DNA or the phagemid DNA comprising a Type I CRISPR array and/or (i) a Cas7 (Csa2) polypeptide, a Cas8a1 (Csx13) polypeptide or a Cas8a2 (Csx9) polypeptide, a Cas5 polypeptide, a Csa5 polypeptide, a Cas6a polypeptide, a Cas3' polypeptide, and a Cas3" polypeptide (Type I-A); (ii) a Cas6b polypeptide, a Cas8b (Csh1) polypeptide, a Cas7 (Csh2) polypeptide, a Cas5 polypeptide, a Cas3' polypeptide, and a Cas3" polypeptide (Type I-B); (iii) a Cas5d polypeptide, a Cas8c (Csd1) polypeptide, a Cas7 (Csd2) polypeptide, and a Cas3 polypeptide (Type I-C); (iv) a Cas10d (Csc3) polypeptide, a Csc2 polypeptide, a Csc1 polypeptide, and a Cas6d polypeptide, and a Cas3 polypeptide (Type I-D); (v) a Cse1 (CasA) polypeptide, a Cse2 (CasB) polypeptide, a Cas7 (CasC) polypeptide, a Cas5 (CasD) polypeptide, a Cas6e (CasE) polypeptide, and a Cas3 polypeptide (Type I-E); or (iv) a Cyst polypeptide, a Cys2 polypeptide, a Cas7 (Cys3) polypeptide, Cas6f polypeptide and/or a Cas3 polypeptide (Type I-F). In representative embodiments, a bacteriophage particle can comprise bacteriophage DNA or phagemid DNA comprising a Type I CRISPR array and at least one polynucleotide encoding one or more Type I-E Cascade polypeptides (i.e., a Cse1 (CasA) polypeptide, a Cse2 (CasB) polypeptide, a Cas7 (CasC) polypeptide, a Cas5 (CasD) polypeptide, a Cas6e (CasE) polypeptide, a Cas3 polypeptide).

"Cas9 nuclease" refers to a large group of endonucleases that catalyze the double stranded DNA cleavage in the CRISPR-Cas Type II system. These polypeptides are well known in the art and many of their structures (sequences) are characterized (See, e.g., WO2013/176772; WO/2013/188638). The domains for catalyzing the cleavage of the double stranded DNA are the RuvC domain and the HNH domain. The RuvC domain is responsible for nicking the (−) strand and the HNH domain is responsible for nicking the (+) strand (See, e.g., Gasiunas et al. *PNAS* 109(36):E2579-E2586 (Sep. 4, 2012)).

In some embodiments, a CRISPR array, a tracr nucleic acid, a polynucleotide encoding a Cas9 polypeptide, a polynucleotide encoding a Cas3 polypeptide, a polynucleotide encoding a Cas3' polypeptide, a polynucleotide encoding a Cas3" polypeptide, and/or an at least one polynucleotide encoding one or more Type I CRISPR polypeptides can be operably linked to a promoter. In some embodiments, when the at least one polynucleotide comprises at least two polynucleotides encoding one or more Type I CRISPR polypeptides, the at least two polynucleotides can be operably linked to a single promoter or to separate promoters.

In some embodiments, a CRISPR array and a tracr nucleic acid can be operably linked to a single promoter or to different promoters. In some embodiments, when the CRISPR array and the tracr nucleic acid are fused to one another, the fused polynucleotide encoding the CRISPR array and the tracr nucleic acid can be operably linked to a single promoter. In some embodiments, at least two of the at least one polynucleotide encoding one or more Type I CRISPR polypeptides can be fused to form a single polynucleotide, which can be optionally operably linked to a promoter. In some embodiments, the Type 1 Cascade polypeptides can be comprised in a single operon, optionally operably linked to a promoter. In further embodiments, a polynucleotide encoding a Cas3 polypeptide, a Cas3' polypeptide and/or a polynucleotide encoding a Cas3" polypeptide can be fused to a polynucleotide encoding a Type I Cascade polypeptide, said fused polynucleotides can be operably linked to a promoter, which upon expression produce a fused polypeptide. In a representative embodiment, a polynucleotide encoding a Cas3 polypeptide can be fused to a polynucleotide encoding a Cse1 polypeptide.

Additionally, the present invention provides bacteriophage particles produced by any of the methods of the invention. In some embodiments, the bacteriophage particle comprises bacteriophage DNA. In other embodiments, the bacteriophage particle comprises phagemid DNA. In further embodiments, the bacteriophage particle does not comprise phagemid DNA. In some embodiments, the present invention provides a bacteriophage particle comprising bacteriophage DNA or phagemid DNA, which comprise a modified DNA methylation pattern that is substantially similar to a target host bacterium's restriction-modification system(s).

Additionally provided herein, are methods of selectively killing bacteria (i.e., target bacteria) using the bacteriophage particles of the invention engineered to comprise bacteriophage DNA or phagemid DNA comprising at least a CRISPR array of a CRISPR-Cas system. In some embodiments, when the bacteriophage DNA and/or phagemid DNA comprises only a CRISPR array, the target bacterial host can comprises an active CRISPR-Cas system (e.g., at least a tracr nucleic acid and a Cas9 polypeptide (Type II CRISPR-Cas system), or at least a Cas3 polypeptide, a Cas3' polypeptide and/or a Cas3" polypeptide and at least a subset of the Cascade polypeptides (a Type I CRISPR-Cas system)). In other embodiments, the bacteriophage DNA and/or phagemid DNA of the bacteriophage particles comprises a CRISPR array, a tracr nucleic acid and/or a polynucleotide encoding a Cas9 polypeptide; or a CRISPR array, a polynucleotide encoding at least at least a Cas3 polypeptide, a Cas3' polypeptide and/or a Cas3" polypeptide and a polypeptide encoding at least a subset of the Cascade polypeptides.

In some embodiments, the bacteriophage DNA or the phagemid DNA used for selectively killing bacteria comprises a methylation pattern that is substantially similar to that of the target bacteria, either naturally or modified as described herein.

Accordingly, the present invention provides a method of selectively killing at least one target bacterial species or strain comprising: contacting said at least one target bacterial species or strain with a bacteriophage particle of the invention comprising bacteriophage DNA or phagemid DNA comprising at least one heterologous polynucleotide encoding a CRISPR array or a recombinant CRISPR-Cas system comprising a CRISPR array, wherein the CRISPR array comprises at least one spacer having substantial complementarity (e.g., at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% complementarity, or any range or value therein) to a target DNA in said at least one target bacterial species or strain. In some embodiments, said bacteriophage DNA or phagemid DNA comprises at least one spacer having 100% complementarity to a target DNA in said at least one target bacterial species or strain.

In some embodiments, wherein the bacteriophage particles comprise bacteriophage DNA or phagemid DNA comprising only a Type I CRISPR array or a Type II CRISPR array, the target bacterial host can be any bacterial species or strain that has an active endogenous CRISPR-Cas Type I or Type II system. Exemplary bacterial species or strain having an active CRISPR-Cas Type I or Type II system include *Francisella tularensis* (Type II-A), *Mycobacterium tuberculosis* (Type I, III), *Novicida meningitidis* (Type II-C), *Pseudomonas aeruginosa* (Type I-F), *Staphylococcus aureus* (Type II-A), *Streptococcus pyogenes* (Type II-A), *Pectobacterium atrosepticum* (Type I-F), and/or *Streptococcus thermophilus* (Type II-A). In other embodiments, wherein the bacteriophage particles comprise bacteriophage DNA or phagemid DNA comprising a recombinant Type I CRISPR-Cas system or a recombinant Type II CRISPR-Cas system, the host bacteria may or may not have an endogenous CRISPR-Cas Type I or Type II system and therefore the host bacteria can be any bacterial host that comprises the target DNA.

In exemplary embodiments, the target DNA can be unique to the target strain, species, or genera; can be shared between different strains, species, or genera; can be present in most bacteria; and/or can be within an antibiotic resistance gene, virulence gene, and/or pathogenicity island. In some embodiments, the bacteriophage particle can be produced or generated in a different bacterial species or strain than the target bacterial species or strain.

In some embodiments, a bacterium can be targeted in/on, for example, humans, animals, plants, and in agriculture, medical and/or industrial settings (e.g., fermentation). In some embodiments, the bacteriophage particles of the invention can be used in methods to completely eliminate a bacterial strain or to titrate its presence.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Modification of Methylation Activity of Host Bacteria and Methylation Pattern of Phage DNA The methylation pattern of a host production strain, such as *Escherichia coli* MG1655 or *Bacillus subtilis* 168, is altered by deleting its endogenous restriction-modification systems and introducing heterologous methyltransferase genes. The restriction-modification genes are identified through means that are known in the art, such as through the online REBASE database (Roberts et al. *Nucleic Acids Res* 43:D298-D299. http://dx.doi.org/10.1093/nar/gku1046). These restriction-modification systems can be deleted using standard recombineering strategies known in the art. Once deleted, foreign methyltransferase genes are inserted into replicative plasmids or recombineered into the host genome under the control of a constitutive or inducible promoter. These genes are obtained directly from the target strain using the natural sequence or a sequence codon-optimized for the production host. Alternatively, heterologous methyltransferase genes can be used to confer a similar methylation patterns as the target strain. The methylation patterns conferred by individual methyltransferases are then assessed using established DNA sequencing technologies such as PacBio SMRT sequencing (O'Loughlin et al. *PLoS One.* 2015:e0118533.). Once generated, the production strain is used to produce bacteriophage particles for DNA delivery into the target strain.

M13 phage and P1 phage are used to demonstrate the impact of methylation on the delivery of phagemids (M13) and phage genomes (P1). The M13 phage has an established phagemid system based on its extensive use for phage display (Pande et al. *Biotechnol. Adv.* 28, 849-858 (2010)). The system is based on using a helper plasmid to efficiently package plasmids container the f1 origin. The cells then constitutively produce phage particles that can be collected and administered to target strains. The particles recognize the F1 pilus, which requires strains to carry the F plasmid. The P1 phage is a well-characterized phage that is much more complex than M13 (Lobocka et al. *J Bacteriol.* 186, 7032-7068 (2004)). In order to drive the lytic cycle for the P1 phage, we expressed the coi gene from a separate plasmid.

Demonstrate Improved Delivery for M13 Phagemid:

The titer of M13 phages prepared in *E. coli* with all (MG1655), some (TOP10), or none (MG1655 Δdam Δdcm ΔhsdRMS) of its R-M systems intact are tested. The phages are tested in MG1655 Δdam Δdcm ΔhsdRMS to evaluate potential variability in titers, and then in MG1655 to evaluate the impact of DNA methylation. The antibiotic resistance marker in the phagemid serves as a readout of delivery based on the number of antibiotic resistant colonies. Delivery efficiency is expected to be similar going into MG1655 Δdam Δdcm ΔhsdRMS but to be greatly elevated for MG1655 when going into MG1655.

Delivery of M13 Phagemid into Enterohaemorrhagic *E. coli*:

M13 phagemid is delivered to a strain of EHEC (enterohaemorrhagic *E. coli*). EHEC possesses more R-M systems than MG1655 and has shown reduced uptake of the M13 phagemid. Type II methyltransferases from EHEC are expressed in the MG1655 Δdam Δdcm ΔhsdRMS strain and M13 particles are generated containing the phagemid. The particles are then administer to MG1655 Δdam Δdcm ΔhsdRMS and an EHEC strain harboring the F plasmid and the number of colonies that are antibiotic resistant counted. The introduced methyltransferases are expected not to affect the number of MG1655 Δdam Δdcm ΔhsdRMS colonies (indicating similar particle titers) but are expected to greatly increase the number of EHEC colonies (indicating improved efficiency due to the methyltransferases).

Demonstrate Improved Delivery for P1 Phage:

A similar approach to that described above will be followed using the P1CM phage. The major difference is that the dmt methylase gene in the P1 genome additionally will be disrupted. We have already tried generating P1 lysogens in EC135, which led to cell lysis in liquid culture. It is expected that some amount of methylation is required; however, with this methylation in place, additional types of methylation can be introduced to improve the delivery efficiency of the P1 genome.

Example 2. Bacteriophage and Phagemid DNA Comprising CRISPR-Cas Systems for Selectively Killing Bacteria P1 phage and the M13 phagemid are used to test the use of bacteriophage and phagemid DNA as carriers of CRISPR-Cas systems for the selective killing of bacteria. The P1 phage is a classic model of phage biology (Lobocka et al. *J. Bacteriol.* 186, 7032-7068 (2004)), and is commonly used to transduce pieces of genomic DNA (Ikeda & Tomizawa. *J. Mol. Biol.* 14, 85-109 (1965)). A phagemid has been developed for P1 (Westwater, *Microbiol.* Read. Engl. 148, 943-950 (2002) and has been used to deliver DNA to varying gram-negative bacteria and as a means to transduce large DNA libraries (Kittleson et al. *ACS Synth. Biol.* 1, 583-589 (2012); Kaiser & Dworkin, *Science* 187, 653-654 (1975). We currently have a strain with the wild-type P1 phage and a separate plasmid that inducibly expresses the coi gene. The P1 phage is lysogenic under normal growth conditions. Expression of the coi gene drives the phage into the lytic cycle, creating the phage particles.

The M13 phagemid relies on a phagemid containing the F1 origin of replication and a helper plasmid encoding the rest of the phage machinery. Infection by M13 requires the F-pilus, which is normally expressed from the F plasmid found in some *E. coli* strains. M13 has been a standard platform for phage display (Pande et al. *Biotechnol. Adv.* 28, 849-858 (2010)).

Targeted Killing with a Type I CRISPR-Cas System:

The entire Type I-E CRISPR-Cas system from *E. coli* or the Type I-C CRISPR-Cas system from *Bacillus halodurans* is encoded into the M13 phagemid and used to demonstrate targeted killing of *E. coli*. An antibiotic resistance gene present in the target strain is used to demonstrate selective killing using this system. To ensure efficient infection, the target strain also encodes the F plasmid. The phage particles are administered to the target cells and the cells are plated to count viable colonies. It is expected that delivery of the system will result in massive reductions in the number of colonies in comparison to no phage or a non-targeting phage.

Identifying Integration Sites in the P1 Genome:

Using homologous recombination an antibiotic resistance marker is incorporated into different locations in the P1 genome. The locations include dispensable and/or complemented sites such as, for example (a) a phage-encoded restriction-modification system (e.g., res/mod in P1 phage), (b) a gene that blocks superinfection (e.g., simABC), (c) an inhibitor of a restriction-modification system (e.g., darA in P1 phage), (d) an insertion sequence element (e.g., IS1 in P1 phage), (e) an addiction systems (e.g., phd/doc in P1 phage), (f) an activator of the lytic cycle (e.g., coi in P1 phage), (g) a lytic gene (e.g., kilA in P1 phage), (h) a tRNA (e.g., tRNA1,2 in P1 phage), (i) a particle component (e.g., cixL, cixR tail fiber genes in P1 phage), or (j) any combination thereof.

For the complemented sites, the deleted gene(s) are cloned into the pBAD18 inducible expression system. In each case, cell lysis is assessed following induction (a sign that the lytic cycle is still active) and then the number of transducing particles is measured based on antibiotic resistant colonies following transduction. All of this work is performed in *E. coli*.

Equipping P1 Phage with Components of a CRISPR-Cas System:

Three approaches to be taken:

1. Equipping P1 with a repeat-spacer-repeat for delivery to strains expressing a Type I or Type II CRISPR-Cas system.
2. Equipping P1 with CRISPR-Cas9 (for example, Sth1 Cas9 and a sgRNA (CRISPR array fused to a tracr nucleic acid)).
3. Equipping P1 with the *E. coli* Type I-E system or the *B. halodurans* Type I-C system.

For each approach, the construct is integrated using homologous recombination with an antibiotic resistance marker. The CRISPR array is designed to target a separate antibiotic resistance marker present in a target strain but not the production strain. The phage particles are then administered to the target strain and the number of viable colonies counted. It is expected that the designed phages will greatly reduce the number of viable colonies in comparison to no phage or a non-targeting phage.

Efficient Cross-Strain and Cross-Species Delivery and Killing:

One of the designed phages (e.g. P1) is generated in a production strain of *E. coli* (e.g. MG1655 Δdam Δdcm ΔhsdRMS) with a modified methylation pattern. This is accomplished by introducing heterologous methyltransferase genes from a target strain (e.g. *Klebsiella pneumoniae, Psuedomonas aeruginosa, E. coli* O157:H7) or methyltransferases from other strains that are known to generate similar methylation patterns (e.g. methyltransferases listed in the online REBASE database). The bacteriophage is designed to encode a CRISPR array that is compatible with the endogenous CRISPR-Cas system (e.g. the Type I-F system in *Pseudomonas aeruginosa*) and targets at least one PAM-flanked site in the genome. Alternatively, the bacteriophage is designed to encode a complete CRISPR-Cas system (e.g.

the Type I-E Cascade genes and cas3 and a Type I-E CRISPR array). The phage particle is then generated (e.g., by inducibly expressing coi for P1 or through constitutive production of filamentous phage for M13) and used to infect different target strains that are distinct from the host. For instance, the phages are used to deliver the DNA to *Klebsiella pneumoniae* or *Shigella flexneri*. Delivery is performed by introducing a selectable marker and at different multiplicities of infection for the phage. The extent of killing is measured based on halted increase in turbidity of a liquid culture or a reduction in the number of colony-forming units. The target strain is selectively killed using the phage while non-targeted strains are spared from killing. Furthermore, the killing efficiency is enhanced for bacteriophages generated in the production strain with its methylation pattern engineered to be substantially similar to the target strain (versus the production strain without any modifications to its R-M systems or any added methyltransferases).

Methods for P1 Phage

A. Delivery Through Phagemids
1. P1 Phagemid is a plasmid that encodes the following components from the P1 bacteriophage genome (coi, cin, repL, pacA genes).
2. The phagemid is engineered to introduce the CRISPR-Cas system components (Either the CRISPR array alone, or with the cas genes) through Gibson cloning
3. Once the P1 phagemid-CRISPR-Cas is constructed, it is packaged to the P1 bacteriophage using the protocol phagemid-CRISPR-Cas packaging.
4. Phagemid-CRISPR-Cas is used to target and eliminate bacterial strains using the targeting protocol.

B. Delivery Through Engineered P1 Bacteriophage
1. P1 bacteriophage is engineered by cloning the CRISPR-Cas system components into its genome in a specified location chosen not to disrupt the bacteriophage function, these locations are, for example:
   a. In place of the coi gene (responsible for triggering the lytic cycle).
   b. In place of both the coi gene and imcB gene (coi-icmB; both help in triggering the lytic cycle).
   c. With an inclusion site.
2. coi gene is amplified from P1 bacteriophage genome and cloned into pBad18 plasmid.
3. When the P1-CRISPR-Cas phage and the pBad18-coi coexist in a strain, the expression of coi is induced to produce phage particles following the protocol P1-CRISPR-Cas packaging.
4. The produced lysate is expected to contain 100% P1-CRISPR-Cas phages and is used for killing the targeted strain following the protocol Targeting.

Figure 1:
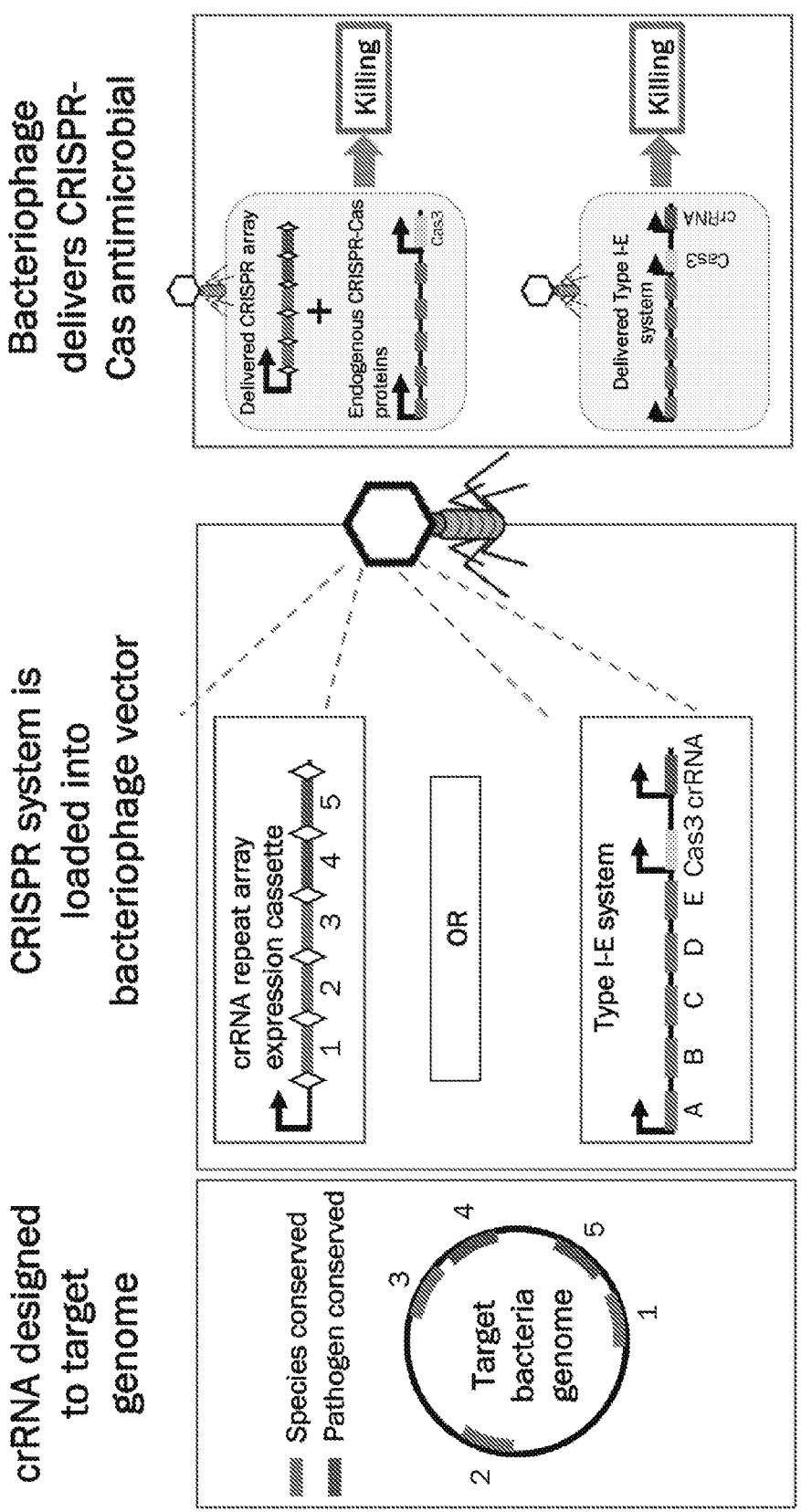
FIG. 1 provides an overview of general process of generating bacteriophage particles as a platform for delivery of CRISPR antimicrobials.

C. CRISPR-Cas Components Cloning
1. Generally CRISPR-Cas components need to be cloned to either the P1 bacteriophage genome or the phagemid. The component to be cloned depends on the target strain.
2. If the target strain contains an active CRISPR-Cas system, the component to clone is only a DNA expressing genome-targeting CRISPR RNAs (e.g., CRISPR arrays, repeat spacer-repeat). See, FIG. 1 schematic.
3. If the target strain does not contain an active CRISPR-Cas system, the components to clone include both the DNA for the cas genes (e.g., Cas9, Cas3, Cas3', Cas3", and/or Cascade polypeptides) and the genome-targeting CRISPR RNAs (e.g., CRISPR array, tracr nucleic acid). See, FIG. 1 schematic.
4. Cloning into the phagemid is conducted using Gibson cloning scheme. Cloning to P1 bacteriophage is done using homology recombination.

General Protocols

A. Phagemid-CRISPR-Cas Packaging:
1. Phagemid-CRISPR-Cas is transformed to strain K1739 (*E. coli* strain) harboring temperate P1 bacteriophage.
2. The strain is then grown in liquid culture shaking overnight at 37 C.
3. Next day, the culture is back diluted 1:100 and shaken at 37 C for 1-2 hours.
4. Arabinose is added to the culture to induce the expression of the coi gene on the phagemid and induce the lytic cycle is bacteriophage P I Shaking continues for an additional 5 hours until lysis is verified by visually inspecting the culture.
5. Chlorofolin is added to the lysed culture and mixed by inverting up and down. This ensures the death of any unlysed cells.
6. Cell debris is collected by centrifugation for 10 minutes and then the supernatant is collected as the lysate. The lysate contains phage particles containing a mix of the original P1 bacteriophage DNA and phagemid-CRISPR-Cas.

B. P1-CRISPR-Cas Packaging:
1. pBad18 plasmid encoding coi gene is transformed to strain K1739 (*E. coli* strain) harboring engineered temperate P1-CRISPR bacteriophage.
2. The strain is then grown in liquid culture shaking overnight at 37 C.
3. Next day, the culture is back diluted 1:100 and shaken at 37 C for 1-2 hours.
4. Arabinose is added to the culture to induce the expression of the coi gene on the phagemid and induce the lytic cycle is bacteriophage P1. Shaking continues for an additional 5 hours until lysis is verified by visually inspecting the culture.
5. Chloroform is added to the lysed culture and mixed by inverting up and down. This ensures the death of any non-lysed cells.
6. Cell debris is collected by centrifugation for 10 minutes and then the supernatant is collected as the lysate. The lysate contains only P1-CRISPR bacteriophage that is capable of delivering the CRISPR-Cas components.

C. Targeting
1. Strain to be targeted is grown in liquid culture by shaking overnight at 37 C.
2. Next day, cells are collected from the culture by centrifugation and are resuspended in LB media supplemented with CaCl2 and MgSO4.
3. The culture is adjusted to an OD of 2 and then it is infected by the lysate at a pre-calculated multiplicity of infection (i.e., ratio of agents (e.g. phage, virus, and the like) to infection targets; MOI) that maximizes the probability of all cells being infected by at least one phage particle.
4. Infection is conducted by mixing the culture with the lysate through inverting the tube.
5. Infected cells are incubated with the lysate at 37 C for 30 minutes and then shaken at 37 C for 1 hour.
6. Cells are then plated at different dilutions and incubated overnight at 37 C.
7. Colony forming units are counted the next day.

Example 3. Engineering Broad Host Bacteriophages for Multi-Species DNA Delivery and CRISPR Antimicrobials CRISPR (Clustered Regularly Interspaced Short Palindromic Repeats) and their Cas (CRISPR associated) proteins have proven to be powerful agents for antimicrobials and potential replacements for broad-spectrum antibiotics (Gomaa, A. A. et al. *MBio* 5, e00928-913 (2014); Bikard, D. et al. *Nature Biotechnology* 32, 1146-1150 (2014); Citorik et al. *Nat. Biotechnol.* 32, 1141-1145 (2014)). These systems naturally function as RNA-guided immune systems in bacteria and archaea to recognize and cleave complementary genetic material (Brouns et al. *Science* 321, 960-964 (2008); Marraffini et al. *Science* (New York, N.Y.) 322, 1843-1845 (2008); Garneau. et al. *Nature* 468, 67-71 (2010); Edgar et al. *J. Bacteria* 192, 6291-6294 (2010); Manica et al. *Mol. Microbia* 80, 481-491 (2011)). Designing guide RNAs to target the bacterial genome can cause irreversible DNA damage at the target site, resulting in sequence-specific cell killing (Gomaa, A. A. et al. *MBio* 5, e00928-913 (2014); Bikard, D. et al. *Nature Biotechnology* 32, 1146-1150 (2014); Citorik et al. *Nat. Biotechnol.* 32, 1141-1145 (2014)). Furthermore, designing the guide RNAs to target plasmids harboring multidrug resistance can sensitize the bacterium to antibiotics (Bikard, D. et al. *Nature Biotechnology* 32, 1146-1150 (2014)).

To exert their antimicrobial activity, CRISPR-Cas systems must be delivered into the bacterial cytoplasm. Delivery strategies to date have overwhelmingly relied on encoding the system within DNA packaged by temperate or filamentous bacteriophages, either within the bacteriophage genome or within plasmids called phagemids that contain packaging signals for the bacteriophage particle (Bikard et al. *Nature Biotechnology* 32, 1146-1150 (2014); Citorik et al. *Nat. Biotechnol.* 32, 1141-1145 (2014); Yosef et al. *Proceedings of the National Academy of Sciences* 112, 7267-7272 (2015)). In these examples, delivery of the CRISPR-Cas system resulted in potent killing or plasmid removal, or immunized the infected cells against the transfer of antibiotic resistance. While these have been promising demonstrations, the bacteriophages are all associated with a narrow host range that is limited to an individual species or strain. As a result, each delivery platform restricts the range of bacteria to which CRISPR may be targeted. To fully realize the potential of CRISPR antimicrobials, generalized delivery vehicles are needed that can reach a much broader host range.

Here, the broad-host, temperate bacteriophage P1 is engineered for DNA delivery and CRISPR antimicrobials. P1 functions as a temperate bacteriophage, where the about 90-kb genome exists as an extrachromosomal, single-copy plasmid in its lysogenic state (Lobocka et al. *J. Bacteriol.* 186, 7032-7068 (2004)). Importantly, P1 has been shown to inject its genome into a remarkably broad range of gram-negative bacteria spanning diverse bacteria within the phylum proteobacteria (Westwater et al. *Microbiology* 148, 943-950 (2002)). Furthermore, P1 has been a standard platform for DNA delivery through the rare packaging of genomic DNA or phagemids (Westwater et al. *Microbiol.* 148, 943-950 (2002); Ikeda et al. *J. Mol. Biol.* 14, 85-109 (1965); Thomason et al. *Curr Protoc Mol Biol* Ch. 1, Unit 1.17 (2007); Kittleson et al. *ACS synthetic biology* 1, 583-589 (2012); Ikeda et al. *J. Mol. Biol.* 14, 85-109 (1965); Thomason et al. *Curr Protoc Mol Biol* Ch. 1, Unit 1.17 (2007); Kittleson et al. *ACS synthetic biology* 1, 583-589 (2012)). We found that the P1 genome was more efficiently delivered than a P1 phagemid and could accommodate synthetic DNA in at least three distinct landing sites in its genome. The engineered genome is shown to be efficiently delivered to *Escherichia coli* and *Shigella flexneri*, thereby eliciting sequence-specific killing upon delivering a designed CRISPR-Cas system. Engineering the P1 genome therefore represents a promising strategy to deliver CRISPR antimicrobials to diverse bacteria.

Strains, Plasmids, and Bacteriophages Construction.

All strains, plasmids, and bacteriophages used in this work are reported in Tables 1 and 2.

TABLE 1

Strains

| Strain | Genotype |
|---|---|
| BW25113 | *Escherichia coli* K12 F– DE(araD-araB)567 lacZ4787(del)(::rrnB-3) LAM– rph-1 DE(rhaD-rhaB)568 hsdR514 |
| BW25113 Δcas3 | BW25113 [Δcas3 Pcse1]::[PJ23119] |
| BL21(D3) | *Escherichia coli* B F– ompT gal dcm lon hsdS$_B$(r$_B^-$ m$_B^-$) λ(DE3 [lacI lacUV5-T7 gene 1 ind1 sam7 nin5]) |
| KL739 | *Escherichia coli* thr-1 leuB6(Am) fhuA21 lacY1 glnX44(AS) λ$^-$ rfbC1 thiE1 P1kc+ pro-89 P1 lysogen |
| MG1655 | *Escherichia coli* K-12 F$^-$ λ$^-$ ilvG$^-$ rfb-50 rph-1 |
| MG1655 ΔdamΔdcmΔhsdRMS | *Escherichia coli* MG1655 ΔdamΔdcmΔhsdRMS |
| *Shigella flexneri* | ATCC #12022 and ATCC #700930 |

TABLE 2

Plasmids, and bacteriophages

| Plasmid | Description | Resistance marker |
|---|---|---|
| pBAD18 | L-arabinose-inducible plasmid with araC regulator | ampicillin |
| pcoi | PBAD18 vector with coi insert | Ampicillin |
| pKD13 | Plasmid encoding kanamycin resistance gene flanked by FRT sites | Kanamycin |
| pKD13ΔSalI | pKD13 plasmid missing SalI restriction site | Kanamycin |
| pKD13ΔSalI-1E | pKD13ΔSalI with CRSIPR locus insert containing 1 repeat, no spacers | Kanamycin |
| pKD13ΔSalI-1E-ftsA | pKD13ΔSalI-1E encoding a spacer to target ftsA gene | Kanamycin |
| pKD3 | Plasmid encoding cat cassette flanked by FRT sites | Chloramphenicol |
| pKD46 | L-arabinose-inducible expression of λ-red genes on a plasmid with a heat-sensitive origin-of-replication | Ampicillin |
| pcas3 | pBAD33 with constitutively expressed cas3 gene | Chloramphenicol |
| P1 phagemid | P15a vector with arabinose inducible coi gene in addition to gfp, cin, repL, and pacA genes. | Chloramphenicol |
| P1-ΔimcB/coi::kanR | P1 bacteriophage with kanamycin resistance gene inserted in place of the imcB/coi operon | Kanamycin |
| P1-ΔimcB/coi::cmR | P1 bacteriophage with cat cassette inserted in place of the imcB/coi operon | Chloramphenicol |
| P1-ΔsimABC::kanR | P1 bacteriophage with kanamycin resistance gene inserted in place of the simABC operon | Kanamycin |
| P1-ΔIS1::kanR | P1 bacteriophage with kanamycin resistance gene inserted in place of the IS1 site | Kanamycin |

TABLE 2-continued

Plasmids, and bacteriophages

| Plasmid | Description | Resistance marker |
|---|---|---|
| P1-ΔimcB/coi::kanR-ftsA | P1 bacteriophage with kanamycin resistance gene and Type I-E CRISPR locus encoding ftsA targeting spacer inserted in place of the imcB-coi operon | Kanamycin |
| P1-ΔsimABC::kanR-ftsA | P1 bacteriophage with kanamycin resistance gene and Type I-E CRISPR locus encoding ftsA targeting spacer inserted in place of the simABC operon | Kanamycin |
| P1-ΔIS1::kanR-ftsA | P1 bacteriophage with kanamycin resistance gene and Type I-E CRISPR locus encoding ftsA targeting spacer inserted in place of the IS1 site | Kanamycin |
| M13KO7 | See NEB cat# N0315S. Briefly, M13 bacteriophage with the following mutations: (1) Met40Ile in gII, (2) insertion of both the p15A origin and the kanamycin resistance gene from the transposon Tn903 inserted in the M13 origin of replication | Kanamycin |

The pKD13ΔSalI plasmid was generated by digesting the pKD13 plasmid (Datsenko et al. *Proc. Natl. Acad. Sci. U.S.A.* 97, 6640-6645 (2000)) with SalI restriction enzyme, blunt-ended using Pfu polymerase, and ligated using T4 DNA ligase (NEB).

To generate the pKD13ΔSalI-1E plasmid, the pKD13ΔSalI backbone was amplified by PCR using primers pKD13_1Earray.fwd/pKD13_1Earray.rev. Chemically-synthesized linear, double-stranded DNA (e.g. a gBlocks®) encoding a strong constitutive promoter (J23100), a single Type I-E CRISPR repeat modified with a KpnI restriction site and an XhoI restriction site, and double terminator was ordered from IDT and amplified by PCR using 1Earray_pKD13.fwd/1Earray_pKD13.rev. Gibson assembly (Gibson, D. G. *Meth. Enzymol* 498, 349-361 (2011)) was then used to ligate the amplified gBlocks® to the pKD13ΔSalI backbone upstream of the kanamycin resistance cassette. The KpnI/XhoI restriction sites were included in the gBlocks® to allow the sequential insertion of engineered repeat-spacer pairs 1. This approach was followed to insert an engineered spacer targeting the essential ftsA gene in *E. coli* into pKD13ΔSalI-1E in order to generate the pKD13ΔSalI-1E-ftsA plasmid.

To generate the pcoi plasmid, pBAD18 plasmid (Guzman et al. *J. Bacteriol.* 177, 4121-4130 (1995)) was linearized by NheI/SacI. The coi gene was then PCR amplified using the primers coi.fwd/coi.rev from the P1 lysogen isolated using Zymo Plasmid DNA purification kit. These primers introduced NheI and SacI sites on both ends of the amplified coi gene. The PCR product was then digested by NheI/SacI and ligated to the linearized pBAD18 plasmid downstream the pBAD promoter.

To integrate the kanamycin resistance cassette into the P1 bacteriophage genome, the kanamycin resistance cassette was PCR-amplified from pKD13 using primers with the P1 genome specific homology regions at the 5' end. The resulting linear PCR product was integrated through λ-red mediated recombination into the P1 bacteriophage lysogen present in *E. coli* KL739 strain harboring the pKD46 plasmid19. *E. coli* KL739 strain was chosen because it has a R-M system that is substantially similar to that of the target bacteria (e.g., Bw25113, BL21, MG1655, or *Shigella*).

The same approach was followed for integrating the chloramphenicol resistance gene (cat) or the Type I-E CRISPR array/ftsA spacer into the P1 bacteriophage genome. In these cases, the chloramphenicol (cm) resistance cassette was amplified from the pKD3 plasmid (Datsenko et al. *Proc. Natl. Acad. Sci. U.S.A.* 97, 6640-6645 (2000)) and the Type I-E CRISPR array ftsA spacer was amplified along with the kanamycin resistance cassette from the pKD13ΔSalI-1E-ftsA plasmid. All plasmids have been screened by colony PCR and verified by sequencing.

Growth Conditions.

All strains were cultured in 15 mL Falcon™ round bottom tubes containing LB medium (10 g/L tryptone, 5 g/L yeast extract, 10 g/L sodium chloride) with appropriate antibiotics at 37° C. or 30° C. and 250 rpm. The same strains were plated on LB agar (Luria Broth media with 1.5% agar) supplemented with appropriate antibiotics and incubated at 37° C. Antibiotics were administered at the following final concentrations: 50 μg/ml kanamycin, 50 μg/ml ampicillin, and 34 μg/ml chloramphenicol. L-arabinose was administered at 0.2% to induce expression of pcoi.

Transduction Assays.

Freezer stocks of *E. coli* and *Shigella* strains were streaked onto LB agar and individual colonies isolated. Individual colonies were inoculated into 3 ml of LB media and shaken overnight at 37° C. and 250 rpm. The cultures then were pelleted and resuspended in 1 mL of the infection medium and the ABS600 was measured on a Nanodrop 2000c spectrophotometer (Thermo Scientific). Based on the ABS600 value and the assumption that ABS600 of 1 is equivalent to $8\times10^8$ cells/mL, the number colony faulting units per mL (CFU/mL) was determined. The cultures were then mixed by pipetting with the bacteriophage lysate at a specific MOI based on the experiment. In some cases, the cultures needed to be diluted in the infection medium to an appropriate CFU/mL for the targeted MOI. The culture/bacteriophage mixture was then shaken 60-90 minutes at 37° C. and 250 rpm. Finally, 200-300 μl of appropriate dilutions of the culture/bacteriophage mixture were plated on LB agar supplemented with the appropriate antibiotics and incubated at 37° C. overnight. The number of colonies grown on the plate per mL of bacteriophage lysate added was considered an indication of the delivery efficiency.

For the superinfection experiments, freezer stocks of *E. coli* harboring either P1-ΔimcB/coi:kan$^R$, or P1-ΔsimABC:kan$^R$ were streaked to isolation on LB agar supplemented with the appropriate antibiotic. Individual colonies were inoculated in 3 mL of LB media supplemented with the appropriate antibiotic and shaken overnight at 37° C. and 250 rpm.

Following the same transduction protocol stated above, the cultures were infected with P1-ΔimcB/coi:cm$^R$ and plated on LB plates supplemented with kanamycin, chloramphenicol, or both.

Phage Particle Production.

Freezer stocks of strains harboring the P1 lysogen and either the pcoi plasmid or the P1 phagemid were streaked to isolation on LB agar. Individual colonies were inoculated into 3 ml of LB media and shaken overnight at 37° C. and 250 rpm. The overnight cultures were back diluted 1:100 in 5 mL of P1 lysis media (PLM; LB media containing 100 mM MgCl2 and 5 mM CaCl2) ((Westwater et al. *Microbiology* 148, 943-950 (2002)) and allowed to grow to ABS600 about 0.6-0.8 by shaking at 37° C. and 250 rpm. L-arabinose was then added to induce the expression of the coi gene and trigger the P1 bacteriophage lytic cycle. The cultures were left to lyse for 4-6 hours by shaking at 37° C. and 250 rpm. Lysed cultures were then transferred to 15 mL Eppendorf conical tubes, chloroform was added to a final concentration of 2.5 wt % and mixed by inverting the tube several times. Lysed cell debris was then pelleted by centrifugation for 10 minutes at 4° C. and the supernatant was placed into fresh 15 mL Eppendorf tubes. All lysates were stored at 4° C.

A. Extent of Methylation of Bacteriophage-Packaged DNA Differs when Produced in Strains with Methyltransferase Genes Versus without Methyltransferase Genes.

Figure 2A:
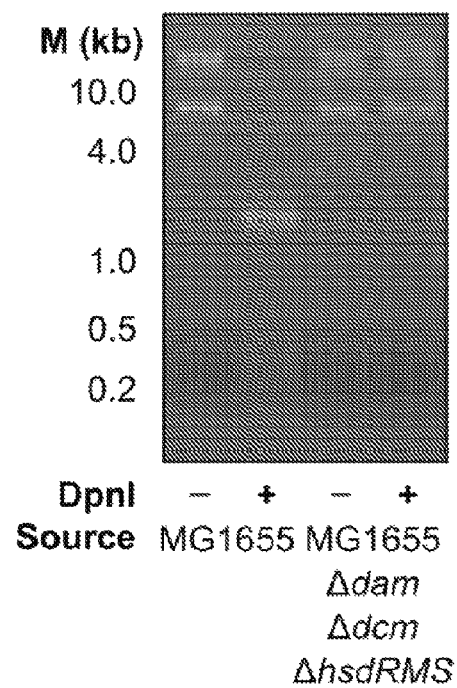
FIGS. 2A-2B show that plasmid DNA from bacterial strains without methyltransferases is not degraded by restriction enzymes targeting methylated DNA. DNA from E. coli strain MG1655 is in the left two lanes and DNA from E. coli strain MG1655 Δdam Δdcm ΔhsdRMS (lacking methyltransferase genes) is in the right two lanes (FIG. 2A). The DNA was incubated with (+) or without (−) DpnI.

Plasmid DNA for pCas3 was extracted from MG1655 and MG1655 lacking the methyltransferase genes. The DNA was then incubated with (+) or without (−) DpnI, a restriction enzyme that only cleaves the methylated sequence GAmTC. The samples were then resolved by agarose gel electrophoresis along with a DNA size marker. The data show that the plasmid DNA extracted from MG1655 undergoes cleavage by DpnI (FIG. 2A, left two lanes), whereas DNA from MG1655 lacking the methyltransferase genes does not undergo cleavage (FIG. 2A, right two lanes).

Figure 2B:
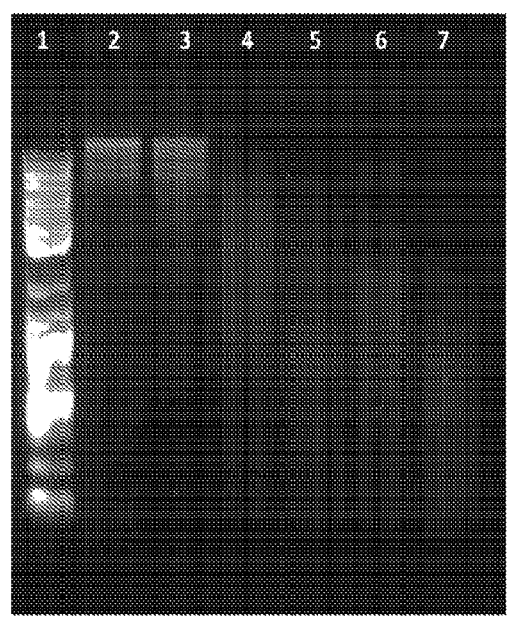

FIG. 2B shows dsDNA extracted from P1 bacteriophage particle when produced in a methyltransferase-positive and methyltransferase-negative strains of E. coli. P1 derivative LB002 was produced in E. coli K-12 strains with or without both dam and dcm methyltransferase genes. Phage DNA was extracted using a phage DNA isolation kit from Norgen Biotek Inc. Phage DNA was subsequently analyzed by restriction enzyme analysis using 120 ng DNA per reaction: lane 1: VWR 2-log DNA ladder; lanes 2, 4, 6: DNA from phage produced in dam+dcm+ E. coli; lanes 3, 5, 7: DNA from phage produced in dcm-dam-E. coli; lanes 2-3: DNA digested with AleI, NheI, and XhoI; lanes 4-5: DNA digested with AleI, NheI, XhoI, and DpnII; and lanes 6-7: DNA digested with AleI, NheI, XhoI, and StyD41. DpnII is blocked by DNA methylated by Dam. StyD41 is blocked by overlapping methylation by Dcm. These data show that DNA from phage produced in bacteria without methylases is less methylated than DNA from phage produced in bacteria with methylases and that DNA from phage produced in bacteria with methylases is not methylated at all possible sites.

B. Multiple Sites Available for Integration of Synthetic DNA Constructs into the Phage Genome.

Figure 3A:
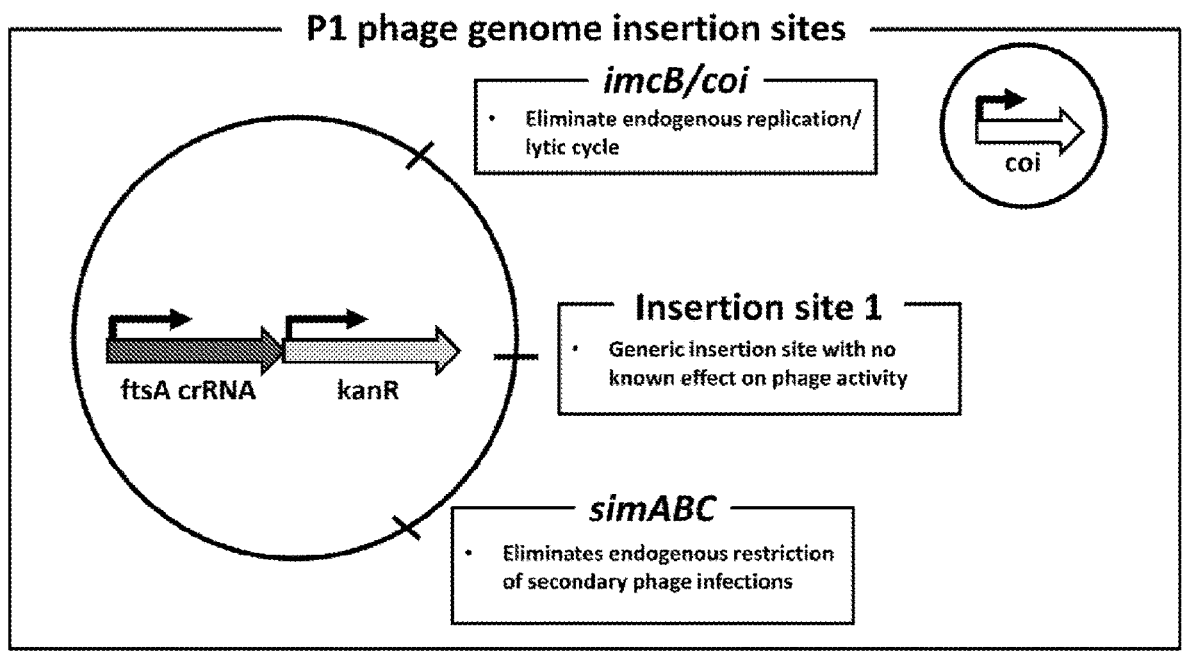
FIGS. 3A-3B show the use of different sites in the phage genome for introducing synthetic sequences.
Figure 3B:
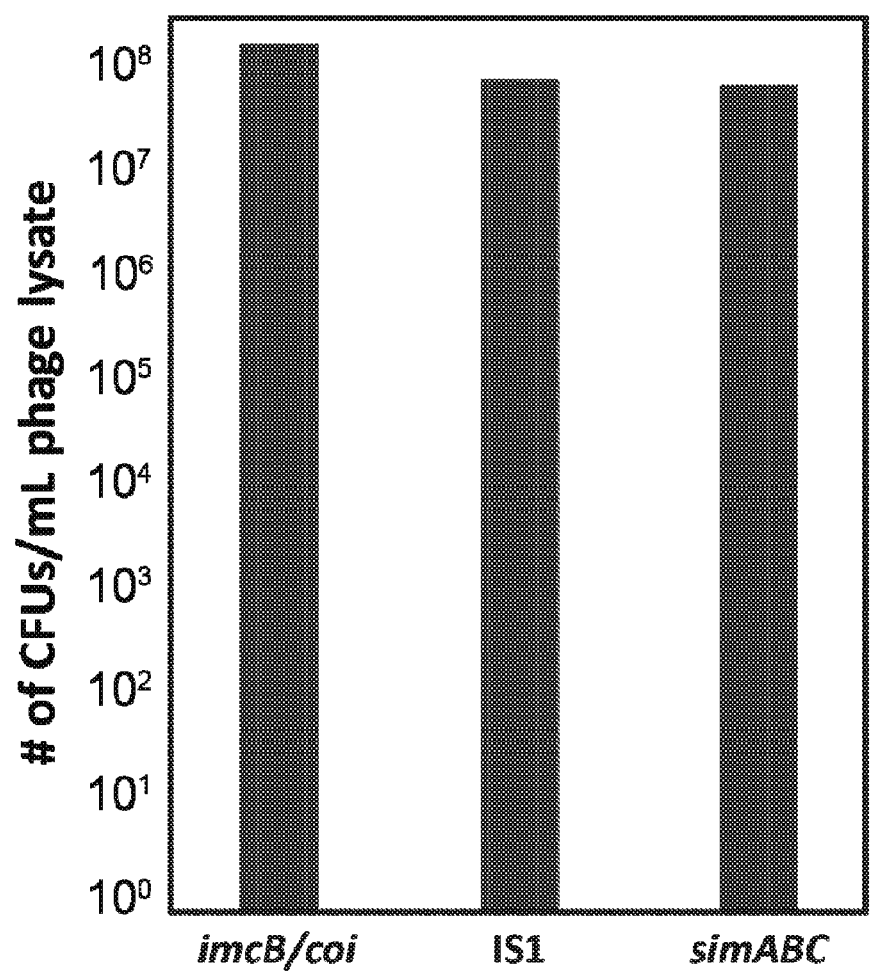

A schematic showing the identified landing sites for foreign DNA in the P1 phage genome is provide in FIG. 3A. IS1, and sim are dispensable genes within the bacteriophage P1 genome and coi-imcB is complementable. The insertion sequence 1 (IS1) element has no known role in P1 function and the simABC operon, is implicated in blocking superinfections. Several P1 bacteriophage variants were constructed in which one of these three sites was disrupted by inserting the DNA sequence for a gene encoding kanamycin resistance that had been inserted into these sites or this same resistance gene flanked by a Type I-E CRISPR RNA targeting the ftsA gene in K co/i. Specifically, P1 particles were generated in E. coli K-12 KL739 harboring pcoi and either P1-ΔimcB/coi:kan$^R$, P1-ΔIS1:kan$^R$, or P1-ΔsimABC:kan$^R$. The cells lysed upon coi induction and the particles were used to infect E. coli K-12 BW25113. Infected cells were plated on LB agar with kanamycin. As shown in FIG. 3B, the resulting particles allowed efficient delivery of the P1 genome to BW25113 cells. Therefore, multiple landing sites (integration sites) are available for synthetic constructs that do not disrupt P1 replication, packaging, and delivery.

C. Effect of Deleting the simABC Operon on Superinfection

Figure 4A:
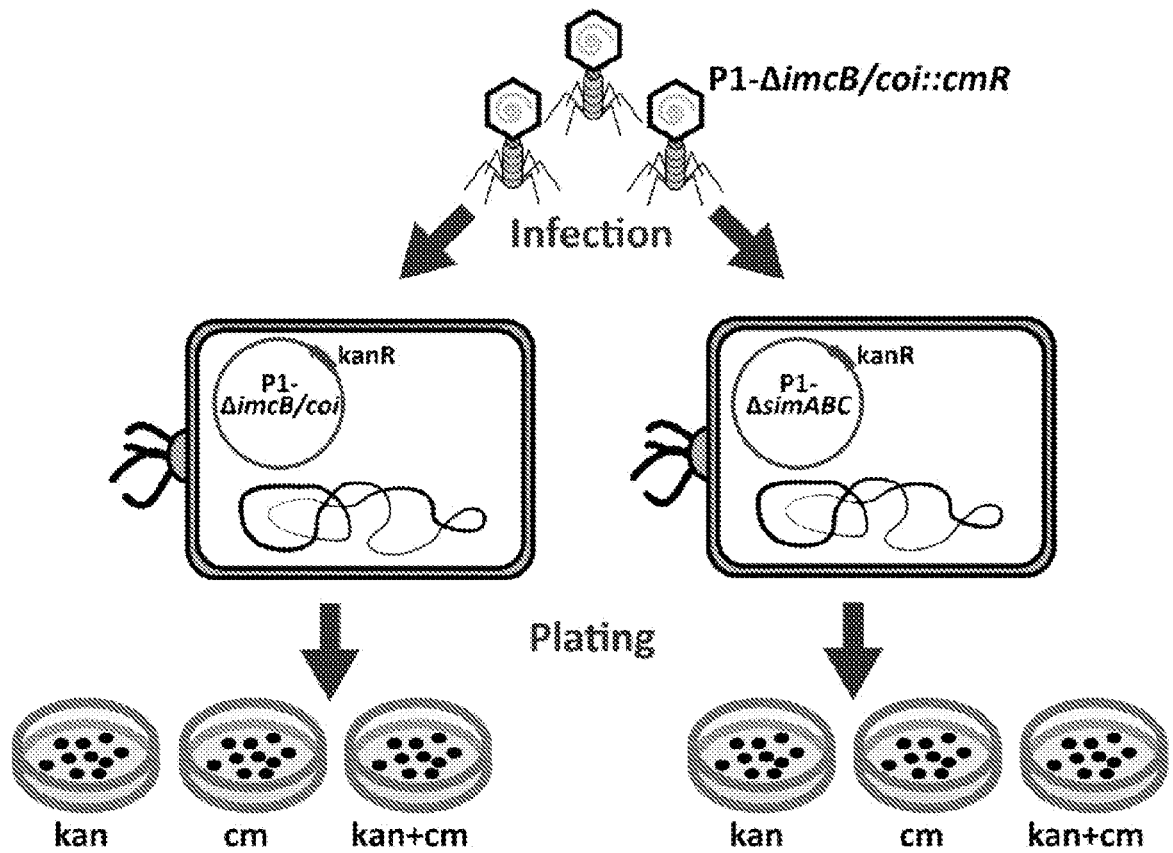
FIG. 4A-4B show that disrupting simAB allows reinfection and maintenance of a second bacteriophage.

The simABC operon has been implicated in preventing superinfection by blocking the transfer of phage DNA from the periplasm into the cytoplasm (Kliem et al. Virology 171, 350-355 (1989)). In the context of CRISPR antimicrobials, superinfection may be important if a cell receives a non-functional phage. To test the impact of simABC in superinfection, we generated MG1655 cells infected with the P1 genome with imcB/coi or simABC replaced with the kanamycin resistance marker (either P1-ΔimcB/coi:kan$^R$ (LB001) or P1-ΔsimABC:kan$^R$ (LB002)). Cells harboring either P1-ΔimcB/coi:kan$^R$ (LB001) or P1-ΔsimABC:kan$^R$ (LB002) were then infected with phage P1-ΔimcB/coi:cm$^R$ and plated on kan, cm, and kan+cm plates (see, FIG. 4A). Cells were then infected at a MOI of 10 with P1 in which the imcB/coi locus was replaced with the chloramphenicol resistance marker. The number of surviving colonies plated on either or both antibiotics was measured.

Figure 4B:
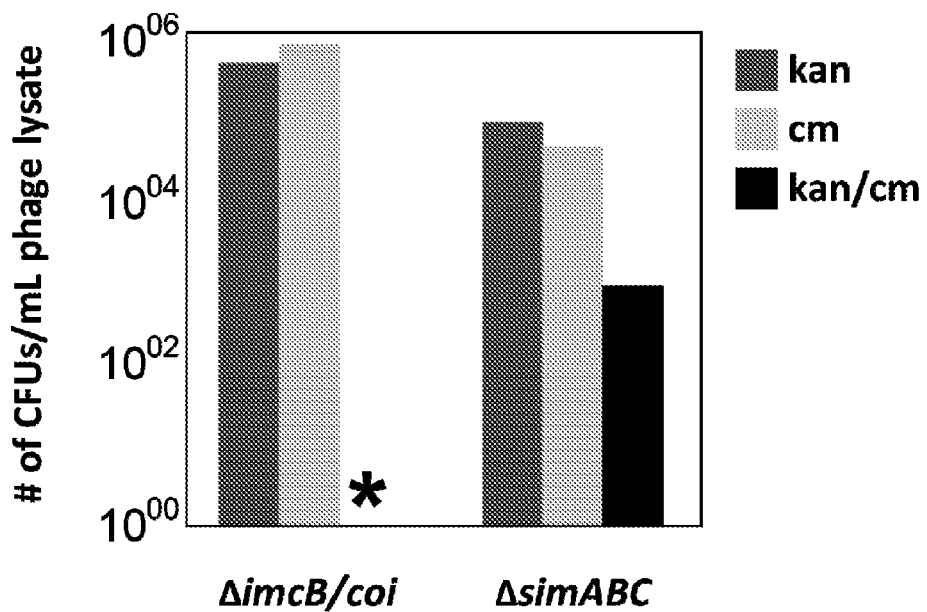

Surprisingly, a similar number of cells that maintained the introduced P1 genome were observed regardless of whether the cells initially harbored P1 lacking imcB/coi or simABC (FIG. 4B). However, when evaluating cells resistant to both antibiotics, only cells initially infected with P1 lacking simABC were recovered. These results suggest that simABC does not block superinfection but instead plays a role in replication or copy number control during the lysogenic cycle. Thus, inserting synthetic DNA into simAB allowed reinfection with a second P1 bacteriophage genome.

D. The P1 Genome is Packaged and Delivered More Efficiently than the P1 Phagemid The most efficient means of packaging and delivering synthetic constructs was explored in P1 bacteriophage particles. Phagemids have become a standard means of encoding synthetic constructs, where the P1 phagemid contains the lytic origin-of-replication, and pacA packaging sites along with inducible expression of the coi gene that drives the P1 lytic cycle (Westwater et al. Microbiology 148, 943-950 (2002); Kittleson et al. ACS synthetic biology 1, 583-589 (2012))). While the P1 phagemid has been used for DNA delivery to diverse gram-negative bacteria and for transferring DNA libraries (Id.), the phagemid must compete with the P1 genome for packaging. As a result, cells may receive either the P1 genome or the phagemid, potentially complicating DNA delivery and programmable killing.

To directly evaluate the delivery of the phagemid and the P1 genome, we replaced the genomic copy of imcB/coi operon in P1 with a kanamycin resistance marker. Specifically, P1 particles were generated in E. coli K-12 KL739 cells harboring P1-ΔimcB/coi:kan$^R$ (kanamycin resistance) and either the P1 phagemid (chloramphenicol resistance) or pcoi (ampicillin resistance). We then combined this genome with the P1 phagemid or a plasmid with inducible expression of coi in an E. coli K-12 substrain KL739 to generate bacteriophage particles. The particles were then used to infect E. coli K-12 MG1655 or E. coli B BL21 followed by plating the infected cells on LB agar with the indicated antibiotics. This experiment was done in triplicate.

Figure 5A:
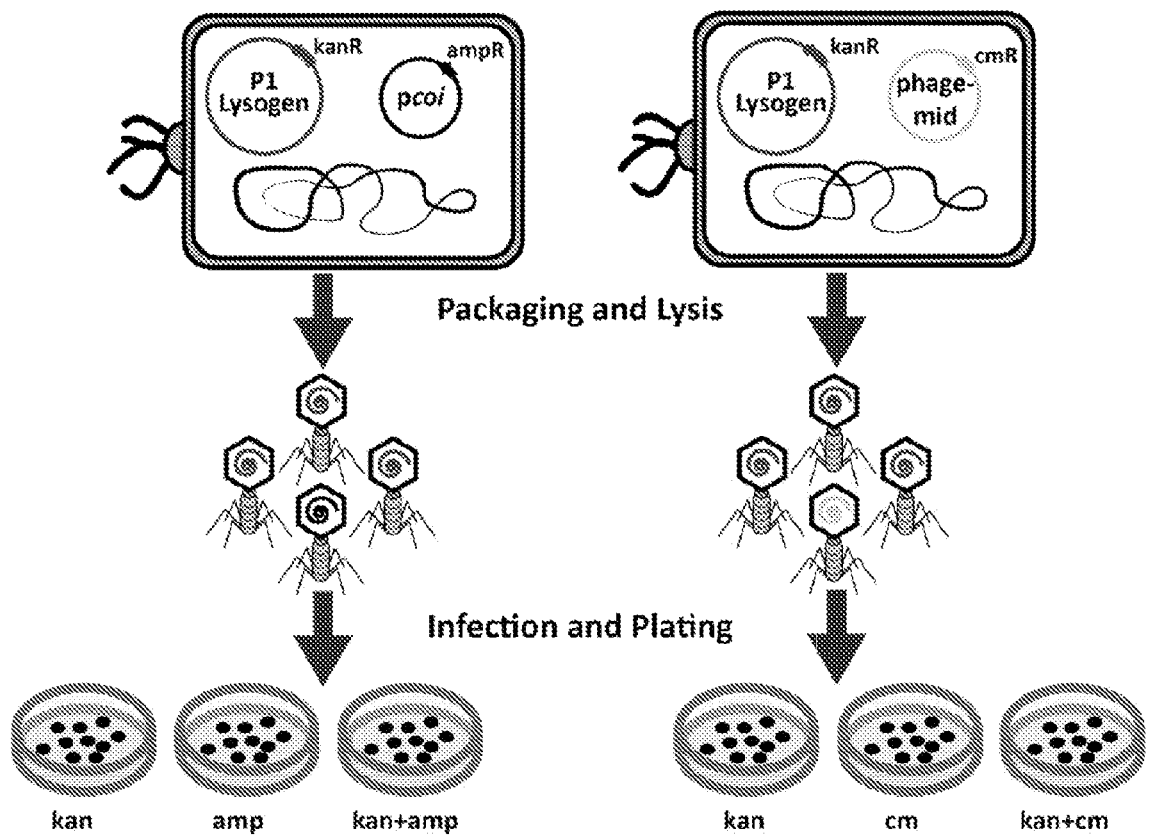
FIG. 5A-5B shows a side by side comparison of P1 particles packaging and delivering of the P1 genome versus packaging and delivery of a P1 phagemid.
Figure 5B:
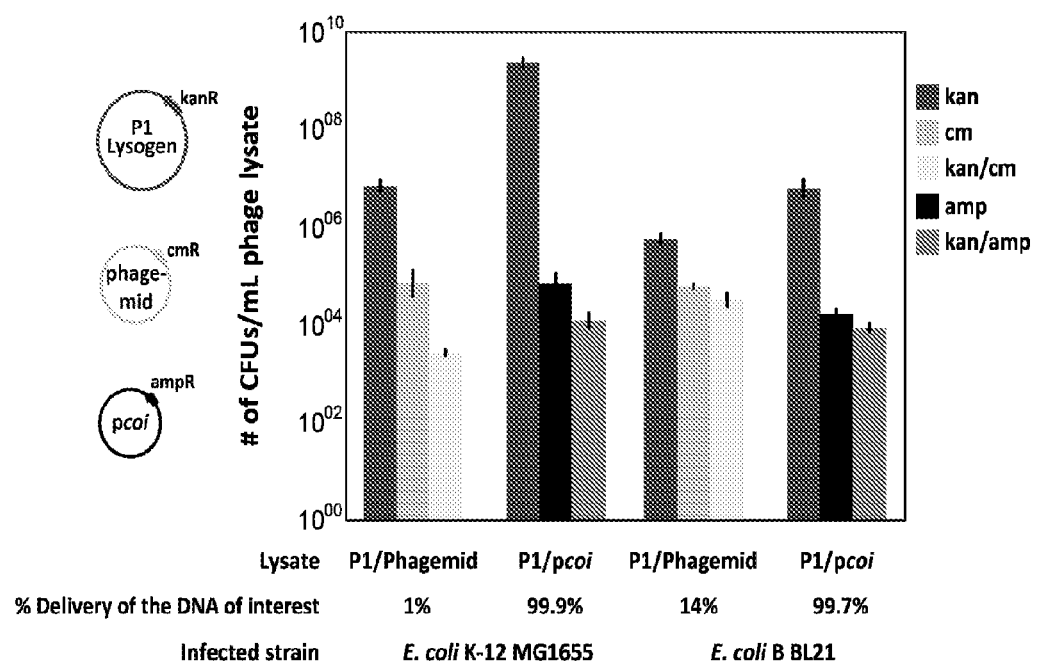

The results are shown in FIG. 5 and demonstrate that the P1 genome is packaged and delivered more efficiently than the P1 phagemid for two different strains of E. coli. FIG. 5 shows that the P1 genome was delivered about 100-fold more frequently than the phagemid, and about 4% of the cells that received the phagemid also received the P1 genome despite the large excess of cells (multiplicity of infection (MOI)=0.003). When the particles were generated using the pcoi plasmid, the P1 genome exhibited about 300-fold greater delivery, suggesting that the phagemid may interfere with the P1 lytic cycle or particle generation. The pcoi plasmid was also delivered at about 33,000-fold less frequently than the P1 genome. Similar trends were observed when infecting E. coli B substrain BL21, although this strain was infected at a lower frequency than MG1655. Thus, for at least for P1 systems, engineering the phage itself yields a lysate that has much higher titers of the engineered product. The P1 genome therefore offers a more efficient delivery vehicle than the P1 phagemid.

E. P1 Delivery Efficiency Varies with Environmental Conditions

Figure 6:
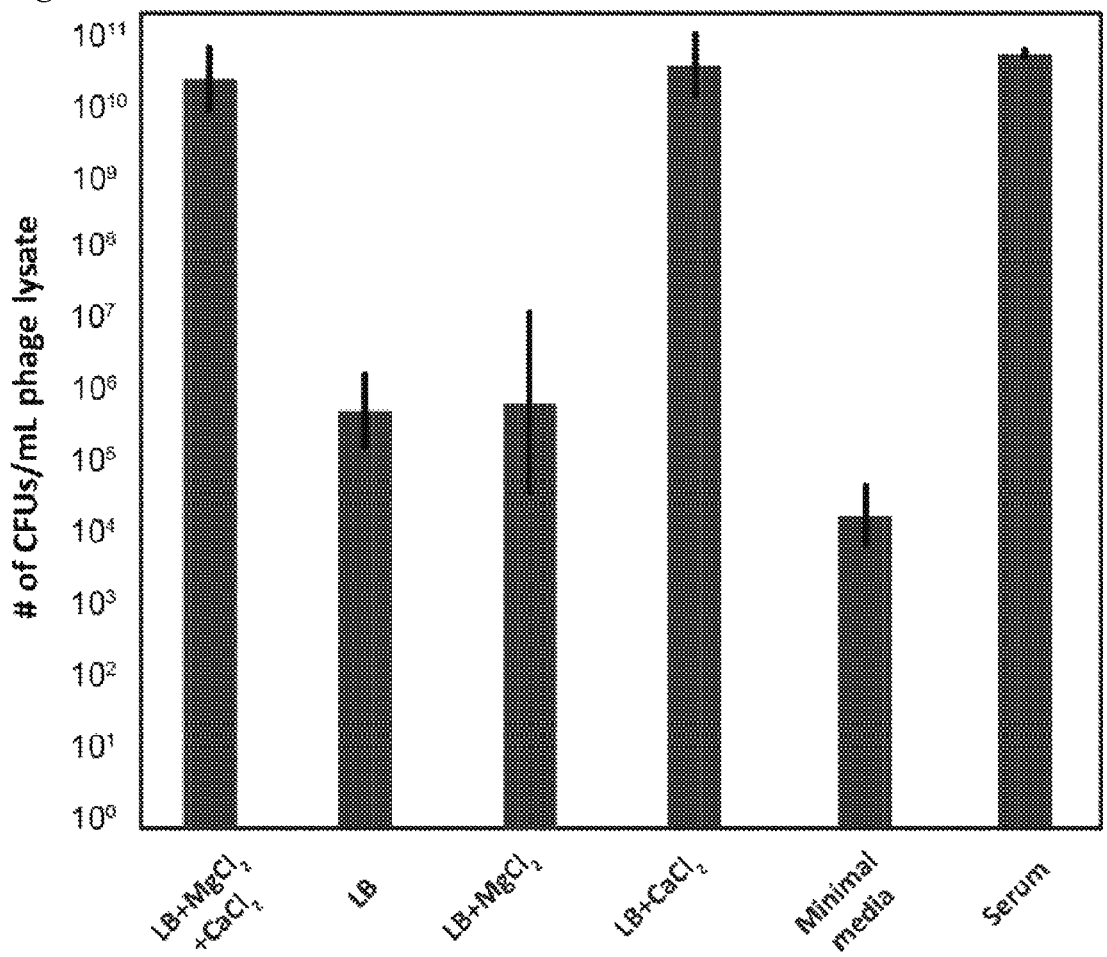
FIG. 6 shows that the P1 genome (P1 coi-icmB:kanR) can be delivered under different environmental conditions. Abbreviations: LB (Luria Broth); Minimal Media (M9 glucose), Serum (Fetal Bovine Serum).

DNA delivery with bacteriophages is generally performed under specific media conditions, such as PLM medium (LB medium containing 100 mM MgCl2 and 5 mM CaCl2) (Kittleson et al. ACS synthetic biology 1, 583-589 (2012)) for P1 transduction and phagemid delivery. However, practical applications will involve varying environments that could impact the delivery efficiency. To interrogate how DNA delivery with P1 is affected by such conditions, E. coli K-12 BW25113 cells grown in LB medium were transferred to different media and delivery of the P1 genome using particles generated with the pcoi plasmid was measured. Infectivity (DNA delivery) remained the same after removing MgCl2, but not CaCl2, from PLM (FIG. 6), which is in line with the importance of CaCl2 for cell adhesion (Watanabe et al. J. Gen. Virol. 17, 19-30 (1972)). However, CaCl2 was not sufficient for DNA delivery, as minimal medium with levels of CaCl2 similar to PLM exhibited greatly reduced delivery. Interestingly, cells in fetal bovine serum and PLM medium ((LB medium containing 100 mM MgCl2 and 5 mM CaCl2) yielded similar delivery efficiencies, suggesting that P1 could efficiently deliver DNA in more in vivo settings.

Overall, these data show that P1 genome can be delivered under different media conditions, where the conditions have a major impact on the delivery efficiency.

F. DNA Methylation and Delivery

Figure 7A:
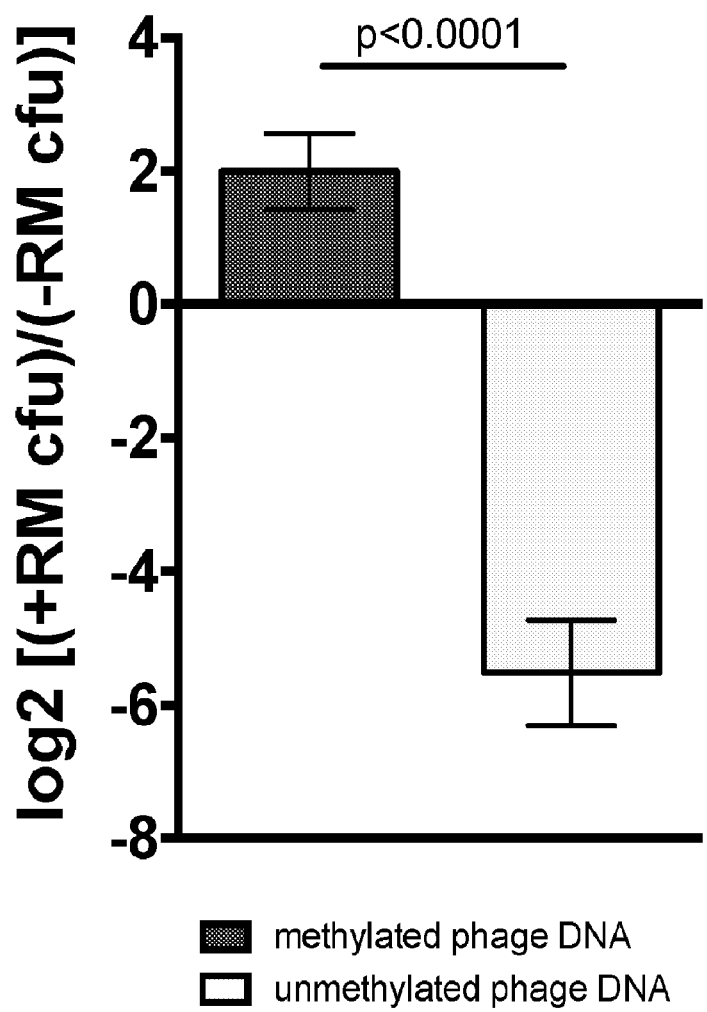
FIG. 7A-7C show DNA delivery via bacteriophage.
Figure 7B:
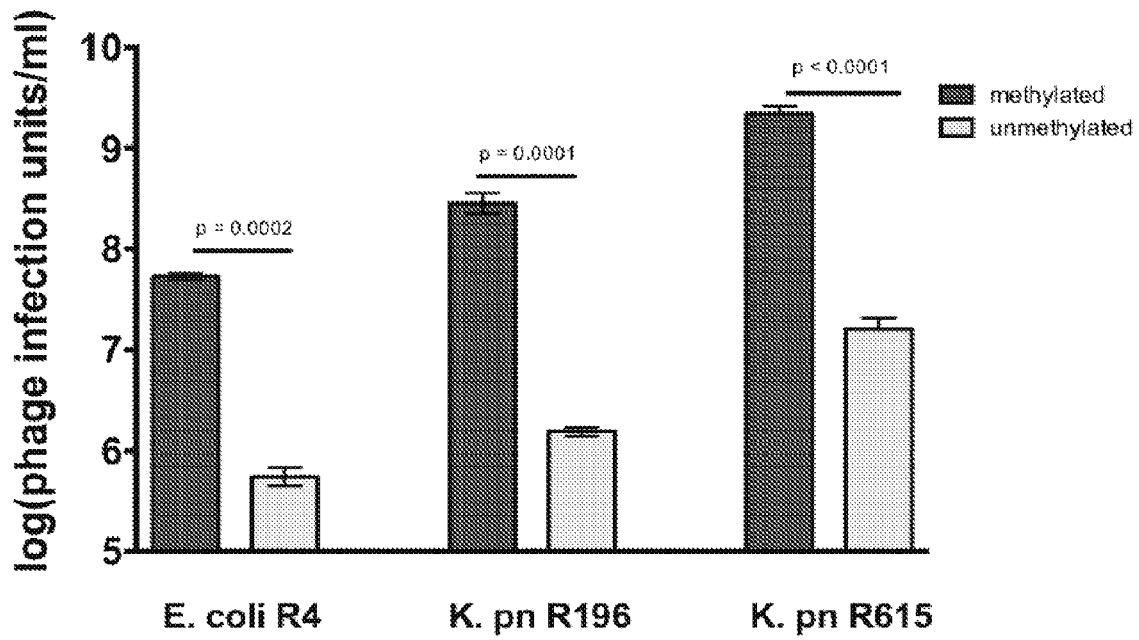
Figure 7C:
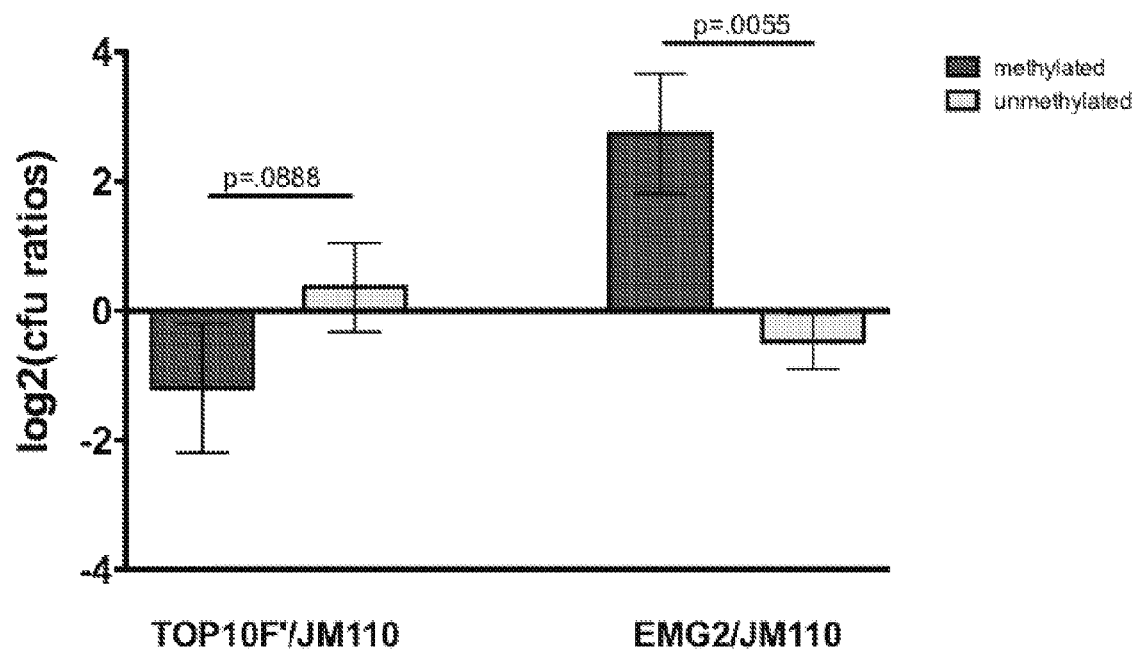

DNA delivery to E. coli using P1 bacteriophage having +/− DNA methylation (i.e., P1 produced in a bacterium that is either DNA methylation (+) or DNA methylation (−)) is shown in FIG. 7A. Bacteriophage P1 carrying a kanamycin resistance cassette was produced in E. coli MG1655 or in MG1655 ΔdamΔdcmΔhdsRMS (lacking methylases and restriction enzymes that target unmethylated DNA). MG1655 was infected by phage P1 produced in MG1655 or in MG1655 ΔdamΔdcmΔhdsRMS. Similarly, MG1655 ΔdamΔdcmΔhdsRMS was infected by phage P1 produced in MG1655 or in MG1655 ΔdamΔdcmΔhdsRMS. The number of infected E. coli cells as measured by CFUs grown under kanamycin selection was then compared between strains and infections. FIG. 7B shows differences in DNA delivery to E. coli and Klebsiella pneumoniae by bacteriophage LB002 +/− methylation. Bacteriophage P1 carrying a kanamycin resistance cassette was produced in E. coli MG1655 or in MG1655 ΔdamΔdcmΔhdsRMS (lacking methylases and restriction enzymes that target unmethylated DNA). E. coli R4 was infected by LB002 produced in MG1655 or in MG1655 ΔdamΔdcmΔhdsRMS. Similarly, K. pneumoniae (K. pn) R196 and K. pn R615 were infected by LB002 produced in MG1655 or in MG1655 ΔdamΔdcmΔhdsRMS. LB002 infectious units, as measured by E. coli or K. pn CFUs grown under kanamycin selection, were then compared between infections. FIG. 7C shows DNA delivery to E. coli using M13KO7 (a variant of M13) bacteriophage that are +/− DNA methylation. M13KO7 was produced in methylase positive (+) E. coli (TOP10F') or in methylation negative (−) E. coli (JM110). TOP10F', EMG2, and JM110 bacterial strains were subsequently infected by M13KO7 produced in methylase (+) E. coli or in methylase (−) E. coli. The number of infected E. coli cells was then compared by strain. TOP10F': encodes dam and dcm but lacks restriction enzymes; EMG2: restriction-methylation systems are intact (will degrade unmethylated double-stranded DNA); JM110: does not encode dam and dcm and lacks restriction enzymes. These data show that phage produced in bacteria with methylases exhibit greater productive infectivity (DNA delivery) than phage produced in bacteria without methylases.

G. DNA Delivery and CRISPR-Mediated Killing in E. coli

The Type I-E CRISPR-Cas system native to E. coli was utilized to address the question of whether the P1 genome could accommodate one or more components of a CRISPR-Cas system and subsequently elicit CRISPR-mediated killing. For this purpose, freezer stocks of E. coli K-12 BW25113 and E. coli K-12 BW25113Δcas3 harboring pcas3 plasmid were streaked to isolation on LB agar and E. coli expressing CASCADE and Cas3 (components of the Type I-E CRISPR-Cas system, "+cas") or not ("−cas") were cultured.

Specifically, individual colonies were inoculated into 3 ml of LB media and shaken overnight at 37° C. and 250 rpm. The cultures then were pelleted and resuspended in 1 mL of PLM (LB medium containing 100 mM MgCl2 and 5 mM CaCl2) and the ABS600 was measured on a Nanodrop 2000c spectrophotometer (Thermo Scientific). The cultures were then diluted in PLM to ABS600 of 0.001 and each strain was infected at the indicated multiplicity of infection (MOI) with bacteriophage P1 engineered to express a crRNA targeting ftsA (CRISPR phage); the appropriate amount of bacteriophage lysate was added to achieve different MOI's including 0. The culture/phage mixture was mixed by pipetting and shaken at 37° C. and 250 rpm. Bacterial growth was then compared between conditions as measured by absorbance at a 600 nm (OD600) with measurements taken every 30 minutes for up to 7 hours. The number of surviving bacterial cells at different MOIs for each bacterial strain was then compared.

FIG. 8A shows that E. coli expressing Cascade and Cas3 (components of the Type I-E CRISPR-Cas system, "+cas") or not ("−cas")) show that the Type I-E Cascade and Cas3 negatively affects growth following delivery of P1 equipped with a genome-targeting CRISPR RNA. As expected, CRISPR-phage shows clear retardation of growth in both cell types, with improved growth suppression in the "+cas" group. This demonstrates the improved antimicrobial effect of the CRISPR-Cas system versus phage alone.

CRISPR-phage is observed to kill cells in both cell types at MOI>1, with increased killing in the "+cas" group as expected. As shown in FIG. 8B, Type I-E Cascade and Cas3 negatively affects survival following delivery of P1 equipped with a genome-targeting CRISPR RNA. E. coli expressing CASCADE and Cas3 (components of the Type I-E CRISPR-Cas system, "+cas") or not ("−cas") was infected at the indicated MOI with bacteriophage P1 engineered to express a crRNA targeting ftsA (a CRISPR phage). These data clearly demonstrate that CRISPR significantly enhances killing compared to phage alone.

Further, delivering the P1 genome encoding a genome-targeting CRISPR RNA in different locations kills E. coli in the presence of the Type I-E Cascade and Cas3. Unlike the Type II/Cas9 CRIPSR-Cas system, the Type I-E CRISPR-Cas system can elicit potent cell death at all potential sites (Gomaa, A. A. et al. MBio 5, e00928-913 (2014); Cui et al. Nucleic Acids Res. (2016). doi:10.1093/nar/gkw223). A spacer that targets the essential ftsA gene in *E. coli* (Gomaa, A. A. et al. *MBio* 5, e00928-913 (2014)) was inserted into the coi/imcB, IS1, or simABC landing sites of the P1 genome. The resultant P1 bacteriophages containing an insertion of a crRNA targeting ftsA into the P1 coi-imcB gene, IS1 gene, or sim gene were then used to infect *E. coli* BW25113 cells with or without expression of all of the Type I-E Cas proteins (Cas3, Cse1, Cse2, Cas5e, Cas6e, Cas7). The cells were then mixed with the bacteriophages at different MOI's and the changes in bacterial cell density (turbidity of the culture) was measured after seven hours of growth. We found that all cultures with cells lacking the Cas proteins exhibited substantial increases in cell density, though the final turbidity was lower at greater MOI's (FIG. 8C). In contrast, cultures of cells expressing all of the Type I-E Cas proteins (Cas3, Cse1, Cse2, Cas5e, Cas6e, Cas7)) exhibited little to no detectable growth (*), thereby showing that that CRISPR/phage treatment eliminates growth (FIG. 8C). These results indicate that the P1 genome that is equipped with components of a CRISPR-Cas system can be used to elicit CRISPR-mediated killing.

Further evidence that CRISPR/phage treatment during culture results in reduced viability is provided in FIG. 8D. *E. coli* expressing Type I-E CRISPR Cas3 was infected either with (1) bacteriophage P1 containing a genomic insertion of crRNA targeting ftsA in place of the coi gene or (2) with no bacteriophage, and the number of surviving bacterial cells was compared. *E. coli* exposed to phage exhibited a 4-log (~10000×) loss in viability. Thus, in absence of the CRISPR equipped phage, both cells with and without Cas proteins show substantial growth after 7 hours. However, when the phage was included in the initial culture, no detectable growth was observed for the cells expressing a complete set of Cas proteins.

H. Efficient DNA Delivery to *Shigella flexneri*

To investigate if the P1 genome may be used to infect other genera outside of *Escherichia*, two strains of *Shigella flexneri* were tested. This species is associated with the worldwide diarrheal disease Shigellosis. *Shigella* causes about 500,000 cases of diarrhea in the United States annually, including 27,000 drug-resistant infections. Delivery of the P1 genome having the imcB/coi operon replaced with the kanamycin resistance marker was measured. The resulting P1 particles were determined to be efficiently delivered the genome to both strains of *S. flexneri*, with a number colony forming units between those observed for *E. coli* MG1655 and *E. coli* BL21 (FIG. 9). These results confirm that the P1 genome can be delivered and stably maintained in multiple genera, opening the potential of utilizing P1 as a multi-species delivery vehicle for CRISPR antimicrobials.

I. Targeting Antibiotic Resistance Bacteria

We compared the combination of P1 CRISPR phage (targeting ftsA) and ciprofloxacin to the use of P1 CRISPR phage alone for killing *E. coli* R182, a ciprofloxacin-resistant strain (FIG. 10A). Ciprofloxacin (Cip) dose was the highest therapeutically relevant concentration (4 micrograms per milliliter) to which the R182 strain is known to be resistant. *E. coli* were infected with CRISPR phage targeting the *E. coli* ftsA gene at a range of multiplicities of infection (MOI). As expected, ciprofloxacin alone did not reduce bacterial viability (FIG. 10A). In contrast, increasing CRISPR phage MOI resulted in antibiotic-independent increases in the reduction of viable bacterial cells (FIG. 10A).

In addition, the combination of P I CRISPR phage (targeting ftsA) and imipenem, a standard of care antibiotic in *E. coli* infections, was compared with P1 CRISPR phage alone for killing *E. coli* R182, a ciprofloxacin-resistant strain (FIG. 10B). Imipenem was held at a constant dose (the LD50 for *E. coli* R182) and resulted in a baseline 0.3-log CFU reduction. The *E. coli* cells were infected with CRISPR phage at a range of MOI. At an MOI of 2, a significant effect of the combination treatment (P<0.05) vs. phage or antibiotic alone was observed. At higher MOIs, the CRISPR phage exerted a dominant killing effect, suggesting that a phage+antibiotic combination may have an additive effect.

Finally, we compared the loss of viable *E. coli* R182 cells following exposure to imipinem, P1 CRISPR phage targeting ftsA, or a combination of both (FIG. 10C). For relevant conditions (n=3 for each condition), imipenem was held at a constant dose (LD50 for *E. coli* R182) and CRISPR phage was held to a MOI of 2. Bacterial killing was observed at 120 minutes following CRISPR phage infection with or without imipinem.

J. Targeting *E. coli* Infection in a Mouse

CRISPR phage targeting *E. coli* decreases viable bacterial counts in a mouse model of thigh muscle infection (FIG. 11A). Mice were administered an intramuscular thigh injection of $1.6 \times 10^6$ CFU of *E. coli* followed by phage treatment of an intramuscular thigh injection of $1.9 \times 10^{11}$ pfu of CRISPR phage targeting ftsA or 50 uL TBS (a no treatment control). Viable bacterial counts from thigh tissues were measured 30, 60, 120, 180, and 240 minutes following phage treatment. Phage treatment was observed to consistently result in about 0.3-log reductions and the reduction in bacterial counts was statistically significant at two time points (P<0.05) and (P<0.001).

FIG. 11B shows that CRISPR phage targeting *E. coli* increases animal survival time in a mouse model. Mice were infected by IP (intraperitoneal) injection with *E. coli* strain R260 at a dose of $1.5 \times 10^7$ CFU in 5% hog mucin and then were left untreated or were treated by IP injection with a single dose of CRISPR phage targeting *E. coli* gene ftsA (dose=1.9×10/\11 pfu, MOI of about 100). It was determined that a single-dose phage treatment significantly extended mouse survival (Wilcoxon test, P<0.05).

K. Ability of the Phage Delivered CRISPR RNAs to Kill Various Strains of *E. coli* or *K. pneumonia*

Type I CRISPR phage particles expressing a crRNA targeting ftsA were used to infect a library of strains consisting of *E. coli*. Reported in Table 3 and in summary Table 5 are the reductions in bacterial population compared to untreated growth controls for each strain following CRISPR phage infection. These data demonstrate that a phage can deliver CRISPR constructs across *E. coli* strains.

TABLE 3

Sensitivity to P1 defined as KanR colonies detected over background.

| Species | Strain | Reduction in CFU* | Sensitive to Kan | Sensitive to P1* | Decrease is p < 0.05 | Ratio Kan-Cm:Cm | Collection Name | Collection ID No. | Type | Antibiotic resistance |
|---|---|---|---|---|---|---|---|---|---|---|
| *E. coli* | 4 | 98.87% | TRUE | TRUE | TRUE | 85.20% | ATCC | 25922 | QC - NCCLS, thigh infection model | none reported |

TABLE 3-continued

Sensitivity to P1 defined as KanR colonies detected over background.

| Species | Strain | Reduction in CFU* | Sensitive to Kan | Sensitive to P1* | Decrease is p < 0.05 | Ratio Kan-Cm:Cm | Collection Name | Collection ID No. | Type | Antibiotic resistance |
|---|---|---|---|---|---|---|---|---|---|---|
| E. coli | 253 | 59.87% | TRUE | FALSE | TRUE | 0.00% | #N/A | #N/A | #N/A | #N/A |
| E. coli | 260 | 99.98% | TRUE | TRUE | TRUE | 70.00% | ATCC | 8739 | Microbial limits std | none reported |
| E. coli | 533 | 99.97% | TRUE | TRUE | TRUE | 46.15% | ATCC | 11229 | | none reported |
| E. coli | 571 | 93.60% | TRUE | TRUE | TRUE | 0.11% | ATCC | 700928 | CFT073 WAM 2267 | none reported |
| E. coli | 609 | 50.43% | TRUE | TRUE | TRUE | 38.26% | ATCC | 31619 | | none reported |
| E. coli | 610 | −8.64% | TRUE | TRUE | FALSE | 0.42% | ATCC | 43890 | | none reported |
| E. coli | 624 | −9.81% | TRUE | TRUE | FALSE | 0.00% | ATCC | BAA-1653 | strain EH1534 | none reported |
| E. coli | 630 | 5.37% | TRUE | FALSE | FALSE | 0.00% | ATCC | 43888 | | none reported |
| E. coli | 173 | −12.77% | TRUE | FALSE | FALSE | 0.00% | External | H1 | Clinical isolate | |
| E. coli | 174 | 99.85% | TRUE | FALSE | TRUE | 0.00% | External | H2 | Clinical isolate | |
| E. coli | 176 | 99.95% | TRUE | FALSE | TRUE | 0.00% | External | H4 | Clinical isolate | |
| E. coli | 177 | −3.65% | TRUE | FALSE | FALSE | 0.00% | External | H5 | Clinical isolate | |
| E. coli | 178 | 99.67% | TRUE | TRUE | TRUE | 0.71% | External | H6 | Clinical isolate | |
| E. coli | 180 | 90.21% | TRUE | TRUE | TRUE | 2.70% | External | H8 | Clinical isolate | |
| E. coli | 181 | 98.09% | TRUE | TRUE | TRUE | 80.65% | External | H9 | Clinical isolate | |
| E. coli | 182 | 99.99% | TRUE | FALSE | TRUE | 0.00% | External | H10 | Clinical isolate | |
| E. coli | 184 | 89.23% | FALSE | FALSE | TRUE | 82.86% | External | I2 | Clinical isolate | ciprofloxacin resistant |
| E. coli | 185 | 96.10% | TRUE | FALSE | TRUE | 0.00% | External | I3 | Clinical isolate | ciprofloxacin resistant |
| E. coli | 186 | 21.37% | FALSE | FALSE | FALSE | 44.02% | External | I4 | Clinical isolate | ciprofloxacin resistant |
| E. coil | 187 | 32.79% | FALSE | FALSE | FALSE | 117.89% | External | I5 | Clinical isolate | ciprofloxacin resistant |
| E. coli | 657 | 90.27% | TRUE | TRUE | TRUE | 443.66% | Locus Biosciences | K-12 + casABCDE | Transfected CRISPR/Cas | |
| E. coli | 658 | 95.57% | TRUE | FALSE | TRUE | 0.00% | Locus Biosciences | K-12 | Parent strain | |

*Reduction in CFUs is relative to the number of CFUs that grew in untreated (no phage) controls.

In addition, Type I CRISPR phage expressing a crRNA targeting ftsA were used to infect a library of strains consisting of *Klebsiella pneumoniae*. Reported in Table 4 and in summary Table 5 are the reductions in bacterial population compared to untreated growth controls for each strain following CRISPR phage infection. These data demonstrate that a phage can deliver CRISPR constructs across *Klebsiella* strains.

TABLE 4

Sensitivity to P1 defined as KanR *Klebsiella* (*Kleb*) colonies detected over background.

| Species | Strain | Reduction in CFU | Sensitive to Kan | Sensitive to P1* | Decrease is p < 0.05 | Ratio Kan-Cm:Cm | Collection | Collection ID No. | Type | Antibiotic resistance |
|---|---|---|---|---|---|---|---|---|---|---|
| Kleb | 9 | −0.88% | FALSE | FALSE | FALSE | 100.44% | ATCC | 700603 | QC - NCCLS | yes |
| Kleb | 39 | −11.84% | TRUE | FALSE | FALSE | 0.00% | ATCC | 13882 | Model for capsule bacterium | none reported |
| Kleb | 494 | −7.57% | TRUE | FALSE | FALSE | 0.00% | ATCC | 43816 | thigh infection model | none reported |
| Kleb | 519 | 10.25% | FALSE | FALSE | FALSE | 0.02% | ATCC | 51503 | subsp. pneumoniae RP1 | yes |
| Kleb | 524 | 9.89% | TRUE | FALSE | FALSE | 0.00% | ATCC | 13883 | | none reported |
| Kleb | 548 | 2.64% | FALSE | FALSE | FALSE | 0.05% | ATCC | 51504 | | none reported |
| Kleb | 615 | 41.43% | TRUE | TRUE | TRUE | 66.94% | ATCC | 10031 | | none reported |
| Kleb | 344 | 43.22% | FALSE | FALSE | TRUE | 85.07% | MET | H59476 | Clinical isolate | unknown |
| Kleb | 345 | 1.32% | FALSE | FALSE | FALSE | 102.00% | MET | S9604 | Clinical isolate | unknown |
| Kleb | 346 | 9.43% | FALSE | FALSE | FALSE | 102.08% | MET | F6199 | Clinical isolate | unknown |
| Kleb | 347 | 15.24% | FALSE | FALSE | FALSE | 101.74% | MET | S9391 | Clinical isolate | unknown |
| Kleb | 188 | 31.66% | TRUE | TRUE | FALSE | 0.04% | External | J1 | Clinical isolate | unknown |
| Kleb | 189 | −1.01% | TRUE | TRUE | FALSE | 0.08% | External | J3 | Clinical isolate | unknown |
| Kleb | 190 | 7.13% | TRUE | FALSE | FALSE | 0.00% | External | J4 | Clinical isolate | unknown |
| Kleb | 191 | 12.62% | TRUE | FALSE | FALSE | 0.00% | External | J5 | Clinical isolate | unknown |
| Kleb | 192 | −2.81% | TRUE | FALSE | FALSE | 0.00% | External | J7 | Clinical isolate | unknown |
| Kleb | 193 | 13.19% | TRUE | FALSE | FALSE | 0.00% | External | J9 | Clinical isolate | unknown |

TABLE 4-continued

Sensitivity to P1 defined as KanR Klebsiella (Kleb) colonies detected over background.

| Species | Strain | Reduction in CFU | Sensitive to Kan | Sensitive to P1* | Decrease is p < 0.05 | Ratio Kan-Cm:Cm | Collection | Collection ID No. | Type | Antibiotic resistance |
|---|---|---|---|---|---|---|---|---|---|---|
| Kleb | 194 | 84.79% | TRUE | TRUE | TRUE | 0.02% | External | J18 | Clinical isolate | unknown |
| Kleb | 195 | 4.53% | TRUE | TRUE | FALSE | 0.47% | External | J20 | Clinical isolate | unknown |
| Kleb | 196 | 81.37% | TRUE | TRUE | TRUE | 10.60% | External | J27 | Clinical isolate | unknown |
| Kleb | 197 | 8.63% | TRUE | FALSE | FALSE | 0.00% | External | J30 | Clinical isolate | unknown |
| Kleb | 198 | 38.52% | TRUE | TRUE | TRUE | 1.67% | External | J33 | Clinical isolate | unknown |
| Kleb | 199 | -5.68% | TRUE | FALSE | FALSE | 0.00% | External | J34 | Clinical isolate | unknown |
| Kleb | 200 | 20.09% | TRUE | FALSE | FALSE | 0.00% | External | J37 | Clinical isolate | unknown |
| Kleb | 201 | 10.70% | TRUE | FALSE | FALSE | 0.00% | External | J38 | Clinical isolate | unknown |
| Kleb | 202 | 17.62% | TRUE | TRUE | FALSE | 0.84% | External | J47 | Clinical isolate | unknown |

TABLE 5

Summary of clinical isolates of E. coli and K. pneumoniae (Kleb) killed by CRISPR phage targeting ftsA taken from Tables 3 and 4.

| Species | Reduction in CFU | Collection | Collection ID | Type | Antibiotic resistance |
|---|---|---|---|---|---|
| E. coli | 98.87% | ATCC | 25922 | Catalog strain | Unknown |
| E. coli | 59.87% | TBD | TBD | Catalog strain | Unknown |
| E. coli | 99.98% | ATCC | 8739 | Catalog strain | Unknown |
| E. coli | 99.97% | ATCC | 11229 | Catalog strain | Unknown |
| E. coli | 93.60% | ATCC | 700928 | Catalog strain | Unknown |
| E. coli | 50.43% | ATCC | 31619 | Catalog strain | Unknown |
| E. coli | 99.85% | External | H2 | Clinical isolate | Kanamycin |
| E. coli | 99.95% | External | H4 | Clinical isolate | Unknown |
| E. coli | 99.67% | External | H6 | Clinical isolate | Unknown |
| E. coli | 90.21% | External | H8 | Clinical isolate | Unknown |
| E. coli | 98.09% | External | H9 | Clinical isolate | Unknown |
| E. coli | 99.99% | External | H10 | Clinical isolate | Unknown |
| E. coli | 89.23% | External | I2 | Clinical isolate | Ciprofloxacin, kanamycin |
| E. coli | 96.10% | External | I3 | Clinical isolate | Ciprofloxacin, kanamycin |
| Kleb | 41.43% | ATCC | 10031 | Catalog strain | Unknown |
| Kleb | 43.22% | External | H59476 | Clinical isolate | Kanamycin |
| Kleb | 84.79% | External | J18 | Clinical isolate | Unknown |
| Kleb | 81.37% | External | J27 | Clinical isolate | Unknown |
| Kleb | 38.52% | External | J33 | Clinical isolate | Unknown |

L. Extended Spacer Length Elicits Killing

The Type I-E system with CRISPR RNA spacers that are not the wild-type length can elicit cell killing. CRISPR RNAs with a 32-nt spacer (wild type length) (+0) or a 44-nt spacer (+12) were designed to target four locations around the lacZ gene in the E. coli MG1655 genome (p1, as1, p2 and s1) (FIG. 12). The extension was made to the 3' end of 44-nt spacer to be substantially the same as the target sequence. Plasmids expressing each CRISPR RNA as a repeat-spacer-repeat were transformed into E. coli MG1655 expressing the Type I-E Cas3 and Cascade proteins. A drop in the transformation efficiency reflects genome attack and cell death, where only a few cells are able to escape killing through mutations to the target sequence, the spacer, or the Cas proteins. As shown in the data, all designed CRISPR RNAs led to a $10^3$ to $10^5$ reduction in the transformation efficiency as compared to a spacer free control, demonstrating that CRISPR RNAs with longer spacers can elicit targeted killing. It was surprising that the larger complex was still able to recruit and activate Cas3. Crystal structures suggested large conformational changes that occur over the entire complex were required to activate Cas3 (Mulepati et al. *Science* 345(6203):1479-84 (2014); Jackson et al. *Science* 345(6203):1473-9 (2014); Rutkauskas et al. *Cell Rep* pii: S2211-1247(15)00135-7 (2015); Gong et al. *Proc Natl Acad Sci USA.* 111(46):16359-64 (2014)) and it was expected that adding additional protein subunits would disrupt these conformational changes. The data suggest that this does not happen and show that extended spacers elicit similar level of killing as regular-length spacers based on the similar reductions in the transformation efficiency.

M. Bacteriophage Particles Encoding the Type I-E CRISPR-Cas System from *E. coli* or the Type I-C CRISPR-Cas System *Bacillus halodurans*

The entire Type I-E CRISPR-Cas system from *E. coli* or the Type I-C CRISPR-Cas system from *Bacillus halodurans* is encoded into the P1 bacteriophage genome and used to demonstrate targeted killing of *E. coli*. In each case, one or more polynucleotides encoding a Type I-C CRISPR-Cas system or Type I-E CRISPR-Cas system (e.g., Type I-E Cascade or Type I-C Cascade polypeptides and Cas3 polypeptides) as well as a CRISPR array are introduced to the P1 genome at a selected site in the phage genome (e.g., a dispensable site of integration or at a complemented site of integration). The one or more polynucleotides encoding a Type I-C CRISPR-Cas system or Type I-E CRISPR-Cas system are synthesized or amplified from the source strain using PCR and cloned into a donor plasmid vector (ex: pKD3, pKD13, or others). The donor vector is designed with a specific antibiotic resistance and homology regions that match the selected landing site in the P1. Using homologous recombination, one or more polynucleotides encoding a Type I-C CRISPR-Cas system or Type I-E CRISPR-Cas system are cloned into the P1 lysogen present in the production strain. Positive clones are selected by antibiotic resistance. If the antibiotic resistance marker is flanked by recombinase sites (e.g. FRT sites), then the resistance marker can be excised by expressing the recombinase as is known in the art.

Following the same approach, a CRISPR array encoding genome-targeting crRNAs is encoded into the P1 genome at a different landing site integration site than that for the cas genes. The CRISPR array is designed to target a specific sequence present in a target strain but not the production strain.

The phage particles are then produced and administered to the target bacterial strain and the number of viable colonies counted. In some aspects, the phage particles are produced using a production host bacterial strain that has a methylation pattern that is substantially similar to that of the target host bacterium. The designed phages should greatly reduce the number of viable colonies in comparison to no phage or a non-targeting phage.

Discussion

The broad-host P1 bacteriophage was demonstrated to efficiently deliver DNA to multiple bacterial species and therefore, may be used as a platform for delivery of CRISPR antimicrobials. One advantage of a broad-host bacteriophage is that a single platform can be generated from a single, industrial production strain and applied against a range of bacteria. For instance, P1 particles could be created in an industrial strain of commensal *E. coli* and then used to combat infections by enteric pathogens such as enterohemorrhagic *E. coli*, *Shigella*, or *Klebsiella*. The ability to separate production strains from infectious strains addresses the biomanufacturing challenge of culturing large batches of a bacterial pathogen in order to generate bacteriophage particles against the same pathogen. It also creates the possibility of readily modifying the antimicrobial to target different species by merely changing the CRISPR array.

The foregoing is illustrative of the present invention, and is not to be construed as limiting thereof. The invention is defined by the following claims, with equivalents of the claims to be included therein.

That which is claimed is:

1. A method of killing a target bacterium, comprising contacting the target bacterium with a bacteriophage comprising:
   (a) a Type I CRISPR array comprising:
      (i) a spacer sequence substantially complementary to a target DNA sequence of the target bacterium, wherein the target DNA sequence is adjacent to a protospacer adjacent motif (PAM), and
      (ii) at least two repeat sequences; and
   (b) an exogenous nucleic acid construct encoding an exogenous Cas3 polypeptide that recognizes a complex of Cascade and the Type I CRISPR array, and an exogenous nucleic acid construct encoding a Cascade polypeptide that recognizes the Type I CRISPR array,
   wherein the Type I CRISPR array, the exogenous nucleic acid construct encoding an exogenous Cas3 polypeptide, and/or the exogenous nucleic acid construct encoding a Cascade polypeptide is integrated into the bacteriophage DNA at a dispensable site or a complemented site, and
   wherein the target DNA sequence of the target bacterium is cleaved and degraded by the Cas3 polypeptide, thereby killing the target bacterium.

2. The method of claim 1, wherein the target DNA sequence is in an essential gene or a non-essential gene.

3. The method of claim 1, wherein the spacer sequence is linked to the at least two repeat sequences at both a 5' and a 3' end.

4. The method of claim 1, wherein the spacer sequence is at least 70% complementary to the target DNA sequence.

5. The method of claim 1, wherein the target bacterium is *E. coli*.

6. The method of claim 1, wherein the target bacterium is *Klebsiella pneumoniae*.

7. The method of claim 1, wherein the target bacterium is antibiotic-resistant.

8. The method of claim 1, wherein the spacer sequence comprises a length of about 15 nucleotides to about 150 nucleotides.

9. The method of claim 1, wherein the bacteriophage is from a lytic bacteriophage.

10. The method of claim 9, wherein the lytic bacteriophage is a broad-host bacteriophage.

11. The method of claim 1, wherein the dispensable site is (a) a phage-encoded restriction-modification system, (b) a gene that blocks superinfection, (c) an inhibitor of restriction-modification system, (d) an insertion sequence element, (e) an addiction system, or (f) any combination thereof.

12. The method of claim 1, wherein the complemented site is (a) an activator of the lytic cycle, (b) a lytic gene, (c) a tRNA, (d) a particle component, or (e) any combination thereof.

* * * * *

UNITED STATES PATENT AND TRADEMARK OFFICE
CERTIFICATE OF CORRECTION

PATENT NO. : 11,155,823 B2
APPLICATION NO. : 15/735028
DATED : October 26, 2021
INVENTOR(S) : Beisel et al.

Page 1 of 2

It is certified that error appears in the above-identified patent and that said Letters Patent is hereby corrected as shown below:

On the Title Page

Item [56], Page 2, Column 1, Line 36: delete "WO 20131188638" and insert -- WO 2013/188638 --

Item [56], Page 2, Column 1, Line 43: delete "WO 20141124226" and insert -- WO 2014/124226 --

Item [56], Page 2, Column 1, Line 46: delete "WO 20141144592" and insert -- WO 2014/144592 --

Item [56], Page 3, Column 1, Line 39: delete "Internetional" and insert -- International --

Item [56], Page 3, Column 1, Line 51: delete "MIcrobiolcay" and insert -- Microbiology --

Item [56], Page 4, Column 2, Line 40: delete "Lido" and insert -- Luo --

Item [56], Page 4, Column 2, Lines 43-44: delete "16/153.052, dated Dec. 26, 2018. 14 pages." and insert -- 16/153,052, dated Dec. 26, 2018, 14 pages. --

In the Specification

Column 6, Line 12: delete "DpnI." and insert -- Dpn1. --

Column 6, Line 37: delete "P1-ΔimcB/coi:kan$^R$" and insert -- P1-ΔimcB/coi::kan$^R$ --

Column 6, Line 38: delete "P1-ΔsimABC:kan$^R$" and insert -- P1-ΔsimABC::kan$^R$ --

Column 6, Line 39: delete "P1-ΔimcB/coi:cm$^R$" and insert -- P1-ΔimcB/coi::cm$^R$ --

Column 6, Lines 40-41: delete "P1-ΔimcB/coi:cm$^R$" and insert -- P1-ΔimcB/coi::cm$^R$ --

Column 6, Line 41: delete "P1-ΔimcB/coi:kan$^R$" and insert -- P1-ΔimcB/coi::kan$^R$ --

Signed and Sealed this
Twelfth Day of April, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,155,823 B2

Column 6, Line 42: delete "P1-ΔsimABC:kan$^R$" and insert -- P1-ΔsimABC::kan$^R$ --

Column 6, Line 51: delete "P1 coi-icmB:kanR" and insert -- P1 coi-icmB::kanR --

Column 7, Lines 21-22: delete "P1 imcB-coi:kanR" and insert -- P1 imcB-coi::kanR --

Column 10, Line 4: delete "5°" and insert -- 5' --

Column 22, Line 21: delete "15-lac" and insert -- T5-lac --

Column 36, Line 3: delete "Cyst" and insert -- Cys1 --

Column 42, Line 14: delete "P I Shaking" and insert -- P1. Shaking --

Column 42, Line 18: delete "Chlorofolin" and insert -- Chloroform --

Column 46, Line 49: delete "P1-ΔimcB/coi:kan$^R$" and insert -- P1-ΔimcB/coi::kan$^R$ --

Column 46, Lines 49-50: delete "P1-ΔsimABC:kan$^R$" and insert -- P1-ΔsimABC::kan$^R$ --

Column 46, Line 56: delete "P1 ΔimcB/coi:cm$^R$" and insert -- P1-ΔimcB/coi::cm$^R$ --

Column 47, Line 60: delete "P1-ΔimcB/coi:cm$^R$, P1-ΔIS1:kan$^R$, or P1-ΔsimABC:kan$^R$" and insert -- P1-ΔimcB/coi::cm$^R$, P1-ΔIS1::kan$^R$, or P1-ΔsimABC::kan$^R$ --

Column 48, Line 10: delete "P1-ΔimcB/coi:kan$^R$" and insert -- P1-ΔimcB/coi::kan$^R$ --

Column 48, Line 11: delete "P1-ΔsimABC:kan$^R$" and insert -- P1-ΔsimABC::kan$^R$ --

Column 48, Line 12: delete "P1-ΔimcB/coi:kan$^R$" and insert -- P1-ΔimcB/coi::kan$^R$ --

Column 48, Line 12: delete "P1-ΔsimABC:kan$^R$" and insert -- P1-ΔsimABC::kan$^R$ --

Column 48, Line 13: delete "P1-ΔimcB/coi:cm$^R$" and insert -- P1-ΔimcB/coi::cm$^R$ --

Column 48, Line 49: delete "P1-ΔimcB/coi:kan$^R$" and insert -- P1-ΔimcB/coi::kan$^R$ --

Column 52, Line 46: delete "1.9x10∧11" and insert -- 1.9x10^11 --